United States Patent
Kaiser et al.

(10) Patent No.: US 9,532,777 B2
(45) Date of Patent: Jan. 3, 2017

(54) METHOD AND APPARATUS FOR COUPLING SOFT TISSUE TO A BONE

(71) Applicant: Biomet Sports Medicine, LLC, Warsaw, IN (US)

(72) Inventors: Ryan A. Kaiser, Leesburg, IN (US); Gregory J. Denham, Warsaw, IN (US); Kevin T. Stone, Winona Lake, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 285 days.

(21) Appl. No.: 14/107,350

(22) Filed: Dec. 16, 2013

(65) Prior Publication Data

US 2014/0194927 A1  Jul. 10, 2014

Related U.S. Application Data

(60) Division of application No. 13/278,341, filed on Oct. 21, 2011, now Pat. No. 8,608,777, which is a
(Continued)

(51) Int. Cl.
*A61B 17/04* (2006.01)
*A61F 2/08* (2006.01)
(Continued)

(52) U.S. Cl.
CPC ......... *A61B 17/0401* (2013.01); *A61F 2/0811* (2013.01); *A61B 17/0487* (2013.01);
(Continued)

(58) Field of Classification Search
CPC ............ A61B 17/0401; A61B 17/0487; A61B 2017/00858; A61B 2017/0417; A61B 2017/044; A61B 2017/0496; A61B 2017/00336; A61B 2017/0409; A61B 2017/0432; A61B 2017/0477; A61B 2017/06185; A61F 2/0811; A61F 2002/0882; A61F 2002/0888
See application file for complete search history.

(56) References Cited

U.S. PATENT DOCUMENTS 26,501 A   12/1859   Kendrick et al.
64,499 A   5/1867    Daubert
(Continued)

FOREIGN PATENT DOCUMENTS

AU   4957264   3/1966
AU   440266    10/1967
(Continued)

OTHER PUBLICATIONS

US 6,238,418, 05/2001, Schwartz et al. (withdrawn)
(Continued)

*Primary Examiner* — Gregory Anderson
*Assistant Examiner* — Son Dang
(74) *Attorney, Agent, or Firm* — Schwegman Lundberg & Woessner, P.A.

(57) ABSTRACT

A method for coupling soft tissue to bone including: positioning a first anchor in a first bone bore, the first anchor having a first self-locking adjustable suture construct including a first adjustable loop, a second adjustable loop, and a pair of first ends; positioning a second anchor in a second bone bore, the second anchor having a second self-locking adjustable suture construct including a third adjustable loop, a fourth adjustable loop, and a second end; positioning the first adjustable loop relative to the soft tissue; positioning the second adjustable loop about the third adjustable loop; and tensioning the pair of first ends and the second end to pull the first adjustable loop against the soft tissue, couple the second adjustable loop to the third adjustable loop, pull the second adjustable loop against the soft tissue, and pull the third adjustable loop against the soft tissue.

20 Claims, 43 Drawing Sheets

Related U.S. Application Data continuation of application No. 12/474,802, filed on May 29, 2009, now Pat. No. 8,088,130, which is a continuation-in-part of application No. 11/541,506, filed on Sep. 29, 2006, now Pat. No. 7,601,165, and a continuation-in-part of application No. 11/541,505, filed on Sep. 29, 2006, now Pat. No. 7,658,751, and a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, and a continuation-in-part of application No. 11/935,681, filed on Nov. 6, 2007, now Pat. No. 7,905,903, and a continuation-in-part of application No. 11/869,440, filed on Oct. 9, 2007, now Pat. No. 7,857,830, and a continuation-in-part of application No. 11/784,821, filed on Apr. 10, 2007, now Pat. No. 9,017,381, and a continuation-in-part of application No. 11/347,661, filed on Feb. 3, 2006, now Pat. No. 7,749,250, and a continuation-in-part of application No. 11/347,662, filed on Feb. 3, 2006, now abandoned, application No. 14/107,350, which is a continuation-in-part of application No. 13/412,105, filed on Mar. 5, 2012, now Pat. No. 8,932,331, which is a continuation-in-part of application No. 12/196,410, filed on Aug. 22, 2008, now Pat. No. 8,118,836, and a continuation-in-part of application No. 12/196,407, filed on Aug. 22, 2008, now Pat. No. 8,137,382, and a continuation-in-part of application No. 12/196,405, filed on Aug. 22, 2008, now Pat. No. 8,128,658.

(51) Int. Cl.
    *A61B 17/00* (2006.01)
    *A61B 17/06* (2006.01)

(52) U.S. Cl.
    CPC ............ *A61B 2017/00336* (2013.01); *A61B 2017/00858* (2013.01); *A61B 2017/044* (2013.01); *A61B 2017/0409* (2013.01); *A61B 2017/0417* (2013.01); *A61B 2017/0432* (2013.01); *A61B 2017/0477* (2013.01); *A61B 2017/0496* (2013.01); *A61B 2017/06185* (2013.01); *A61F 2002/0882* (2013.01); *A61F 2002/0888* (2013.01)

(56) References Cited

U.S. PATENT DOCUMENTS

| | | |
|---|---|---|
| 65,499 A | 6/1867 | Miller |
| 126,366 A | 4/1872 | Wills |
| 233,475 A | 10/1880 | Cook et al. |
| 261,501 A | 7/1882 | Vandermark |
| 268,407 A | 12/1882 | Hughes |
| 330,087 A | 11/1885 | Binns |
| 394,739 A | 12/1888 | Toulmin |
| 401,677 A | 4/1889 | Autenrieth |
| 417,805 A | 12/1889 | Beaman |
| 445,875 A | 2/1891 | Brickell |
| 487,304 A | 12/1892 | Todd |
| 762,710 A | 6/1901 | Hall |
| 687,221 A | 11/1901 | Gaff et al. |
| 837,767 A | 12/1906 | Aims |
| 838,203 A | 12/1906 | Neil |
| 1,059,631 A | 4/1913 | Popovics |
| 1,131,155 A | 3/1915 | Murphy |
| 1,153,450 A | 9/1915 | Schaff |
| 1,346,940 A | 7/1920 | Collins |
| 1,635,066 A | 7/1927 | Wells |
| 1,950,799 A | 3/1934 | Jones |
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| 2,379,629 A | 7/1945 | Eweson |
| 2,397,216 A | 3/1946 | Stellin |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 6/1962 | Chandler |
| 3,081,781 A | 3/1963 | Stermer |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,223,083 A | 12/1965 | Cobey |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Himmelstein et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,650,274 A | 3/1972 | Edwards et al. |
| 3,656,483 A | 4/1972 | Rudel |
| 3,659,597 A | 5/1972 | Wolfers |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |

(56) References Cited

U.S. PATENT DOCUMENTS

| | | |
|---|---|---|
| 3,763,856 A | 10/1973 | Blomberg |
| 3,771,520 A | 11/1973 | Lerner |
| 3,777,748 A | 12/1973 | Abramson |
| 3,786,801 A | 1/1974 | Sartorius |
| 3,807,407 A | 4/1974 | Schweizer |
| 3,810,456 A | 5/1974 | Karman |
| 3,825,010 A | 7/1974 | McDonald |
| 3,840,017 A | 10/1974 | Violante |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,896,810 A | 7/1975 | Akiyama |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,446 A | 3/1976 | Schofield |
| 3,946,728 A | 3/1976 | Bettex |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,036,101 A | 7/1977 | Burnett |
| 4,050,100 A | 9/1977 | Barry |
| 4,054,954 A | 10/1977 | Nakayama et al. |
| 4,084,478 A | 4/1978 | Simmons |
| 4,085,466 A | 4/1978 | Goodfellow et al. |
| 4,094,313 A | 6/1978 | Komamura et al. |
| 4,099,750 A | 7/1978 | McGrew |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,146,022 A | 3/1979 | Johnson et al. |
| 4,149,277 A | 4/1979 | Bokros |
| 4,157,714 A | 6/1979 | Foltz et al. |
| 4,158,250 A | 6/1979 | Ringwald |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,207,627 A | 6/1980 | Cloutier |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,490 A | 6/1981 | Bivins |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,302,397 A | 11/1981 | Frainier et al. |
| 4,307,723 A | 12/1981 | Finney |
| 4,312,337 A | 1/1982 | Donohue |
| 4,316,469 A | 2/1982 | Kapitanov et al. |
| 4,326,531 A | 4/1982 | Shimonaka et al. |
| 4,344,193 A | 8/1982 | Kenny |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |
| 4,409,974 A | 10/1983 | Freedland |
| 4,438,769 A | 3/1984 | Pratt et al. |
| 4,441,489 A | 4/1984 | Evans et al. |
| 4,454,875 A | 6/1984 | Pratt et al. |
| 4,462,395 A | 7/1984 | Johnson |
| 4,463,753 A | 8/1984 | Gustilo |
| 4,473,102 A | 9/1984 | Ohman et al. |
| 4,484,570 A | 11/1984 | Sutter et al. |
| 4,489,446 A | 12/1984 | Reed |
| 4,489,464 A | 12/1984 | Massari et al. |
| 4,493,323 A | 1/1985 | Albright et al. |
| 4,496,468 A | 1/1985 | House et al. |
| 4,505,274 A | 3/1985 | Speelman |
| 4,509,516 A | 4/1985 | Richmond |
| 4,531,522 A | 7/1985 | Bedi et al. |
| 4,532,926 A | 8/1985 | O'Holla |
| 4,534,350 A | 8/1985 | Golden et al. |
| 4,535,764 A | 8/1985 | Ebert |
| 4,537,185 A | 8/1985 | Stednitz |
| 4,549,545 A | 10/1985 | Levy |
| 4,549,652 A | 10/1985 | Free |
| 4,561,432 A | 12/1985 | Mazor |
| 4,564,007 A | 1/1986 | Coombs et al. |
| 4,570,623 A | 2/1986 | Ellison et al. |
| 4,573,844 A | 3/1986 | Smith |
| 4,576,608 A | 3/1986 | Homsy |
| 4,584,722 A | 4/1986 | Levy et al. |
| 4,587,963 A | 5/1986 | Leibinger et al. |
| 4,590,928 A | 5/1986 | Hunt et al. |
| 4,595,007 A | 6/1986 | Mericle |
| 4,596,249 A | 6/1986 | Freda et al. |
| 4,597,766 A | 7/1986 | Hilal et al. |
| 4,602,635 A | 7/1986 | Mulhollan et al. |
| 4,602,636 A | 7/1986 | Noiles |
| 4,604,997 A | 8/1986 | De Bastiani et al. |
| 4,605,414 A | 8/1986 | Czajka |
| 4,616,650 A | 10/1986 | Green et al. |
| 4,621,640 A | 11/1986 | Mulhollan et al. |
| 4,624,254 A | 11/1986 | McGarry et al. |
| 4,632,100 A | 12/1986 | Somers et al. |
| 4,635,637 A | 1/1987 | Schreiber |
| 4,636,121 A | 1/1987 | Miller |
| 4,641,652 A | 2/1987 | Hutterer et al. |
| 4,649,916 A | 3/1987 | Frimberger |
| 4,649,952 A | 3/1987 | Jobe |
| 4,653,486 A | 3/1987 | Coker |
| 4,653,487 A | 3/1987 | Maale |
| 4,653,489 A | 3/1987 | Tronzo |
| 4,655,777 A | 4/1987 | Dunn et al. |
| 4,662,068 A | 5/1987 | Polonsky |
| 4,667,662 A | 5/1987 | Titone et al. |
| 4,667,675 A | 5/1987 | Davis |
| 4,669,473 A | 6/1987 | Richards et al. |
| 4,683,895 A | 8/1987 | Pohndorf |
| 4,688,561 A | 8/1987 | Reese |
| 4,690,169 A | 9/1987 | Jobe |

(56) References Cited

U.S. PATENT DOCUMENTS

| | | |
|---|---|---|
| 4,696,300 A | 9/1987 | Anderson |
| 4,705,040 A | 11/1987 | Mueller et al. |
| 4,708,132 A | 11/1987 | Silvestrini |
| 4,714,475 A | 12/1987 | Grundei et al. |
| 4,716,893 A | 1/1988 | Fischer et al. |
| 4,719,671 A | 1/1988 | Ito et al. |
| 4,719,917 A | 1/1988 | Barrows et al. |
| 4,723,540 A | 2/1988 | Gilmer, Jr. |
| 4,724,839 A | 2/1988 | Bedi et al. |
| 4,728,332 A | 3/1988 | Albrektsson |
| 4,736,746 A | 4/1988 | Anderson |
| 4,738,255 A | 4/1988 | Goble et al. |
| 4,739,751 A | 4/1988 | Sapega et al. |
| 4,741,330 A | 5/1988 | Hayhurst |
| 4,741,336 A | 5/1988 | Failla et al. |
| 4,744,353 A | 5/1988 | McFarland |
| 4,744,793 A | 5/1988 | Parr et al. |
| 4,750,492 A | 6/1988 | Jacobs |
| 4,751,922 A | 6/1988 | Dipietropolo |
| 4,760,843 A | 8/1988 | Fischer et al. |
| 4,760,844 A | 8/1988 | Kyle |
| 4,760,848 A | 8/1988 | Hasson |
| 4,770,663 A | 9/1988 | Hanslik et al. |
| 4,772,261 A | 9/1988 | Von Hoff et al. |
| 4,772,286 A | 9/1988 | Goble et al. |
| 4,773,910 A | 9/1988 | Chen et al. |
| 4,775,380 A | 10/1988 | Seedhom et al. |
| 4,776,328 A | 10/1988 | Frey et al. |
| 4,781,190 A | 11/1988 | Lee et al. |
| 4,784,126 A | 11/1988 | Hourahane |
| 4,787,882 A | 11/1988 | Claren et al. |
| 4,790,297 A | 12/1988 | Luque et al. |
| 4,790,850 A | 12/1988 | Dunn et al. |
| 4,793,363 A | 12/1988 | Ausherman et al. |
| 4,809,695 A | 3/1989 | Gwathmey et al. |
| 4,813,406 A | 3/1989 | Ogle, II |
| 4,823,780 A | 4/1989 | Odensten et al. |
| 4,823,794 A | 4/1989 | Pierce |
| 4,828,562 A | 5/1989 | Kenna |
| 4,832,026 A | 5/1989 | Jones |
| 4,834,098 A | 5/1989 | Jones |
| 4,838,282 A | 6/1989 | Strasser et al. |
| 4,841,960 A | 6/1989 | Garner |
| 4,846,835 A | 7/1989 | Grande |
| 4,851,005 A | 7/1989 | Hunt et al. |
| 4,858,601 A | 8/1989 | Glisson |
| 4,858,603 A | 8/1989 | Clemow et al. |
| 4,858,608 A | 8/1989 | McQuilkin et al. |
| 4,860,513 A | 8/1989 | Whitman |
| 4,863,383 A | 9/1989 | Grafelmann et al. |
| 4,870,957 A | 10/1989 | Goble et al. |
| 4,872,450 A | 10/1989 | Austad |
| 4,873,976 A | 10/1989 | Schreiber |
| 4,884,572 A | 12/1989 | Bays et al. |
| 4,887,601 A | 12/1989 | Richards |
| 4,889,110 A | 12/1989 | Galline et al. |
| 4,890,615 A | 1/1990 | Caspari et al. |
| 4,893,619 A | 1/1990 | Dale et al. |
| 4,893,974 A | 1/1990 | Fischer et al. |
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,919,667 A | 4/1990 | Richmond |
| 4,922,897 A | 5/1990 | Sapega et al. |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht et al. |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,545 A | 3/1991 | Whiteside et al. |
| 5,002,550 A | 3/1991 | Li |
| 5,002,562 A | 3/1991 | Oberlander |
| 5,002,574 A | 3/1991 | May et al. |
| 5,007,921 A | 4/1991 | Brown |
| 5,020,713 A | 6/1991 | Kunreuther |
| 5,028,569 A | 7/1991 | Cihon |
| 5,030,224 A | 7/1991 | Wright et al. |
| 5,030,235 A | 7/1991 | Campbell, Jr. |
| 5,035,701 A | 7/1991 | Kabbara |
| 5,037,422 A | 8/1991 | Hayhurst et al. |
| 5,037,426 A | 8/1991 | Goble et al. |
| 5,041,129 A | 8/1991 | Hayhurst et al. |
| 5,046,513 A | 9/1991 | Gatturna et al. |
| 5,047,030 A | 9/1991 | Draenert et al. |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,067,962 A | 11/1991 | Campbell et al. |
| 5,071,420 A | 12/1991 | Paulos et al. |
| 5,074,874 A | 12/1991 | Yoon et al. |
| 5,078,731 A | 1/1992 | Hayhurst |
| 5,078,843 A | 1/1992 | Pratt |
| 5,080,050 A | 1/1992 | Dale |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,108,433 A | 4/1992 | May et al. |
| 5,112,335 A | 5/1992 | Laboureau et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,151,104 A | 9/1992 | Kenna |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,171,274 A | 12/1992 | Fluckiger et al. |
| 5,176,682 A | 1/1993 | Chow |
| 5,178,629 A | 1/1993 | Kammerer |
| 5,183,458 A | 2/1993 | Marx |
| 5,190,545 A | 3/1993 | Corsi et al. |

(56) References Cited

U.S. PATENT DOCUMENTS

| | | |
|---|---|---|
| 5,192,282 A | 3/1993 | Draenert et al. |
| 5,197,987 A | 3/1993 | Koch et al. |
| 5,199,135 A | 4/1993 | Gold |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,940 A | 7/1993 | Dann et al. |
| 5,224,946 A | 7/1993 | Hayhurst et al. |
| 5,226,914 A | 7/1993 | Caplan et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,282,868 A | 2/1994 | Bahler |
| 5,285,040 A | 2/1994 | Brandberg et al. |
| 5,290,217 A | 3/1994 | Campos |
| 5,290,243 A | 3/1994 | Chodorow et al. |
| 5,306,301 A | 4/1994 | Graf et al. |
| 5,312,410 A | 5/1994 | Miller et al. |
| 5,312,422 A | 5/1994 | Trott |
| 5,312,438 A | 5/1994 | Johnson |
| 5,314,429 A | 5/1994 | Goble |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,350,380 A | 9/1994 | Goble et al. |
| RE34,762 E | 10/1994 | Goble et al. |
| 5,354,292 A | 10/1994 | Braeuer et al. |
| 5,354,298 A | 10/1994 | Lee et al. |
| 5,354,299 A | 10/1994 | Coleman |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,362,911 A | 11/1994 | Cevasco et al. |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,374,269 A | 12/1994 | Rosenberg |
| 5,379,492 A | 1/1995 | Glesser |
| 5,383,878 A | 1/1995 | Roger et al. |
| 5,383,904 A | 1/1995 | Totakura et al. |
| 5,385,567 A | 1/1995 | Goble |
| 5,391,171 A | 2/1995 | Schmieding |
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,395,374 A | 3/1995 | Miller et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,411,550 A | 5/1995 | Herweck et al. |
| 5,415,658 A | 5/1995 | Kilpela et al. |
| 5,417,690 A | 5/1995 | Sennett et al. |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,824 A | 6/1995 | Akerfeldt et al. |
| 5,423,860 A | 6/1995 | Lizardi et al. |
| 5,425,733 A | 6/1995 | Schmieding |
| 5,425,766 A | 6/1995 | Bowald et al. |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch et al. |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,721 A | 10/1995 | Legrand |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson et al. |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,476,465 A | 12/1995 | Preissman |
| 5,478,344 A | 12/1995 | Stone et al. |
| 5,478,345 A | 12/1995 | Stone et al. |
| 5,480,403 A | 1/1996 | Lee et al. |

(56) References Cited

U.S. PATENT DOCUMENTS

| | | |
|---|---|---|
| 5,480,406 A | 1/1996 | Nolan et al. |
| 5,484,442 A | 1/1996 | Melker et al. |
| 5,486,197 A | 1/1996 | Le et al. |
| 5,486,359 A | 1/1996 | Caplan et al. |
| 5,490,750 A | 2/1996 | Gundy |
| 5,495,974 A | 3/1996 | Deschenes et al. |
| 5,496,290 A | 3/1996 | Ackerman |
| 5,496,331 A | 3/1996 | Xu et al. |
| 5,496,348 A | 3/1996 | Bonutti |
| 5,498,302 A | 3/1996 | Davidson |
| 5,500,000 A | 3/1996 | Feagin et al. |
| 5,505,735 A | 4/1996 | Li |
| 5,505,736 A | 4/1996 | Reimels et al. |
| 5,507,754 A | 4/1996 | Green et al. |
| 5,520,691 A | 5/1996 | Branch |
| 5,520,694 A | 5/1996 | Dance et al. |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,843 A | 6/1996 | Zang |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,534,033 A | 7/1996 | Simpson |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,664 A | 10/1996 | Durlacher et al. |
| 5,562,668 A | 10/1996 | Johnson |
| 5,562,669 A | 10/1996 | McGuire |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,569,306 A | 10/1996 | Thal |
| 5,570,706 A | 11/1996 | Howell |
| 5,571,090 A | 11/1996 | Sherts |
| 5,571,104 A | 11/1996 | Li |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,547 A | 11/1996 | LeVeen et al. |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,607,430 A | 3/1997 | Bailey |
| 5,613,971 A | 3/1997 | Lower et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,745 A | 5/1997 | Schwartz |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,273 A | 7/1997 | Clark |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,960 A | 7/1997 | Pavletic |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,677 A | 9/1997 | Wimmer |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,404 A | 11/1997 | Johnson |
| 5,683,419 A | 11/1997 | Thal |
| 5,688,284 A | 11/1997 | Chervitz et al. |
| 5,688,285 A | 11/1997 | Yamada et al. |
| 5,690,655 A | 11/1997 | Hart et al. |
| 5,690,676 A | 11/1997 | DiPoto et al. |
| 5,690,678 A | 11/1997 | Johnson |
| 5,693,046 A | 12/1997 | Songer et al. |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,709,708 A | 1/1998 | Thal |
| 5,711,969 A | 1/1998 | Patel et al. |
| 5,713,005 A | 1/1998 | Proebsting |
| 5,713,897 A | 2/1998 | Goble et al. |
| 5,713,904 A | 2/1998 | Errico et al. |
| 5,713,905 A | 2/1998 | Goble et al. |
| 5,713,921 A | 2/1998 | Bonutti |
| 5,715,578 A | 2/1998 | Knudson |
| 5,716,359 A | 2/1998 | Ojima et al. |
| 5,716,397 A | 2/1998 | Myers |
| 5,716,616 A | 2/1998 | Prockop et al. |
| 5,718,717 A | 2/1998 | Bonutti |
| 5,720,747 A | 2/1998 | Burke |
| 5,720,765 A | 2/1998 | Thal |
| 5,720,766 A | 2/1998 | Zang et al. |
| 5,722,976 A | 3/1998 | Brown |
| 5,723,331 A | 3/1998 | Tubo et al. |
| 5,725,529 A | 3/1998 | Nicholson et al. |
| 5,725,549 A | 3/1998 | Lam |

(56) References Cited

U.S. PATENT DOCUMENTS

| | | |
|---|---|---|
| 5,725,556 A | 3/1998 | Moser et al. |
| 5,725,557 A | 3/1998 | Gatturna et al. |
| 5,725,581 A | 3/1998 | Brånemark |
| 5,725,582 A | 3/1998 | Bevan et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,260 A | 4/1998 | Songer et al. |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,755,791 A | 5/1998 | Whitson et al. |
| 5,766,176 A | 6/1998 | Duncan |
| 5,766,218 A | 6/1998 | Arnott |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,776,200 A | 7/1998 | Johnson et al. |
| 5,782,845 A | 7/1998 | Shewchuk |
| 5,782,862 A | 7/1998 | Bonutti |
| 5,782,864 A | 7/1998 | Lizardi |
| 5,782,866 A | 7/1998 | Wenstrom, Jr. |
| 5,782,925 A | 7/1998 | Collazo et al. |
| 5,785,714 A | 7/1998 | Morgan et al. |
| 5,786,217 A | 7/1998 | Tubo et al. |
| 5,792,142 A | 8/1998 | Galitzer |
| 5,792,149 A | 8/1998 | Sherts et al. |
| 5,796,127 A | 8/1998 | Hayafuji et al. |
| 5,797,913 A | 8/1998 | Dambreville et al. |
| 5,797,915 A | 8/1998 | Pierson, III et al. |
| 5,797,916 A | 8/1998 | McDowell |
| 5,797,928 A | 8/1998 | Kogasaka |
| 5,800,407 A | 9/1998 | Eldor et al. |
| 5,810,824 A | 9/1998 | Chan |
| 5,810,848 A | 9/1998 | Hayhurst |
| 5,811,094 A | 9/1998 | Caplan et al. |
| 5,814,056 A | 9/1998 | Prosst et al. |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,817,095 A | 10/1998 | Smith |
| 5,823,980 A | 10/1998 | Kopfer |
| 5,824,011 A | 10/1998 | Stone et al. |
| 5,824,066 A | 10/1998 | Gross |
| 5,830,234 A | 11/1998 | Wojciechowicz et al. |
| 5,836,955 A | 11/1998 | Buelna et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,849,012 A | 12/1998 | Abboudi |
| 5,860,947 A | 1/1999 | Stamler |
| 5,860,973 A | 1/1999 | Michelson |
| 5,860,978 A | 1/1999 | McDevitt et al. |
| 5,868,740 A | 2/1999 | LeVeen et al. |
| 5,868,748 A | 2/1999 | Burke |
| 5,868,789 A | 2/1999 | Huebner |
| 5,871,456 A | 2/1999 | Armstrong et al. |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,906,934 A | 5/1999 | Grande et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,916,557 A | 6/1999 | Berlowitz-tarrant et al. |
| 5,918,604 A | 7/1999 | Whelan |
| 5,921,986 A | 7/1999 | Bonutti |
| 5,925,008 A | 7/1999 | Douglas |
| 5,928,231 A | 7/1999 | Klein et al. |
| 5,928,267 A | 7/1999 | Bonutti et al. |
| 5,928,286 A | 7/1999 | Ashby et al. |
| RE36,289 E | 8/1999 | Le et al. |
| 5,931,838 A | 8/1999 | Vito |
| 5,931,844 A | 8/1999 | Thompson et al. |
| 5,931,869 A | 8/1999 | Boucher et al. |
| 5,935,119 A | 8/1999 | Guy et al. |
| 5,935,133 A | 8/1999 | Wagner et al. |
| 5,935,134 A | 8/1999 | Pedlick et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,947,999 A | 9/1999 | Groiso |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,520 A | 10/1999 | Beck, Jr. et al. |
| 5,961,521 A | 10/1999 | Roger et al. |
| 5,961,524 A | 10/1999 | Crombie |
| 5,963,869 A | 10/1999 | Fehnel |
| 5,964,764 A | 10/1999 | West, Jr. et al. |
| 5,964,767 A | 10/1999 | Tapia et al. |
| 5,964,769 A | 10/1999 | Wagner et al. |
| 5,964,783 A | 10/1999 | Grafton et al. |
| 5,968,045 A | 10/1999 | Frazier |
| 5,968,047 A | 10/1999 | Reed |
| 5,968,077 A | 10/1999 | Wojciechowicz et al. |
| 5,970,697 A | 10/1999 | Jacobs et al. |
| 5,972,006 A | 10/1999 | Sciaino, Jr. |
| 5,976,125 A | 11/1999 | Graham |
| 5,976,127 A | 11/1999 | Lax |
| 5,980,473 A | 11/1999 | Korakianitis et al. |
| 5,980,524 A | 11/1999 | Justin et al. |
| 5,980,539 A | 11/1999 | Kontos |
| 5,980,548 A | 11/1999 | Evans et al. |
| 5,980,558 A | 11/1999 | Wiley |
| 5,980,559 A | 11/1999 | Bonutti |
| 5,989,252 A | 11/1999 | Fumex |
| 5,989,256 A | 11/1999 | Kuslich et al. |
| 5,989,282 A | 11/1999 | Bonutti |
| 5,989,294 A | 11/1999 | Marlow |
| 5,993,452 A | 11/1999 | Vandewalle |
| 5,993,476 A | 11/1999 | Groiso |
| 5,997,542 A | 12/1999 | Burke |
| 5,997,552 A | 12/1999 | Person et al. |
| 5,997,575 A | 12/1999 | Whitson et al. |
| 6,001,100 A | 12/1999 | Sherman et al. |
| 6,001,106 A | 12/1999 | Ryan et al. |
| 6,004,351 A | 12/1999 | Tomita et al. |
| 6,004,352 A | 12/1999 | Buni |
| 6,007,538 A | 12/1999 | Levin |
| 6,007,567 A | 12/1999 | Bonutti |
| 6,010,525 A | 1/2000 | Bonutti et al. |
| 6,013,103 A | 1/2000 | Kaufman et al. |
| 6,016,727 A | 1/2000 | Morgan |

(56) References Cited

U.S. PATENT DOCUMENTS

| | | |
|---|---|---|
| 6,019,767 A | 2/2000 | Howell |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,030,410 A | 2/2000 | Zurbrugg |
| 6,033,429 A | 3/2000 | Magovern |
| 6,033,430 A | 3/2000 | Bonutti |
| 6,036,695 A | 3/2000 | Smith |
| 6,039,753 A | 3/2000 | Meislin |
| 6,041,485 A | 3/2000 | Pedlick et al. |
| 6,042,601 A | 3/2000 | Smith |
| 6,042,609 A | 3/2000 | Giordano et al. |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,066,173 A | 5/2000 | McKernan et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,102,934 A | 8/2000 | Li |
| 6,106,545 A | 8/2000 | Egan |
| 6,110,128 A | 8/2000 | Andelin et al. |
| 6,110,207 A | 8/2000 | Eichhorn et al. |
| 6,113,604 A | 9/2000 | Whittaker et al. |
| 6,117,160 A | 9/2000 | Bonutti |
| 6,117,162 A | 9/2000 | Schmieding et al. |
| 6,123,710 A | 9/2000 | Pinczewski et al. |
| 6,127,596 A | 10/2000 | Brown et al. |
| 6,132,433 A | 10/2000 | Whelan |
| 6,132,437 A | 10/2000 | Omurtag et al. |
| 6,136,010 A | 10/2000 | Modesitt et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,150,163 A | 11/2000 | McPherson et al. |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,171,310 B1 | 1/2001 | Giordano et al. |
| 6,179,840 B1 | 1/2001 | Bowman |
| 6,183,461 B1 | 2/2001 | Matsuura et al. |
| 6,183,737 B1 | 2/2001 | Zaleske et al. |
| 6,187,025 B1 | 2/2001 | Machek |
| 6,190,348 B1 | 2/2001 | Tiemann et al. |
| 6,190,401 B1 | 2/2001 | Green et al. |
| 6,190,411 B1 | 2/2001 | Lo et al. |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,200,606 B1 | 3/2001 | Peterson et al. |
| 6,200,685 B1 | 3/2001 | Davidson |
| 6,203,556 B1 | 3/2001 | Evans et al. |
| 6,203,563 B1 | 3/2001 | Fernandez |
| 6,203,565 B1 | 3/2001 | Bonutti et al. |
| 6,203,572 B1 | 3/2001 | Johnson et al. |
| 6,203,576 B1 | 3/2001 | Afriat et al. |
| 6,206,883 B1 | 3/2001 | Tunc |
| 6,210,376 B1 | 4/2001 | Grayson |
| 6,210,381 B1 | 4/2001 | Morse |
| 6,214,007 B1 | 4/2001 | Anderson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,234,980 B1 | 5/2001 | Bell |
| 6,235,057 B1 | 5/2001 | Roger et al. |
| 6,235,058 B1 | 5/2001 | Huene |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,254,604 B1 | 7/2001 | Howell |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,929 B1 | 9/2001 | Smith et al. |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,302,915 B1 | 10/2001 | Cooney, III et al. |
| 6,303,158 B1 | 10/2001 | Odgaard et al. |
| 6,306,156 B1 | 10/2001 | Clark |
| 6,306,158 B1 | 10/2001 | Bartlett |
| 6,306,159 B1 | 10/2001 | Schwartz et al. |
| 6,309,124 B1 | 10/2001 | Gueret |
| 6,309,405 B1 | 10/2001 | Bonutti |
| 6,312,448 B1 | 11/2001 | Bonutti |
| 6,315,788 B1 | 11/2001 | Roby |
| 6,319,224 B1 | 11/2001 | Stout et al. |
| 6,319,271 B1 | 11/2001 | Schwartz et al. |
| 6,328,758 B1 | 12/2001 | Tornier et al. |
| 6,334,064 B1 | 12/2001 | Fiddian-green |
| 6,342,060 B1 | 1/2002 | Adams |
| 6,343,531 B2 | 2/2002 | Amis |
| 6,355,066 B1 | 3/2002 | Kim |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |

(56) References Cited

U.S. PATENT DOCUMENTS

| | | |
|---|---|---|
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,456 B1 | 6/2002 | Slate et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,073 B2 | 7/2002 | Bowman |
| 6,423,088 B1 | 7/2002 | Fenton, Jr. |
| 6,425,924 B1 | 7/2002 | Rousseau |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,458,161 B1 | 10/2002 | Gibbs et al. |
| 6,461,373 B2 | 10/2002 | Wyman et al. |
| 6,464,690 B1 | 10/2002 | Castaneda et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,478,753 B2 | 11/2002 | Reay-Young |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,514,274 B1 | 2/2003 | Boucher et al. |
| 6,517,542 B1 | 2/2003 | Papay et al. |
| 6,517,552 B1 | 2/2003 | Nord et al. |
| 6,517,564 B1 | 2/2003 | Grafton et al. |
| 6,517,578 B2 | 2/2003 | Hein |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,540,783 B1 | 4/2003 | Whittaker et al. |
| 6,543,094 B2 | 4/2003 | D'addario |
| 6,544,281 B2 | 4/2003 | ElAttrache et al. |
| 6,547,564 B1 | 4/2003 | Hansson et al. |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,551,353 B1 | 4/2003 | Baker et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,558,389 B2 | 5/2003 | Clark et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,572,655 B1 | 6/2003 | Johnson |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,592,622 B1 | 7/2003 | Ferguson |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues |
| 6,626,919 B1 | 9/2003 | Swanstrom |
| 6,626,930 B1 | 9/2003 | Allen et al. |
| 6,629,977 B1 | 10/2003 | Wolf |
| 6,629,997 B2 | 10/2003 | Mansmann |
| 6,632,245 B2 | 10/2003 | Kim |
| 6,635,073 B2 | 10/2003 | Bonutti |
| 6,638,279 B2 | 10/2003 | Bonutti |
| 6,638,286 B1 | 10/2003 | Burbank et al. |
| 6,638,312 B2 | 10/2003 | Plouhar et al. |
| 6,641,596 B1 | 11/2003 | Lizardi |
| 6,641,597 B2 | 11/2003 | Burkhart et al. |
| 6,645,169 B1 | 11/2003 | Slate et al. |
| 6,645,211 B2 | 11/2003 | Magana |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,533 B2 | 11/2003 | O'neil |
| 6,652,560 B1 | 11/2003 | Gerke et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,669,707 B1 | 12/2003 | Swanstrom et al. |
| 6,679,889 B1 | 1/2004 | West, Jr. et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,695,852 B2 | 2/2004 | Gleason |
| 6,712,849 B2 | 3/2004 | Re et al. |
| 6,712,859 B2 | 3/2004 | Rousseau |
| 6,716,190 B1 | 4/2004 | Glines et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |

(56) References Cited

U.S. PATENT DOCUMENTS

| | | |
|---|---|---|
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,780 B2 | 6/2004 | Stout et al. |
| 6,752,810 B1 | 6/2004 | Gao et al. |
| 6,752,831 B2 | 6/2004 | Sybert et al. |
| 6,755,836 B1 | 6/2004 | Lewis |
| 6,755,868 B2 | 6/2004 | Rousseau |
| 6,761,722 B2 | 7/2004 | Cole et al. |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,790,210 B1 | 9/2004 | Cragg et al. |
| 6,793,595 B1 | 9/2004 | Monnet |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,835,377 B2 | 12/2004 | Goldberg et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,887,271 B2 | 5/2005 | Justin et al. |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,911,202 B2 | 6/2005 | Amir et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,939,379 B2 | 9/2005 | Sklar |
| 6,949,102 B2 | 9/2005 | Andrews |
| 6,951,565 B2 | 10/2005 | Keane et al. |
| 6,960,214 B2 | 11/2005 | Burkinshaw |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,984,237 B2 | 1/2006 | Hatch et al. |
| 6,986,781 B2 | 1/2006 | Smith |
| 6,989,034 B2 | 1/2006 | Hammer et al. |
| 6,994,719 B2 | 2/2006 | Grafton |
| 6,994,725 B1 | 2/2006 | Goble |
| 7,001,429 B2 | 2/2006 | Ferguson |
| 7,004,959 B2 | 2/2006 | Bonutti |
| 7,008,451 B2 | 3/2006 | Justin et al. |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,083,638 B2 | 8/2006 | Foerster |
| 7,087,064 B1 | 8/2006 | Hyde |
| 7,097,654 B1 | 8/2006 | Freedland |
| 7,105,010 B2 | 9/2006 | Hart et al. |
| 7,112,221 B2 | 9/2006 | Harris |
| 7,118,578 B2 | 10/2006 | West, Jr. et al. |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,148,209 B2 | 12/2006 | Hoemann et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,285 B2 | 1/2007 | Sklar et al. |
| 7,160,333 B2 | 1/2007 | Plouhar et al. |
| 7,172,626 B1 | 2/2007 | Andrews |
| 7,179,259 B1 | 2/2007 | Gibbs |
| 7,201,722 B2 | 4/2007 | Krueger |
| 7,207,993 B1 | 4/2007 | Baldwin et al. |
| 7,255,675 B2 | 8/2007 | Gertner et al. |
| 7,255,700 B2 | 8/2007 | Kaiser et al. |
| 7,255,715 B2 | 8/2007 | Metzger |
| 7,261,716 B2 | 8/2007 | Strobel et al. |
| 7,264,634 B2 | 9/2007 | Schmieding |
| 7,279,008 B2 | 10/2007 | Brown et al. |
| 7,285,124 B2 | 10/2007 | Foerster |
| 7,291,177 B2 | 11/2007 | Gibbs |
| 7,303,577 B1 | 12/2007 | Dean |
| 7,306,417 B2 | 12/2007 | Dorstewitz |
| 7,309,355 B2 | 12/2007 | Donnelly et al. |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,468,074 B2 | 12/2008 | Caborn et al. |
| 7,481,814 B1 | 1/2009 | Metzger |
| 7,485,149 B1 | 2/2009 | White |
| 7,494,506 B2 | 2/2009 | Brulez et al. |
| D587,807 S | 3/2009 | Wolf et al. |
| 7,500,983 B1 | 3/2009 | Kaiser et al. |
| 7,513,910 B2 | 4/2009 | Buskirk et al. |
| 7,572,275 B2 | 8/2009 | Fallin et al. |
| 7,572,298 B2 | 8/2009 | Roller et al. |
| 7,578,825 B2 | 8/2009 | Huebner |
| 7,585,311 B2 | 9/2009 | Green et al. |
| 7,591,823 B2 | 9/2009 | Tipirneni |
| 7,597,705 B2 | 10/2009 | Forsberg et al. |
| 7,601,165 B2 | 10/2009 | Stone |
| 7,604,636 B1 | 10/2009 | Walters et al. |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,691,112 B2 | 4/2010 | Chanduszko et al. |
| 7,695,493 B2 | 4/2010 | Saadat et al. |
| 7,695,503 B1 | 4/2010 | Kaiser et al. |
| 7,703,372 B1 | 4/2010 | Shakespeare |
| 7,717,929 B2 | 5/2010 | Fallman |
| 7,731,732 B2 | 6/2010 | Ken |
| 7,736,364 B2 | 6/2010 | Stone |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,762,942 B2 | 7/2010 | Neisz et al. |
| 7,771,482 B1 | 8/2010 | Karmon |
| 7,776,041 B1 | 8/2010 | Walters |

(56) References Cited

U.S. PATENT DOCUMENTS

| | | |
|---|---|---|
| 7,790,945 B1 | 9/2010 | Watson, Jr. |
| 7,803,173 B2 | 9/2010 | Burkhart et al. |
| 7,819,895 B2 | 10/2010 | Ginn et al. |
| 7,828,820 B2 | 11/2010 | Stone et al. |
| 7,828,850 B2 | 11/2010 | Cauthen, III et al. |
| 7,856,698 B2 | 12/2010 | Hays |
| 7,857,830 B2 | 12/2010 | Stone et al. |
| 7,867,252 B2 | 1/2011 | Criscuolo et al. |
| 7,867,264 B2 | 1/2011 | McDevitt et al. |
| 7,875,058 B2 | 1/2011 | Holmes, Jr. |
| 7,878,058 B2 | 2/2011 | Blendinger et al. |
| 7,887,586 B2 | 2/2011 | Linares |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 | 8/2011 | Blum |
| 8,034,090 B2 | 10/2011 | Stone et al. |
| 8,062,334 B2 | 11/2011 | Green et al. |
| 8,075,574 B2 | 12/2011 | May et al. |
| 8,088,108 B2 | 1/2012 | Kraft |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,118,868 B2 | 2/2012 | May et al. |
| 8,128,658 B2 | 3/2012 | Kaiser et al. |
| 8,137,354 B2 | 3/2012 | Stone |
| 8,137,382 B2 | 3/2012 | Denham et al. |
| 8,162,997 B2 | 4/2012 | Struhl |
| 8,167,906 B2 | 5/2012 | Cauldwell et al. |
| 8,177,810 B2 | 5/2012 | Ferree |
| 8,202,318 B2 | 6/2012 | Willobee |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 8,273,106 B2 | 9/2012 | Stone et al. |
| 8,292,921 B2 | 10/2012 | Stone et al. |
| 8,298,262 B2 | 10/2012 | Stone et al. |
| 8,298,284 B2 | 10/2012 | Cassani |
| 8,303,604 B2 | 11/2012 | Stone et al. |
| 8,317,825 B2 | 11/2012 | Stone |
| 8,337,525 B2 | 12/2012 | Stone et al. |
| 8,343,155 B2 | 1/2013 | Fisher et al. |
| 8,343,227 B2 | 1/2013 | Metzger et al. |
| 8,361,054 B2 | 1/2013 | Ducharme et al. |
| 8,361,113 B2 | 1/2013 | Stone et al. |
| 8,409,253 B2 | 4/2013 | Stone et al. |
| 8,486,114 B2 | 7/2013 | Gillard et al. |
| 8,500,818 B2 | 8/2013 | Metzger et al. |
| 8,506,597 B2 | 8/2013 | Kaiser et al. |
| 8,551,140 B2 | 10/2013 | Denham et al. |
| 8,562,645 B2 | 10/2013 | Stone et al. |
| 8,562,647 B2 | 10/2013 | Kaiser et al. |
| 8,574,235 B2 | 11/2013 | Stone |
| 8,579,944 B2 | 11/2013 | Holloway et al. |
| 8,597,327 B2 | 12/2013 | Stone et al. |
| 8,608,777 B2 | 12/2013 | Kaiser et al. |
| 8,632,566 B2 | 1/2014 | Olson |
| 8,632,569 B2 | 1/2014 | Stone et al. |
| 8,652,171 B2 | 2/2014 | Stone et al. |
| 8,652,172 B2 | 2/2014 | Denham et al. |
| 8,672,904 B1 | 3/2014 | Schultz |
| 8,672,968 B2 | 3/2014 | Stone et al. |
| 8,672,969 B2 | 3/2014 | Stone et al. |
| 8,721,650 B2 | 5/2014 | Fanton et al. |
| 8,721,684 B2 | 5/2014 | Denham et al. |
| 8,771,316 B2 | 7/2014 | Denham et al. |
| 8,771,352 B2 | 7/2014 | Conner et al. |
| 8,777,956 B2 | 7/2014 | Hoeppner et al. |
| 8,801,783 B2 | 8/2014 | Stone et al. |
| 8,840,645 B2 | 9/2014 | Denham et al. |
| 8,900,314 B2 | 12/2014 | Metzger et al. |
| 8,926,613 B2 | 1/2015 | Kaiser et al. |
| 8,932,331 B2 | 1/2015 | Kaiser et al. |
| 8,936,621 B2 | 1/2015 | Denham et al. |
| 8,968,364 B2 | 3/2015 | Berelsman |
| 8,998,949 B2 | 4/2015 | Stone et al. |
| 9,005,287 B2 | 4/2015 | Stone |
| 9,017,381 B2 | 4/2015 | Kaiser et al. |
| 9,023,058 B2 | 5/2015 | Jaramillo et al. |
| 9,078,644 B2 | 7/2015 | Stone |
| 9,149,267 B2 | 10/2015 | Norton et al. |
| 9,173,651 B2 | 11/2015 | Stone et al. |
| 9,198,673 B2 | 12/2015 | Stone |
| 9,216,078 B2 | 12/2015 | Conner et al. |
| 9,271,713 B2 | 3/2016 | Denham et al. |
| 9,314,241 B2 | 4/2016 | Stone et al. |
| 9,357,991 B2 | 6/2016 | Denham et al. |
| 9,357,992 B2 | 6/2016 | Stone et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0029387 A1 | 10/2001 | Wolf et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051815 A1 | 12/2001 | Esplin |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0068254 A1 | 6/2002 | Campbell |
| 2002/0077629 A1 | 6/2002 | Hoffman et al. |
| 2002/0077659 A1 | 6/2002 | Johnson et al. |
| 2002/0082220 A1 | 6/2002 | Hoemann et al. |
| 2002/0099411 A1 | 7/2002 | Bartlett |
| 2002/0111591 A1 | 8/2002 | Mckinnon et al. |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0156475 A1 | 10/2002 | Lerch et al. |
| 2002/0161401 A1 | 10/2002 | Steiner |
| 2002/0161439 A1 | 10/2002 | Strobel et al. |
| 2002/0165548 A1 | 11/2002 | Jutley |
| 2002/0165611 A1 | 11/2002 | Enzerink et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0177853 A1 | 11/2002 | Chervitz et al. |
| 2002/0188298 A1 | 12/2002 | Chan |
| 2002/0193830 A1 | 12/2002 | Bonutti |
| 2003/0004545 A1 | 1/2003 | Burkhart et al. |
| 2003/0009235 A1 | 1/2003 | Manrique et al. |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |

(56) References Cited

U.S. PATENT DOCUMENTS

| | | |
|---|---|---|
| 2003/0036801 A1 | 2/2003 | Schwartz et al. |
| 2003/0065391 A1 | 4/2003 | Re et al. |
| 2003/0065402 A1 | 4/2003 | Anderson et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130670 A1 | 7/2003 | Anderson et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0139752 A1 | 7/2003 | Pasricha et al. |
| 2003/0139775 A1 | 7/2003 | Grafton |
| 2003/0149448 A1 | 8/2003 | Foerster et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0176920 A1 | 9/2003 | Sklar et al. |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208209 A1 | 11/2003 | Gambale et al. |
| 2003/0208210 A1 | 11/2003 | Dreyfuss et al. |
| 2003/0212456 A1 | 11/2003 | Lipchitz et al. |
| 2003/0216809 A1 | 11/2003 | Ferguson |
| 2003/0220646 A1 | 11/2003 | Thelen et al. |
| 2003/0220660 A1 | 11/2003 | Kortenbach et al. |
| 2003/0225459 A1 | 12/2003 | Hammer et al. |
| 2003/0229361 A1 | 12/2003 | Jackson |
| 2003/0229396 A1 | 12/2003 | Andrews |
| 2003/0236555 A1 | 12/2003 | Thornes |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0039389 A1 | 2/2004 | West et al. |
| 2004/0044391 A1 | 3/2004 | Porter |
| 2004/0059357 A1 | 3/2004 | Koseki |
| 2004/0073176 A1 | 4/2004 | Utterberg |
| 2004/0087981 A1 | 5/2004 | Berube et al. |
| 2004/0092936 A1 | 5/2004 | Miller et al. |
| 2004/0093031 A1 | 5/2004 | Burkhart et al. |
| 2004/0093032 A1 | 5/2004 | Sinnott et al. |
| 2004/0098051 A1 | 5/2004 | Fallin et al. |
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0127907 A1 | 7/2004 | Dakin et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0181234 A1 | 9/2004 | McDevitt et al. |
| 2004/0182968 A1 | 9/2004 | Gentry |
| 2004/0187314 A1 | 9/2004 | Johnson |
| 2004/0193185 A1 | 9/2004 | McBrayer |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225183 A1 | 11/2004 | Michlitsch et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243180 A1 | 12/2004 | Donnelly et al. |
| 2004/0243235 A1 | 12/2004 | Goh et al. |
| 2004/0249394 A1 | 12/2004 | Morris et al. |
| 2004/0260296 A1 | 12/2004 | Kaiser et al. |
| 2004/0260298 A1 | 12/2004 | Kaiser et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2004/0267317 A1 | 12/2004 | Higgins et al. |
| 2004/0267361 A1 | 12/2004 | Donnelly et al. |
| 2004/0267362 A1 | 12/2004 | Hwang et al. |
| 2005/0004670 A1 | 1/2005 | Gebhardt et al. |
| 2005/0021087 A1 | 1/2005 | Koseki |
| 2005/0021148 A1 | 1/2005 | Gibbs |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0049598 A1 | 3/2005 | West, Jr. et al. |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0065526 A1 | 3/2005 | Drew et al. |
| 2005/0070906 A1 | 3/2005 | Clark et al. |
| 2005/0070928 A1 | 3/2005 | Heino et al. |
| 2005/0074495 A1 | 4/2005 | Schwartz et al. |
| 2005/0076478 A1 | 4/2005 | Miyazaki et al. |
| 2005/0085819 A1 | 4/2005 | Ellis et al. |
| 2005/0090827 A1 | 4/2005 | Gedebou |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0107882 A1 | 5/2005 | Stone et al. |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0130301 A1 | 6/2005 | Mckay et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149118 A1 | 7/2005 | Koyfman et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0171547 A1 | 8/2005 | Aram |
| 2005/0171603 A1 | 8/2005 | Justin et al. |
| 2005/0171604 A1 | 8/2005 | Michalow |

(56) References Cited

U.S. PATENT DOCUMENTS

| | | |
|---|---|---|
| 2005/0177237 A1 | 8/2005 | Shappley et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0192632 A1 | 9/2005 | Geissler et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251153 A1 | 11/2005 | Sakamoto et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0261642 A1 | 11/2005 | Weston |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004364 A1 | 1/2006 | Green et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0015107 A1 | 1/2006 | Sklar |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052787 A1 | 3/2006 | Re et al. |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0095130 A1 | 5/2006 | Caborn et al. |
| 2006/0095131 A1 | 5/2006 | Justin et al. |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122608 A1 | 6/2006 | Fallin et al. |
| 2006/0122611 A1 | 6/2006 | Morales et al. |
| 2006/0135958 A1 | 6/2006 | Marissen et al. |
| 2006/0149258 A1 | 7/2006 | Sousa |
| 2006/0149266 A1 | 7/2006 | Cordasco |
| 2006/0155287 A1 | 7/2006 | Montgomery et al. |
| 2006/0155328 A1 | 7/2006 | Foerster |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0178743 A1 | 8/2006 | Carter |
| 2006/0189993 A1 | 8/2006 | Stone |
| 2006/0190042 A1 | 8/2006 | Stone et al. |
| 2006/0195101 A1 | 8/2006 | Stevens |
| 2006/0195106 A1 | 8/2006 | Jones et al. |
| 2006/0200235 A1 | 9/2006 | Bianchi et al. |
| 2006/0212055 A1 | 9/2006 | Karabey et al. |
| 2006/0229623 A1 | 10/2006 | Bonutti et al. |
| 2006/0229671 A1 | 10/2006 | Steiner et al. |
| 2006/0229676 A1 | 10/2006 | Doll et al. |
| 2006/0235407 A1 | 10/2006 | Wang et al. |
| 2006/0235413 A1 | 10/2006 | Denham et al. |
| 2006/0241624 A1 | 10/2006 | Kizuka et al. |
| 2006/0241776 A1 | 10/2006 | Brown et al. |
| 2006/0241781 A1 | 10/2006 | Brown et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0259076 A1* | 11/2006 | Burkhart ............ A61B 17/0401 606/228 |
| 2006/0264944 A1 | 11/2006 | Cole |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0276896 A1 | 12/2006 | Fallin et al. |
| 2006/0280768 A1 | 12/2006 | Hwang et al. |
| 2006/0280803 A1 | 12/2006 | Kumar et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005068 A1 | 1/2007 | Sklar |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0027476 A1 | 2/2007 | Harris et al. |
| 2007/0032800 A1 | 2/2007 | Ortiz et al. |
| 2007/0032823 A1 | 2/2007 | Tegg |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0071568 A1 | 3/2007 | Dorstewitz |
| 2007/0073307 A1 | 3/2007 | Scribner et al. |
| 2007/0073319 A1 | 3/2007 | Mikkaichi et al. |
| 2007/0073322 A1 | 3/2007 | Mikkaichi et al. |
| 2007/0078435 A1 | 4/2007 | Stone et al. |
| 2007/0083236 A1 | 4/2007 | Sikora et al. |
| 2007/0088362 A1 | 4/2007 | Bonutti et al. |
| 2007/0093847 A1 | 4/2007 | Scribner et al. |
| 2007/0100350 A1 | 5/2007 | Deffenbaugh et al. |
| 2007/0112384 A1 | 5/2007 | Conlon et al. |
| 2007/0118217 A1 | 5/2007 | Brulez et al. |
| 2007/0123883 A1 | 5/2007 | Ellis et al. |
| 2007/0123984 A1 | 5/2007 | Hodorek |
| 2007/0129809 A1 | 6/2007 | Meridew et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0167926 A1 | 7/2007 | Blott et al. |
| 2007/0167950 A1 | 7/2007 | Tauro et al. |
| 2007/0173948 A1 | 7/2007 | Meridew et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0198022 A1 | 8/2007 | Lang et al. |
| 2007/0198036 A1 | 8/2007 | Sklar et al. |
| 2007/0219558 A1 | 9/2007 | Deutsch |
| 2007/0225715 A1 | 9/2007 | Deffenbaugh et al. |
| 2007/0225719 A1* | 9/2007 | Stone ................. A61B 17/0401 606/232 |
| 2007/0225805 A1 | 9/2007 | Schmieding |
| 2007/0233241 A1 | 10/2007 | Graf et al. |
| 2007/0239209 A1 | 10/2007 | Fallman |
| 2007/0239275 A1 | 10/2007 | Willobee |
| 2007/0244565 A1 | 10/2007 | Stchur |
| 2007/0250059 A1 | 10/2007 | Weisshaupt et al. |
| 2007/0250163 A1 | 10/2007 | Cassani |
| 2007/0250175 A1 | 10/2007 | Meridew et al. |
| 2007/0260251 A1 | 11/2007 | Weier et al. |
| 2007/0260279 A1 | 11/2007 | Hotter et al. |
| 2007/0265704 A1 | 11/2007 | Mayer et al. |
| 2007/0270856 A1 | 11/2007 | Morales et al. |
| 2007/0270878 A1 | 11/2007 | Leisinger |

(56) References Cited

U.S. PATENT DOCUMENTS

| | | |
|---|---|---|
| 2007/0276387 A1 | 11/2007 | Morales et al. |
| 2007/0288023 A1 | 12/2007 | Pellegrino et al. |
| 2008/0027430 A1 | 1/2008 | Montgomery et al. |
| 2008/0027440 A1 | 1/2008 | Marissen et al. |
| 2008/0027446 A1 | 1/2008 | Stone et al. |
| 2008/0033549 A1 | 2/2008 | Marshall et al. |
| 2008/0046009 A1 | 2/2008 | Albertorio et al. |
| 2008/0051836 A1 | 2/2008 | Foerster et al. |
| 2008/0058787 A1 | 3/2008 | Gertner |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0097430 A1 | 4/2008 | Bernstein et al. |
| 2008/0114460 A1 | 5/2008 | Willobee et al. |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0133007 A1 | 6/2008 | Donnelly et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0147187 A1 | 6/2008 | Bollinger et al. |
| 2008/0154260 A1 | 6/2008 | Hoof |
| 2008/0154314 A1 | 6/2008 | McDevitt |
| 2008/0161806 A1 | 7/2008 | Donnelly et al. |
| 2008/0161852 A1 | 7/2008 | Kaiser et al. |
| 2008/0161861 A1 | 7/2008 | Huebner |
| 2008/0161864 A1 | 7/2008 | Beck et al. |
| 2008/0166421 A1 | 7/2008 | Buhr et al. |
| 2008/0172097 A1 | 7/2008 | Lerch et al. |
| 2008/0177302 A1 | 7/2008 | Shurnas |
| 2008/0183290 A1 | 7/2008 | Baird et al. |
| 2008/0188933 A1 | 8/2008 | Koob et al. |
| 2008/0188936 A1 | 8/2008 | Ball et al. |
| 2008/0208252 A1 | 8/2008 | Holmes |
| 2008/0217263 A1 | 9/2008 | Higgins et al. |
| 2008/0221527 A1 | 9/2008 | Bradley et al. |
| 2008/0221578 A1 | 9/2008 | Zeitani |
| 2008/0228186 A1 | 9/2008 | Gall et al. |
| 2008/0234730 A1 | 9/2008 | Cotton et al. |
| 2008/0255613 A1 | 10/2008 | Kaiser et al. |
| 2008/0257363 A1 | 10/2008 | Schoenefeld et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0281428 A1 | 11/2008 | Meyers et al. |
| 2008/0300611 A1 | 12/2008 | Houser et al. |
| 2008/0312689 A1 | 12/2008 | Denham et al. |
| 2008/0319478 A1 | 12/2008 | Foerster et al. |
| 2009/0018589 A1 | 1/2009 | Smisson, III et al. |
| 2009/0018655 A1 | 1/2009 | Brunelle et al. |
| 2009/0043342 A1 | 2/2009 | Freedland |
| 2009/0054928 A1 | 2/2009 | Denham et al. |
| 2009/0062847 A1 | 3/2009 | Ken |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0084491 A1 | 4/2009 | Uthgenannt et al. |
| 2009/0099598 A1 | 4/2009 | McDevitt et al. |
| 2009/0105717 A1 | 4/2009 | Bluechel |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0216325 A1 | 8/2009 | May et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0265015 A1 | 10/2009 | May et al. |
| 2009/0287215 A1 | 11/2009 | Fisher et al. |
| 2009/0299409 A1 | 12/2009 | Coe et al. |
| 2009/0306711 A1 | 12/2009 | Stone et al. |
| 2009/0312776 A1 | 12/2009 | Kaiser et al. |
| 2009/0312793 A1 | 12/2009 | Huxel et al. |
| 2009/0318960 A1 | 12/2009 | Burkhart |
| 2009/0318961 A1 | 12/2009 | Stone et al. |
| 2010/0016899 A1 | 1/2010 | Gelfand |
| 2010/0042114 A1 | 2/2010 | Schaffhausen |
| 2010/0063541 A1 | 3/2010 | Brunelle et al. |
| 2010/0087857 A1 | 4/2010 | Stone et al. |
| 2010/0094355 A1 | 4/2010 | Trenhaile |
| 2010/0106254 A1 | 4/2010 | Delsignore |
| 2010/0121348 A1 | 5/2010 | Van Der et al. |
| 2010/0145384 A1 | 6/2010 | Stone et al. |
| 2010/0152752 A1 | 6/2010 | Denove et al. |
| 2010/0191342 A1 | 7/2010 | Byrd et al. |
| 2010/0204700 A1 | 8/2010 | Falahee |
| 2010/0211071 A1 | 8/2010 | Lettmann et al. |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0305709 A1 | 12/2010 | Metzger et al. |
| 2010/0312341 A1 | 12/2010 | Kaiser et al. |
| 2011/0009885 A1 | 1/2011 | Graf et al. |
| 2011/0022083 A1 | 1/2011 | DiMatteo et al. |
| 2011/0026141 A1 | 2/2011 | Barrows |
| 2011/0046733 A1 | 2/2011 | Eggli |
| 2011/0087225 A1 | 4/2011 | Fritzinger |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0112537 A1 | 5/2011 | Bernstein et al. |
| 2011/0112538 A1 | 5/2011 | Dell'Oca |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0245868 A1 | 10/2011 | Teeslink et al. |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0004669 A1 | 1/2012 | Overes et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0059468 A1 | 3/2012 | Mattern et al. |
| 2012/0089193 A1 | 4/2012 | Stone et al. |
| 2012/0095470 A1 | 4/2012 | Kaiser et al. |
| 2012/0109156 A1 | 5/2012 | Overes et al. |
| 2012/0116409 A1 | 5/2012 | Stone |
| 2012/0116450 A1 | 5/2012 | McDevitt et al. |
| 2012/0116452 A1 | 5/2012 | Stone et al. |
| 2012/0123447 A1 | 5/2012 | Corrao et al. |
| 2012/0123474 A1 | 5/2012 | Zajac et al. |
| 2012/0123541 A1 | 5/2012 | Albertorio et al. |
| 2012/0143215 A1 | 6/2012 | Corrao et al. |
| 2012/0150223 A1 | 6/2012 | Manos et al. |
| 2012/0150297 A1 | 6/2012 | Denham et al. |

(56) References Cited

U.S. PATENT DOCUMENTS

| | | |
|---|---|---|
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |
| 2012/0215257 A1 | 8/2012 | McDevitt et al. |
| 2012/0245585 A1 | 9/2012 | Kaiser et al. |
| 2012/0265219 A1 | 10/2012 | Rushdy et al. |
| 2012/0290003 A1 | 11/2012 | Dreyfuss |
| 2012/0290004 A1 | 11/2012 | Lombardo et al. |
| 2012/0296427 A1 | 11/2012 | Conner et al. |
| 2012/0310245 A1 | 12/2012 | Hoeppner et al. |
| 2013/0018375 A1 | 1/2013 | Dell'Oca |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0035722 A1 | 2/2013 | McDevitt et al. |
| 2013/0046341 A1 | 2/2013 | Stone et al. |
| 2013/0103082 A1 | 4/2013 | Kaiser et al. |
| 2013/0110165 A1 | 5/2013 | Burkhart et al. |
| 2013/0110251 A1 | 5/2013 | Metzger et al. |
| 2013/0116730 A1 | 5/2013 | Denham et al. |
| 2013/0123810 A1 | 5/2013 | Brown et al. |
| 2013/0123813 A1 | 5/2013 | Stone et al. |
| 2013/0131722 A1 | 5/2013 | Marchand et al. |
| 2013/0138123 A1 | 5/2013 | Stone et al. |
| 2013/0144337 A1 | 6/2013 | Stone et al. |
| 2013/0144338 A1 | 6/2013 | Stone et al. |
| 2013/0158601 A1 | 6/2013 | Stone et al. |
| 2013/0190818 A1 | 7/2013 | Norton |
| 2013/0190819 A1 | 7/2013 | Norton |
| 2013/0204276 A1 | 8/2013 | Stone et al. |
| 2013/0211452 A1 | 8/2013 | Stone et al. |
| 2013/0237997 A1 | 9/2013 | Arai et al. |
| 2013/0245761 A1 | 9/2013 | Conner et al. |
| 2013/0274812 A1 | 10/2013 | Dell'Oca |
| 2013/0289564 A1 | 10/2013 | Bernstein et al. |
| 2013/0317621 A1 | 11/2013 | Metzger et al. |
| 2013/0331848 A1 | 12/2013 | Kaiser et al. |
| 2014/0046367 A1 | 2/2014 | Stone et al. |
| 2014/0046368 A1 | 2/2014 | Kaiser et al. |
| 2014/0067081 A1 | 3/2014 | Stone |
| 2014/0088655 A1 | 3/2014 | Stone et al. |
| 2014/0094913 A1 | 4/2014 | Berelsman et al. |
| 2014/0135835 A1 | 5/2014 | Stone et al. |
| 2014/0163613 A1 | 6/2014 | Stone et al. |
| 2014/0163614 A1 | 6/2014 | Denham et al. |
| 2014/0200583 A1 | 7/2014 | Stone et al. |
| 2014/0257378 A1 | 9/2014 | Norton et al. |
| 2014/0276992 A1 | 9/2014 | Stone et al. |
| 2014/0277447 A1 | 9/2014 | Berelsman et al. |
| 2014/0324101 A1 | 10/2014 | Denham et al. |
| 2014/0330311 A1 | 11/2014 | Denham et al. |
| 2014/0350674 A1 | 11/2014 | Stone et al. |
| 2015/0012094 A1 | 1/2015 | Denham et al. |
| 2015/0057757 A1 | 2/2015 | Metzger et al. |
| 2015/0119890 A1 | 4/2015 | Kaiser et al. |
| 2015/0127051 A1 | 5/2015 | Kaiser et al. |
| 2015/0134000 A1 | 5/2015 | Denham et al. |
| 2015/0173887 A1 | 6/2015 | Berelsman et al. |
| 2015/0257750 A1 | 9/2015 | Kaiser et al. |
| 2016/0000483 A1 | 1/2016 | Stone |
| 2016/0022261 A1 | 1/2016 | Stone et al. |
| 2016/0058436 A1 | 3/2016 | Stone et al. |
| 2016/0081789 A1 | 3/2016 | Denham et al. |
| 2016/0106414 A1 | 4/2016 | Stone et al. |
| 2016/0128684 A1 | 5/2016 | Stone et al. |

FOREIGN PATENT DOCUMENTS

| | | | |
|---|---|---|---|
| AU | 4381268 A | | 4/1970 |
| AU | 5850469 | | 1/1971 |
| AU | 5963869 | | 2/1971 |
| AU | 1505470 | | 11/1971 |
| AU | 2223767 | | 5/1973 |
| AU | 3615171 | | 5/1973 |
| AU | 440266 B2 | | 9/1973 |
| AU | 5028569 | | 9/1973 |
| AU | 7110887 | | 10/1987 |
| AU | 639410 | | 11/1989 |
| AU | 639410 A | | 11/1989 |
| AU | 1713188 A | | 11/1989 |
| AU | 651929 | | 8/1994 |
| AU | 651929 B2 | | 8/1994 |
| CN | 105208970 A | | 12/2015 |
| DE | 2529669 | | 3/1976 |
| DE | 2747312 | | 4/1979 |
| DE | 2818254 | | 10/1979 |
| DE | 2919009 | | 11/1979 |
| DE | 3027138 | | 12/1981 |
| DE | 3225620 | | 2/1983 |
| DE | 3136083 | | 3/1983 |
| DE | 233303 C | | 2/1986 |
| DE | 4127550 | | 2/1993 |
| DE | 4302397 | | 7/1993 |
| DE | 29621340 | | 5/1998 |
| DE | 19841252 | | 3/2000 |
| DE | 29922088 U1 | | 4/2000 |
| DE | 20207781 U1 | | 8/2002 |
| EP | 19062 A1 | | 11/1980 |
| EP | 0108912 | | 5/1984 |
| EP | 0129422 | | 12/1984 |
| EP | 0129442 | | 12/1984 |
| EP | 0172130 | | 2/1986 |
| EP | 0241240 | | 10/1987 |
| EP | 0241792 | | 10/1987 |
| EP | 0260970 | | 3/1988 |
| EP | 0270704 | | 6/1988 |
| EP | 0282789 | | 9/1988 |
| EP | 0315371 | | 5/1989 |
| EP | 0317406 | | 5/1989 |
| EP | 0340159 | | 11/1989 |
| EP | 0346183 | | 12/1989 |
| EP | 0349173 | | 1/1990 |
| EP | 0374088 | | 6/1990 |
| EP | 0409364 | | 1/1991 |
| EP | 0415915 | | 3/1991 |
| EP | 0440991 | | 8/1991 |
| EP | 440991 A1 | | 8/1991 |
| EP | 0441065 | | 8/1991 |
| EP | 0447065 A2 | | 9/1991 |
| EP | 0451932 | | 10/1991 |
| EP | 0464480 | | 1/1992 |
| EP | 0490417 | | 6/1992 |
| EP | 0497079 | | 8/1992 |
| EP | 0502509 | | 9/1992 |
| EP | 0502698 | | 9/1992 |
| EP | 520177 | | 12/1992 |
| EP | 0546726 | | 6/1993 |
| EP | 0574707 | | 12/1993 |
| EP | 0582514 | | 2/1994 |
| EP | 0591991 | | 4/1994 |
| EP | 0598219 | | 5/1994 |
| EP | 0611551 A1 | | 8/1994 |
| EP | 0627203 | | 12/1994 |
| EP | 0651979 | | 5/1995 |
| EP | 0669110 | | 8/1995 |
| EP | 0686373 | | 12/1995 |
| EP | 0702933 | | 3/1996 |
| EP | 0775473 | | 5/1997 |
| EP | 0913123 | | 5/1999 |
| EP | 0913131 | | 5/1999 |
| EP | 99121106 | | 10/1999 |
| EP | 991210527 | | 10/1999 |
| EP | 0995409 | | 4/2000 |
| EP | 1013229 | | 6/2000 |
| EP | 1093773 | | 4/2001 |
| EP | 1093774 | | 4/2001 |
| EP | 1555945 | | 7/2005 |
| EP | 1741412 A2 | | 1/2007 |
| EP | 1864617 A2 | | 12/2007 |
| EP | 2238944 A2 | | 10/2010 |
| EP | 2544607 A1 | | 1/2013 |

(56) References Cited

FOREIGN PATENT DOCUMENTS

| | | |
|---|---|---|
| EP | 2709557 A1 | 3/2014 |
| EP | 2934379 | 10/2015 |
| FR | 2622790 | 5/1989 |
| FR | 2634373 A1 | 1/1990 |
| FR | 2655840 | 6/1991 |
| FR | 2663837 A1 | 1/1992 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2734709 A1 | 12/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2129306 A | 5/1984 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 54166092 U | 11/1979 |
| JP | 54166093 U | 11/1979 |
| JP | 54176284 U | 12/1979 |
| JP | 54178988 U | 12/1979 |
| JP | 62159647 | 7/1987 |
| JP | 62159647 U | 10/1987 |
| JP | 62295657 | 12/1987 |
| JP | 5269160 | 10/1993 |
| JP | 5300917 | 11/1993 |
| JP | 751292 | 2/1995 |
| JP | 10127672 A | 5/1998 |
| JP | 10211213 | 8/1998 |
| JP | 5362912 B2 | 12/2013 |
| RU | 2051647 C1 | 1/1996 |
| RU | 2076667 C1 | 4/1997 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9609797 A1 | 4/1996 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9937219 A1 | 7/1999 |
| WO | WO-9944544 | 9/1999 |
| WO | WO-9952472 A1 | 10/1999 |
| WO | WO-0004159 A1 | 1/2000 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-03092551 A1 | 11/2003 |
| WO | WO-2004091412 A1 | 10/2004 |
| WO | WO-2005104992 A1 | 11/2005 |
| WO | WO-2005122954 | 12/2005 |
| WO | WO-2005122954 A1 | 12/2005 |
| WO | WO-2006023661 A2 | 3/2006 |
| WO | WO-2006023661 A2 | 3/2006 |
| WO | WO-2006055823 A2 | 5/2006 |
| WO | WO-2007045460 A2 | 4/2007 |
| WO | WO-2007103562 A2 | 9/2007 |
| WO | WO-2007109280 A2 | 9/2007 |
| WO | WO-2007119057 A1 | 10/2007 |
| WO | WO-2008002550 A2 | 1/2008 |
| WO | WO-2008015171 A1 | 2/2008 |
| WO | WO-2008073588 A2 | 6/2008 |
| WO | WO-2009012021 A1 | 1/2009 |
| WO | WO-2009131820 A1 | 10/2009 |
| WO | WO-2010138832 A1 | 12/2010 |
| WO | WO-2011112371 A1 | 9/2011 |
| WO | WO-2011150238 A1 | 12/2011 |
| WO | WO-2012134999 A1 | 10/2012 |
| WO | WO-2012158583 A1 | 11/2012 |
| WO | WO-2013066974 A1 | 5/2013 |
| WO | WO-2013074525 A1 | 5/2013 |
| WO | WO-2014/100109 A1 | 6/2014 |
| WO | WO-2014151766 A1 | 9/2014 |

OTHER PUBLICATIONS

"ToggleLoc™ Fixation Device with ZipLoop™ Technology: ACL Reconstruction Bone-Tendon-Bone," by James R. Andrews, M.D., of Biomet Sports Medicine, a Biomet Company Brochure (2013), pp. 1-20.

International Preliminary Report on Patentability and Written Opinion mailed May 30, 2014 for PCT/US2012/064832 which claims benefit of U.S. Appl. No. 13/295,126, filed Nov. 14, 2011.

International Search Report and Written Opinion mailed Jun. 6, 2014 for PCT/US2014/026413 which claims benefit of U.S. Appl. No. 14/095,614, filed Dec. 3, 2013 and U.S. Appl. No. 14/095,639, filed Dec. 3, 2013.

ToggleLoc Fixation Device with ZipLoop Technology: Biceps Tendon Reattachment by Mark J. Albritton, M.D. and Daniel Worrel, M.D. of Biomet Sports Medicine, a Biomet Company Brochure (2099, 2011), pp. 1-12.

"AperFix® System Surgical Technique Guide. Single Tunnel Double Bundle.™" Cayenne Medical brochure. (Aug. 2008) 8 sheets.

"Arthroscopic Meniscal Repair using the Meniscal Cinch™", Surgical Technique brochure. (2008) Arthrex® 6 sheets.

"Bio-Intrafix (TCP/PLA & Intrafix, Tibial Soft Tissue Fasteners," by DePuy Mitek, 6 sheets, (date unknown).

"Bio-Intrafix Tibial Soft Tissue Fasteners, Building on the Legacy of IntraFix," brochure. DePuy Mitek,(Feb. 2007) 6 sheets.

"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.

"Do your next distal tendon repair with . . . The Lubbers Technique", Teno Fix® brochure, 2003 (2 pages) Ortheon® Medical.

"EZ Loc Femoral Fixation Device," copyright 2005 Arthrotek, Inc. (8 sheets).

"JuggerKnot™ Soft Anchor Midfoot Repair," brochure. Biomet Sports Medicine (Jul. 2011) 12 sheets.

"JuggerKnot™ Soft Anchor. It's Small. It's strong. And it's all suture . . . " Ordering Information brochure. Biomet Sports Medicine (Jun. 2011) 2 sheets.

"JuggerKnot™ Soft Anchor. Labral Repair," brochure. Biomet Sports Medicine (Apr. 2011) 12 sheets.

"Make your next tendon repair an open-and-shut case. The Teno Fix® Tendon Repair System", Teno Fix® brochure, 2003 (2 pages) Ortheon® Medical.

(56) References Cited

OTHER PUBLICATIONS

"PANALOK Anchor with PDS II and ETHIBOND Suture", Mitek Products ETHICON, 1997.
"SE Graft Tensioning System Surgical Technique," Linvatec Corporation copyright 2003, 2004.
"Suture Tensioner w/Tensiometer," Arthrex®, Inc. catalog "Next Generation in Knee Ligament Reconstruction & Repair Technology," 2009.
"Technique for ACL Reconstruction with Acufex Director Drill Guide and Endobutton CL," by Thomas D. Roseberg, copyright 1999 Smith & Nephew.
"TriTis™ Tibial Fixation System and Implant" brochure. Scandius Biomedical (2006).
A. Weiler, et al; Biodegradierbare Interferenzschrauben in der Kreuzbandchirurgie; OP-Journal 14 pp. 278-284; (Mar. 1998).
Arthrotek, A Biomet Company; Knees; Sure fire Hybrid Meniscal Device. (2005).
Arthrotek, A Biomet Company; Sure fire Hybrid Meniscal Device; Launch Date: Fall AANA 2004.
F. Alan Barber, M.D., "Uses and Abuses of Sutures and Anchors," Shoulder Scope, San Diego Shoulder Arthroscopy Library. http://www.shoulder.com/bass_barber.html Printed May 19, 2005.
F. Alan Barber, M.D., "Using Sutures and Anchors," San Diego Shoulder Arthroscopy Course, 17th Annual Meeting. (Jun. 14, 2000).
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
International Preliminary Report on Patentability and Written Opinion mailed Nov. 28, 2013 for PCT/US2012/037703, which claims benefit of U.S. Appl. No. 13/109,672, filed May 17, 2011,and U.S. Appl. No. 13/109,667, filed May 17, 2011.
International Preliminary Report on Patentability mailed Dec. 6, 2012 for PCT/US2011/038188 claiming benefit of U.S. Appl. No. 12/788,966, filed May 27, 2010.
International Preliminary Report on Patentability mailed Sep. 20, 2012 for PCT/US2011/026349 which claims benefit of U.S. Appl. No. 12/719,337, filed Mar. 8, 2010.
International Search Report and Written Opinion mailed Feb. 6, 2013 for PCT/US2012/064832 which claims benefit of U.S. Appl. No. 13/295,126, filed Nov. 14, 2011.
International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.
International Search Report and Written Opinion mailed Mar. 6, 2013 for PCT/US2012/062738 which claims benefit of U.S. Appl. No. 13/288,459, filed Nov. 3, 2011.
International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.
International Search Report and Written Opinion mailed Sep. 21, 2012 for PCT/US2012/037703 filed May 14, 2012 claiming benefit of U.S. Appl. No. 13/109,667, filed May 17, 2011 and U.S. Appl. No. 13/109,672, filed May 17, 2011.
Interview Summary mailed Nov. 27, 2012 for U.S. Appl. No. 13/098,897.
Interview Summary mailed Jul. 14, 2011 for U.S. Appl. No. 12/196,407.
Interview Summary mailed Jul. 14, 2011 for U.S. Appl. No. 12/196,410.
Interview Summary mailed Jul. 14, 2011 for U.S. Appl. No. 12/196,410, filed Aug. 22, 2008.
Interview Summary mailed Jun. 20, 2011 for U.S. Appl. No. 12/196,405.
Invitation to Pay Additional Fees mailed Aug. 5, 2011 for PCT/US2011/038188 claiming benefit of U.S. Appl. No. 12/788,973, filed May 27, 2010 and U.S. Appl. No. 12/788,966, filed May 27, 2010.
Invitation to Pay Additional Fees mailed Jul. 19, 2012, for PCT/US2012/037703 claiming benefit of U.S. Appl. No. 13/109,667, filed May 7, 2011.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Notice of Allowance (Supplemental Notice of Allowability) mailed Apr. 15, 2011 for U.S. Appl. No. 12/196,398, filed Aug. 22, 2008; now U.S. Pat. No. 7,959,650.
Notice of Allowance (Supplemental Notice of Allowability) mailed Mar. 9, 2011 for U.S. Appl. No. 12/196,398, filed Aug. 22, 2008; now U.S. Pat. No. 7,959,650.
Notice of Allowance mailed Oct. 7, 2013 for U.S. Appl. No. 12/702,067.
Notice of Allowance mailed Oct. 13, 2011 for U.S. Appl. No. 12/196,410.
Notice of Allowance mailed Oct. 24, 2013 for U.S. Appl. No. 13/412,127.
Notice of Allowance mailed Oct. 26, 2011 for U.S. Appl. No. 12/196,405.
Notice of Allowance mailed Oct. 26, 2011 for U.S. Appl. No. 12/196,407.
Notice of Allowance mailed Mar. 22, 2012 for U.S. Appl. No. 13/102,182.
Notice of Allowance mailed Jun. 1, 2009 for U.S. Appl. No. 11/541,506.
Notice of Allowance mailed Sep. 18, 2009 for U.S. Appl. No. 11/541,505.
Notice of Allowance mailed Jun. 1, 2009 for U.S. Appl. No. 11/541,506, filed Sep. 29, 2006; now U.S. Pat. No. 7,601,165.
Notice of Allowance with Interview Summary mailed Aug. 31, 2011 for U.S. Appl. No. 12/474,802, filed Nov. 3, 2010.
Notice of Allowance with Interview Summary mailed Feb. 3, 2011 for U.S. Appl. No. 12/196,398, filed Aug. 22, 2010; now U.S. Pat. No. 7,959,650.
Office Action from the U.S. Patent Office mailed Mar. 5, 2013 for U.S. Appl. No. 12/702,067.
Office Action from the U.S. Patent Office mailed Mar. 13, 2013 for U.S. Appl. No. 13/181,729.
Office Action from the U.S. Patent Office mailed Mar. 20, 2013 for U.S. Appl. No. 13/399,125.
Office Action from the U.S. Patent Office mailed May 22, 2013 for U.S. Appl. No. 13/098,927.
Office Action from the U.S. Patent Office mailed Jul. 15, 2013 for U.S. Appl. No. 13/587,374.
Office Action from the U.S. Patent Office mailed Aug. 7, 2013 for U.S. Appl. No. 13/412,127.
Office Action from the U.S. Patent Office mailed Sep. 11, 2013 for U.S. Appl. No. 13/412,116.
Office Action mailed Oct. 24, 2012 for U.S. Appl. No. 13/399,125.
Office Action mailed Dec. 7, 2011 for U.S. Appl. No. 12/589,168.
Office Action mailed Dec. 13, 2013 for U.S. Appl. No. 13/412,105.
Office Action mailed Sep. 21, 2012 for U.S. Appl. No. 13/098,897.
Office Action mailed Sep. 24, 2012 for U.S. Appl. No. 13/098,927.
Office Action mailed Apr. 11, 2011 for U.S. Appl. No. 12/196,405.
Office Action mailed May 19, 2009 for U.S. Appl. No. 11/541,505, filed Sep. 29, 2006; now U.S. Pat. No. 7,658,751.
Office Action mailed May 4, 2011 for U.S. Appl. No. 12/196,407, filed Aug. 22, 2008.
Office Action mailed May 9, 2011 for U.S. Appl. No. 12/196,410, filed Aug. 22, 2008.
Office Action mailedOct. 2, 2012 for U.S. Appl. No. 13/181,729.

(56) References Cited

OTHER PUBLICATIONS

Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Pioneer® Sternal Cable System (2010).
Rapid Sternal Closure (2006) KLS Martin L.P. http://www.rapidsternalclosure.com/medical/demo.php Web accessed Sep. 8, 2008.
Restriction Requirement mailed Mar. 22, 2011 for U.S. Appl. No. 12/196,407, filed Aug. 22, 2008.
Restriction Requirement mailed Mar. 9, 2009 for U.S. Appl. No. 11/541,505, filed Sep. 29, 2006; now U.S. Pat. No. 7,658,751.
Restriction Requirement mailed Mar. 9, 2009 for U.S. Appl. No. 11/541,506, filed Sep. 29, 2006; now U.S. Pat. No. 7,601,165.
Restriction Requirement mailed Sep. 29, 2010 for U.S. Appl. No. 12/196,398, filed Aug. 22, 2008; now U.S. Pat. No. 7,959,650.
Roy Alan Majors, M.D.; "Meniscal repairs: proven techniques and current trends," Lippincott Williams & Wilkins, Inc.; 2002.
Saxena, Pankaj, MCh, DNB et al., "Use of Double Wires in Sternal Closure, A Useful Technique," Texas Heart® Institute. Journal List>Tex Heart Inst J > v.33(4); (2006).
Shoulder Arthroscopy; pp. H-2-H-22. (date unknown).
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™ Femoral Fixation Device, Arthrotek, Mar. 31, 2006.
Zeitani, Jacob, M.D., "A New Sternal Reinforcement Device to Prevent and Treat Sternal Dehiscence," CTSNet.org (Jun. 30, 2008).
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique" brochure, Biomet® Sports Medicine. (2013) 16 pages.
Office Action dated Nov. 4, 2014 for U.S. Appl. No. 13/288,459, filed Nov. 3, 2011.
International Search Report and Written Opinion mailed Mar. 6, 2014 for PCT/US2013/075989 which claims benefit of U.S. Appl. No. 13/720,648, filed Dec. 19, 2012.
Ziptight™ Fixation System Featuring Zip Loop™ Technology. Ankle Syndesmosis. Surgical Protocol by Timothy Charlton, M.D. Biomet Sports® Medicine brochure. (Jun. 15, 2011) 8 pages.
U.S. Appl. No. 10/984,624, Final Office Action mailed Jan. 5, 2009, 9 pgs.
U.S. Appl. No. 10/984,624, Non Final Office Action mailed Jul. 10, 2008, 9 pgs.
U.S. Appl. No. 10/984,624, Notice of Allowance mailed Jun. 12, 2009, 9 pgs.
U.S. Appl. No. 10/984,624, Response filed Apr. 1, 2009 to Final Office Action mailed Jan. 5, 2009, 16 pgs.
U.S. Appl. No. 10/984,624, Response filed Apr. 15, 2008 to Restriction Requirement mailed Mar. 24, 2008, 1 pg.
U.S. Appl. No. 10/984,624, Response filed Oct. 10, 2008 to Non Final Office Action mailed Jul. 10, 2008, 12 pgs.
U.S. Appl. No. 10/984,624, Restriction Requirement mailed Mar. 24, 2008, 5 pgs.
U.S. Appl. No. 11/294,694, Final Office Action mailed Sep. 1, 2010, 14 pgs.
U.S. Appl. No. 11/294,694, Non Final Office Action mailed Mar. 16, 2010, 19 pgs.
U.S. Appl. No. 11/294,694, Notice of Allowance mailed Nov. 17, 2010, 4 pgs.
U.S. Appl. No. 11/294,694, Preliminary Amendment filed Jan. 13, 2010, 9 pgs.
U.S. Appl. No. 11/294,694, Response filed Jun. 16, 2010 to Non Final Office Action mailed Mar. 16, 2010, 16 pgs.
U.S. Appl. No. 11/294,694, Response filed Nov. 1, 2010 to Final Office Action mailed Sep. 1, 2010, 10 pgs.
U.S. Appl. No. 11/294,694, Response filed Dec. 22, 2009 to Restriction Requirement mailed Nov. 25, 2009, 1 pg.
U.S. Appl. No. 11/294,694, Restriction Requirement mailed Nov. 25, 2009, 9 pgs.
U.S. Appl. No. 11/347,661, Examiner Interview Summary mailed Sep. 11, 2009, 2 pgs.
U.S. Appl. No. 11/347,661, Final Office Action mailed Mar. 3, 2009, 15 pgs.
U.S. Appl. No. 11/347,661, Non Final Office Action mailed Aug. 13, 2009, 19 pgs.
U.S. Appl. No. 11/347,661, Non Final Office Action mailed Aug. 21, 2008, 11 pgs.
U.S. Appl. No. 11/347,661, Notice of Allowance mailed Feb. 24, 2010, 8 pgs.
U.S. Appl. No. 11/347,661, Notice of Allowance mailed May 5, 2010, 8 pgs.
U.S. Appl. No. 11/347,661, Response filed May 29, 2008 to Restriction Requirement mailed Apr. 20, 2008, 1 pg.
U.S. Appl. No. 11/347,661, Response filed Jun. 3, 2009 to Final Office Action mailed Mar. 3, 2009, 19 pgs.
U.S. Appl. No. 11/347,661, Response filed Nov. 6, 2009 to Non Final Office Action mailed Aug. 13, 2009, 16 pgs.
U.S. Appl. No. 11/347,661, Response filed Nov. 19, 2008 to Non Final Office Action mailed Aug. 21, 2008, 12 pgs.
U.S. Appl. No. 11/347,661, Restriction Requirement mailed Apr. 30, 2008, 6 pgs.
U.S. Appl. No. 11/347,662, Examiner Interview Summary mailed Jun. 24, 2010, 3 pgs.
U.S. Appl. No. 11/347,662, Examiner Interview Summary mailed Nov. 9, 2009, 3 pgs.
U.S. Appl. No. 11/347,662, Final Office Action mailed Sep. 16, 2009, 13 pgs.
U.S. Appl. No. 11/347,662, Final Office Action mailed Oct. 26, 2010, 10 pgs.
U.S. Appl. No. 11/347,662, Non Final Office Action mailed Mar. 9, 2009, 11 pgs.
U.S. Appl. No. 11/347,662, Non Final Office Action mailed May 21, 2010, 19 pgs.
U.S. Appl. No. 11/347,662, Non Final Office Action mailed Oct. 28, 2008, 13 pgs.
U.S. Appl. No. 11/347,662, Response filed Jan. 16, 2009 to Non Final Office Action mailed Oct. 28, 2008, 16 pgs.
U.S. Appl. No. 11/347,662, Response filed Feb. 12, 2010 to Final Office Action mailed Sep. 16, 2009, 21 pgs.
U.S. Appl. No. 11/347,662, Response filed Jun. 5, 2009 to Non Final Office Action mailed Mar. 9, 2009, 13 pgs.
U.S. Appl. No. 11/347,662, Response filed Aug. 20, 2010 to Non Final Office Action mailed May 21, 2010, 13 pgs.
U.S. Appl. No. 11/386,071, Advisory Action mailed Dec. 23, 2010, 3 pgs.
U.S. Appl. No. 11/386,071, Examiner Interview Summary mailed Jan. 31, 2011, 3 pgs.
U.S. Appl. No. 11/386,071, Examiner Interview Summary mailed Jul. 21, 2010, 3 pgs.
U.S. Appl. No. 11/386,071, Final Office Action mailed Oct. 27, 2010, 10 pgs.
U.S. Appl. No. 11/386,071, Non Final Office Action mailed May 12, 2010, 13 pgs.
U.S. Appl. No. 11/386,071, Notice of Allowance mailed Jun. 6, 2011, 6 pgs.
U.S. Appl. No. 11/386,071, Response filed Jan. 26, 2011 to Advisory Action mailed Dec. 23, 2010, 13 pgs.
U.S. Appl. No. 11/386,071, Response filed Aug. 12, 2010 to Non Final Office Action mailed May 12, 2010, 14 pgs.
U.S. Appl. No. 11/386,071, Response filed Dec. 15, 2010 to Final Office Action mailed Oct. 27, 2010, 14 pgs.
U.S. Appl. No. 11/408,282, Final Office Action mailed Dec. 15, 2010, 8 pgs.
U.S. Appl. No. 11/408,282, Non Final Office Action mailed May 23, 2008, 12 pgs.
U.S. Appl. No. 11/408,282, Response filed Aug. 21, 2008 to Non Final Office Action mailed May 23, 2008, 10 pgs.

(56) References Cited

OTHER PUBLICATIONS

U.S. Appl. No. 11/504,882, Examiner Interview Summary mailed Sep. 2, 2010, 3 pgs.
U.S. Appl. No. 11/504,882, Final Office Action mailed Dec. 21, 2010, 7 pgs.
U.S. Appl. No. 11/504,882, Non Final Office Action mailed Jun. 19, 2014, 11 pgs.
U.S. Appl. No. 11/504,882, Non Final Office Action mailed Jun. 23, 2010, 8 pgs.
U.S. Appl. No. 11/504,882, Non Final Office Action mailed Nov. 13, 2013, 13 pgs.
U.S. Appl. No. 11/504,882, Notice of Allowance mailed Dec. 1, 2014, 9 pgs.
U.S. Appl. No. 11/504,882, Response filed Feb. 10, 2014 to Non Final Office Action mailed Nov. 13, 2013, 11 pgs.
U.S. Appl. No. 11/504,882, Response filed Mar. 18, 2011 to Final Office Action mailed Dec. 21, 2010, 11 pgs.
U.S. Appl. No. 11/504,882, Response filed Sep. 17, 2014 to Non Final Office Action mailed Jun. 19, 2014, 14 pgs.
U.S. Appl. No. 11/504,882, Response filed Sep. 23, 2010 to Non Final Office Action mailed Jun. 23, 2010, 12 pgs.
U.S. Appl. No. 11/504,882, Supplemental Notice of Allowability mailed Mar. 12, 2015, 5 pgs.
U.S. Appl. No. 11/541,505, Response filed Apr. 9, 2009 to Restriction Requirement mailed Mar. 9, 2009, 1 pg.
U.S. Appl. No. 11/541,505, Response filed Jun. 18, 2009 to Non Final Office Action mailed May 19, 2009, 5 pgs.
U.S. Appl. No. 11/541,506, Notice of Allowance mailed Jun. 29, 2009, 8 pgs.
U.S. Appl. No. 11/541,506, Response filed Apr. 9, 2009 to Restriction Requirement mailed Mar. 9, 2009, 1 pg.
U.S. Appl. No. 11/739,768, Examiner Interview Summary mailed May 11, 2011, 3 pgs.
U.S. Appl. No. 11/739,768, Examiner Interview Summary mailed Oct. 4, 2011, 3 pgs.
U.S. Appl. No. 11/739,768, Final Office Action mailed Aug. 22, 2011, 14 pgs.
U.S. Appl. No. 11/739,768, Non Final Office Action mailed Mar. 4, 2011, 11 pgs.
U.S. Appl. No. 11/739,768, Notice of Allowance mailed Nov. 15, 2011, 5 pgs.
U.S. Appl. No. 11/739,768, Response filed Jun. 6, 2011 to Non Final Office Action mailed Mar. 4, 2011, 15 pgs.
U.S. Appl. No. 11/739,768, Response filed Oct. 26, 2011 to Final Office Action mailed Aug. 22, 2011, 14 pgs.
U.S. Appl. No. 11/740,035, Final Office Action mailed Aug. 7, 2008, 9 pgs.
U.S. Appl. No. 11/740,035, Non Final Office Action mailed Jan. 3, 2008, 9 pgs.
U.S. Appl. No. 11/740,035, Response filed Apr. 3, 2008 to Non Final Office Action mailed Jan. 3, 2008, 6 pgs.
U.S. Appl. No. 11/784,821, Corrected Notice of Allowance mailed Dec. 24, 2014, 4 pgs.
U.S. Appl. No. 11/784,821, Examiner Interview Summary mailed Jun. 26, 2014, 3 pgs.
U.S. Appl. No. 11/784,821, Examiner Interview Summary mailed Nov. 17, 2009, 3 pgs.
U.S. Appl. No. 11/784,821, Final Office Action mailed Mar. 10, 2010, 11 pgs.
U.S. Appl. No. 11/784,821, Non Final Office Action mailed Mar. 28, 2014, 14 pgs.
U.S. Appl. No. 11/784,821, Non Final Office Action mailed Sep. 4, 2009, 12 pgs.
U.S. Appl. No. 11/784,821, Notice of Allowance mailed Oct. 21, 2014, 10 pgs.
U.S. Appl. No. 11/784,821, Response filed Jun. 10, 2010 to Final Office Action mailed Mar. 10, 2010, 20 pgs.
U.S. Appl. No. 11/784,821, Response filed Jun. 15, 2009 to Restriction Requirement mailed May 13, 2009, 2 pgs.
U.S. Appl. No. 11/784,821, Response filed Jun. 26, 2014 to Non Final Office Action mailed Mar. 28, 2014, 16 pgs.
U.S. Appl. No. 11/784,821, Response filed Nov. 23, 2009 to Non Final Office Action mailed Sep. 4, 2009, 17 pgs.
U.S. Appl. No. 11/784,821, Restriction Requirement mailed May 13, 2009, 6 pgs.
U.S. Appl. No. 11/869,440, Examiner Interview Summary mailed Mar. 25, 2010, 3 pgs.
U.S. Appl. No. 11/869,440, Non Final Office Action mailed Mar. 1, 2010, 13 pgs.
U.S. Appl. No. 11/869,440, Notice of Allowance mailed Aug. 19, 2010, 10 pgs.
U.S. Appl. No. 11/869,440, Response filed Jun. 1, 2010 to Non Final Office Action mailed Mar. 1, 2010, 14 pgs.
U.S. Appl. No. 11/935,681, Examiner Interview Summary mailed Jul. 19, 2010, 3 pgs.
U.S. Appl. No. 11/935,681, Non Final Office Action mailed May 24, 2010, 12 pgs.
U.S. Appl. No. 11/935,681, Notice of Allowance mailed Nov. 8, 2010, 10 pgs.
U.S. Appl. No. 11/935,681, Response filed Apr. 19, 2010 to Restriction Requirement mailed Mar. 17, 2010, 4 pgs.
U.S. Appl. No. 11/935,681, Response filed Aug. 24, 2010 to Non Final Office Action mailed May 24, 2010, 13 pgs.
U.S. Appl. No. 11/935,681, Restriction Requirement mailed Mar. 17, 2010, 6 pgs.
U.S. Appl. No. 12/014,340, Examiner Interview Summary mailed Jun. 22, 2010, 3 pgs.
U.S. Appl. No. 12/014,340, Non Final Office Action mailed May 25, 2010, 12 pgs.
U.S. Appl. No. 12/014,340, Notice of Allowance mailed Nov. 8, 2010, 9 pgs.
U.S. Appl. No. 12/014,340, Preliminary Amendment filed May 21, 2010, 11 pgs.
U.S. Appl. No. 12/014,340, Response filed Apr. 26, 2010 to Restriction Requirement mailed Mar. 25, 2010, 2 pgs.
U.S. Appl. No. 12/014,340, Response filed Aug. 25, 2010 to Non Final Office Action mailed May 25, 2010, 16 pgs.
U.S. Appl. No. 12/014,340, Restriction Requirement mailed Mar. 25, 2010, 9 pgs.
U.S. Appl. No. 12/014,399, Examiner Interview Summary mailed Jun. 23, 2010, 3 pgs.
U.S. Appl. No. 12/014,399, Non Final Office Action mailed May 26, 2010, 13 pgs.
U.S. Appl. No. 12/014,399, Notice of Allowance mailed Nov. 12, 2010, 11 pgs.
U.S. Appl. No. 12/014,399, Preliminary Amendment filed May 25, 2010, 10 pgs.
U.S. Appl. No. 12/014,399, Response filed May 5, 2010 to Restriction Requirement mailed Apr. 6, 2010, 2 pgs.
U.S. Appl. No. 12/014,399, Response filed Aug. 25, 2010 to Non Final Office Action mailed May 26, 2010, 14 pgs.
U.S. Appl. No. 12/014,399, Restriction Requirement mailed Apr. 6, 2010, 9 pgs.
U.S. Appl. No. 12/029,861, Examiner Interview Summary mailed Jan. 27, 2012, 3 pgs.
U.S. Appl. No. 12/029,861, Final Office Action mailed Dec. 8, 2011, 11 pgs.
U.S. Appl. No. 12/029,861, Non Final Office Action mailed Jul. 26, 2011, 11 pgs.
U.S. Appl. No. 12/029,861, Notice of Allowance mailed Apr. 26, 2012, 5 pgs.
U.S. Appl. No. 12/029,861, Response filed Jan. 26, 2012 to Final Office Action mailed Dec. 8, 2011, 15 pgs.
U.S. Appl. No. 12/029,861, Response filed May 6, 2011 to Restriction Requirement mailed Apr. 7, 2011, 10 pgs.
U.S. Appl. No. 12/029,861, Response filed Jun. 23, 2011 to Restriction Requirement mailed May 24, 2011, 1 pgs.
U.S. Appl. No. 12/029,861, Response filed Oct. 14, 2011 to Non Final Office Action mailed Jul. 26, 2011, 11 pgs.
U.S. Appl. No. 12/029,861, Restriction Requirement mailed Apr. 7, 2011, 8 pgs.

(56) References Cited

OTHER PUBLICATIONS

U.S. Appl. No. 12/029,861, Restriction Requirement mailed May 24, 2011, 6 pgs.
U.S. Appl. No. 12/107,437, Examiner Interview Summary mailed May 10, 2010, 4 pgs.
U.S. Appl. No. 12/107,437, Non Final Office Action mailed Mar. 17, 2010, 9 pgs.
U.S. Appl. No. 12/107,437, Preliminary Amendment filed Feb. 23, 2010, 9 pgs.
U.S. Appl. No. 12/107,437, Response filed Jan. 29, 2010 to Restriction Requirement mailed Jan. 13, 2010, 1 pgs.
U.S. Appl. No. 12/107,437, Restriction Requirement mailed Jan. 13, 2010, 7 pgs.
U.S. Appl. No. 12/196,398, Examiner Interview Summary mailed Nov. 8, 2010, 3 pgs.
U.S. Appl. No. 12/196,398, Preliminary Amendment filed Nov. 10, 2008, 3 pgs.
U.S. Appl. No. 12/196,398, Preliminary Amendment filed Dec. 1, 2010, 12 pgs.
U.S. Appl. No. 12/196,398, Preliminary Amendment filed Dec. 9, 2008, 46 pgs.
U.S. Appl. No. 12/196,398, Response filed Oct. 29, 2010 to Restriction Requirement mailed Sep. 29, 2010, 2 pgs.
U.S. Appl. No. 12/196,405, Preliminary Amendment filed Nov. 10, 2008, 3 pgs.
U.S. Appl. No. 12/196,405, Response filed Mar. 16, 2011 to Restriction Requirement mailed Feb. 14, 2011, 1 pgs.
U.S. Appl. No. 12/196,405, Response filed Jul. 12, 2011 to Non Final Office Action mailed Apr. 11, 2011, 19 pgs.
U.S. Appl. No. 12/196,405, Restriction Requirement mailed Feb. 14, 2011, 6 pgs.
U.S. Appl. No. 12/196,405, Supplemental Amendment filed Oct. 3, 2011, 12 pgs.
U.S. Appl. No. 12/196,407, Preliminary Amendment filed Nov. 10, 2008, 3 pgs.
U.S. Appl. No. 12/196,407, Response filed Apr. 20, 2011 to Restriction Requirement mailed Mar. 22, 2011, 12 pgs.
U.S. Appl. No. 12/196,407, Response filed Aug. 2, 2011 to Non Final Office Action mailed May 4, 2011, 27 pgs.
U.S. Appl. No. 12/196,407, Supplemental Response to Non Final Office Action filed Oct. 3, 2011, 18 pgs.
U.S. Appl. No. 12/196,410, Response filed Apr. 20, 2011 to Restriction Requirement mailed Mar. 22, 2011, 13 pgs.
U.S. Appl. No. 12/196,410, Response filed Aug. 1, 2011 to Non Final Office Action mailed May 9, 2011, 23 pgs.
U.S. Appl. No. 12/196,410, Restriction Requirement mailed Mar. 22, 2011, 6 pgs.
U.S. Appl. No. 12/196,410, Supplemental Amendment filed Oct. 3, 2011, 15 pgs.
U.S. Appl. No. 12/398,548, Examiner Interview Summary mailed Jul. 12, 2011, 3 pgs.
U.S. Appl. No. 12/398,548, Non Final Office Action mailed Apr. 12, 2011, 7 pgs.
U.S. Appl. No. 12/398,548, Notice of Allowance mailed Oct. 18, 2011, 7 pgs.
U.S. Appl. No. 12/398,548, Response filed Jul. 12, 2011 to Non Final Office Action mailed Apr. 12, 2011, 15 pgs.
U.S. Appl. No. 12/398,548, Supplemental Preliminary Amendment filed Sep. 7, 2010, 11 pgs.
U.S. Appl. No. 12/419,491, Examiner Interview Summary mailed May 30, 2012, 3 pgs.
U.S. Appl. No. 12/419,491, Examiner Interview Summary mailed Nov. 29, 2011, 3 pgs.
U.S. Appl. No. 12/419,491, Final Office Action mailed Apr. 12, 2012, 12 pgs.
U.S. Appl. No. 12/419,491, Non Final Office Action mailed Sep. 22, 2011, 12 pgs.
U.S. Appl. No. 12/419,491, Notice of Allowance mailed Jul. 13, 2012, 10 pgs.
U.S. Appl. No. 12/419,491, Response filed May 30, 2012 to Final Office Action mailed Apr. 12, 2012, 12 pgs.
U.S. Appl. No. 12/419,491, Response filed Dec. 9, 2011 to Non Final Office Action mailed Sep. 22, 2011, 17 pgs.
U.S. Appl. No. 12/474,802, Notice of Allowance mailed Oct. 26, 2011, 4 pgs.
U.S. Appl. No. 12/474,802, Response filed Mar. 28, 2011 to Restriction Requirement mailed Feb. 24, 2011, 12 pgs.
U.S. Appl. No. 12/474,802, Restriction Requirement mailed Feb. 24, 2011, 6 pgs.
U.S. Appl. No. 12/489,168, Examiner Interview Summary mailed Feb. 21. 2012, 3 pgs.
U.S. Appl. No. 12/489,168, Non Final Office Action mailed Dec. 7, 2011, 10 pgs.
U.S. Appl. No. 12/489,168, Notice of Allowance mailed Apr. 26, 2012, 8 pgs.
U.S. Appl. No. 12/489,168, Notice of Allowance mailed Sep. 5, 2012, 8 pgs.
U.S. Appl. No. 12/489,168, Preliminary Amendment filed Oct. 22, 2009, 3 pgs.
U.S. Appl. No. 12/489,168, Response filed Feb. 27, 2012 to Non Final Office Action mailed Dec. 7, 2011, 15 pgs.
U.S. Appl. No. 12/489,168, Response filed Nov. 11, 2011 to Restriction Requirement mailed Oct. 20, 2011, 1 pg.
U.S. Appl. No. 12/489,168, Restriction Requirement mailed Oct. 20, 2011, 8 pgs.
U.S. Appl. No. 12/489,181, Examiner Interview Summary mailed Feb. 13, 2012, 3 pgs.
U.S. Appl. No. 12/489,181, Non Final Office Action mailed Jan. 3, 2012, 9 pgs.
U.S. Appl. No. 12/489,181, Notice of Allowance mailed May 23, 2012, 9 pgs.
U.S. Appl. No. 12/489,181, Preliminary Amendment filed Mar. 31, 2011, 10 pgs.
U.S. Appl. No. 12/489,181, Preliminary Amendment filed Oct. 22, 2009, 3 pgs.
U.S. Appl. No. 12/489,181, Response filed Mar. 27, 2012 to Non Final Office Action mailed Jan. 3, 2012, 12 pgs.
U.S. Appl. No. 12/489,181, Response filed Dec. 5, 2011 to Restriction Requirement mailed Nov. 4, 2011, 1 pg.
U.S. Appl. No. 12/489,181, Restriction Requirement mailed Nov. 4, 2011, 7 pgs.
U.S. Appl. No. 12/570,854, Examiner Interview Summary mailed Apr. 16, 2011, 3 pgs.
U.S. Appl. No. 12/570,854, Non Final Office Action mailed Feb. 10, 2012, 8 pgs.
U.S. Appl. No. 12/570,854, Notice of Allowance mailed Jun. 29, 2012, 10 pgs.
U.S. Appl. No. 12/570,854, Notice of Allowance mailed Sep. 9, 2012, 6 pgs.
U.S. Appl. No. 12/570,854, Response filed May 10, 2012 to Non Final Office Action mailed Feb. 10, 2012, 27 pgs.
U.S. Appl. No. 12/570,854, Response filed Dec. 20, 2011 to Restriction Requirement mailed Dec. 14, 2011, 1 pg.
U.S. Appl. No. 12/570,854, Restriction Requirement mailed Dec. 14, 2011, 6 pgs.
U.S. Appl. No. 12/702,067, Preliminary Amendment filed Jan. 1, 2011, 13 pgs.
U.S. Appl. No. 12/702,067, Response filed Jun. 5, 2013 to Non Final Office Action mailed Mar. 5, 2013, 17 pgs.
U.S. Appl. No. 12/702,067, Response filed Oct. 2, 2012 to Restriction Requirement mailed Sep. 4, 2012, 1 pg.
U.S. Appl. No. 12/702,067, Restriction Requirement mailed Sep. 4, 2012, 9 pgs.
U.S. Appl. No. 12/719,337, Advisory Action mailed Sep. 30, 2014, 4 pgs.
U.S. Appl. No. 12/719,337, Examiner Interview Summary mailed Apr. 4, 2014, 4 pgs.
U.S. Appl. No. 12/719,337, Examiner Interview Summary mailed May 14, 2013, 3 pgs.
U.S. Appl. No. 12/719,337, Examiner Interview Summary mailed Sep. 18, 2014, 3 pgs.

(56) References Cited

OTHER PUBLICATIONS

U.S. Appl. No. 12/719,337, Final Office Action mailed Mar. 12, 2013, 8 pgs.
U.S. Appl. No. 12/719,337, Final Office Action mailed Jul. 18, 2014, 15 pgs.
U.S. Appl. No. 12/719,337, Non Final Office Action mailed Jan. 10, 2014, 14 pgs.
U.S. Appl. No. 12/719,337, Non Final Office Action mailed Sep. 5, 2012, 7 pgs.
U.S. Appl. No. 12/719,337, Notice of Allowance mailed Mar. 11, 2015, 10 pgs.
U.S. Appl. No. 12/719,337, Notice of Non-Compliant Amendment mailed May 2, 2014, 3 pgs.
U.S. Appl. No. 12/719,337, Response filed Apr. 10, 2014 to Non Final Office Action mailed Jan. 10, 2014, 16 pgs.
U.S. Appl. No. 12/719,337, Response filed May 25, 2012 to Restriction Requirement mailed Apr. 26, 2012, 9 pgs.
U.S. Appl. No. 12/719,337, Response filed Jun. 5, 2013 to Final Office Action mailed Mar. 12, 2013, 16 pgs.
U.S. Appl. No. 12/719,337, Response filed Jun. 25, 2014 to Notice of Non-Compliant Amendment mailed May 2, 2014, 10 pgs.
U.S. Appl. No. 12/719,337, Response filed Sep. 18, 2014 to Final Office Action mailed Jul. 18, 2014, 13 pgs.
U.S. Appl. No. 12/719,337, Response filed Nov. 28, 2012 to Non Final Office Action mailed Sep. 5, 2012, 14 pgs.
U.S. Appl. No. 12/719,337, Restriction Requirement mailed Apr. 26, 2012, 8 pgs.
U.S. Appl. No. 12/788,973, Advisory Action mailed Jan. 23, 2013, 3 pgs.
U.S. Appl. No. 12/788,973, Advisory Action mailed Dec. 27, 2012, 8 pgs.
U.S. Appl. No. 12/788,973, Final Office Action mailed Sep. 18, 2012, 16 pgs.
U.S. Appl. No. 12/788,973, Non Final Office Action mailed May 8, 2012, 12 pgs.
U.S. Appl. No. 12/788,973, Notice of Allowance mailed Mar. 21, 2013, 6 pgs.
U.S. Appl. No. 12/788,973, Response filed Jan. 16, 2013 to Advisory Action mailed Dec. 27, 2012, 9 pgs.
U.S. Appl. No. 12/788,973, Response filed Jul. 19, 2012 to Non Final Office Action mailed May 8, 2012, 21 pgs.
U.S. Appl. No. 12/788,973, Response filed Dec. 16, 2011 to Restriction Requirement mailed Dec. 6, 2011, 11 pgs.
U.S. Appl. No. 12/788,973, Response filed Dec. 17, 2012 to Final Office Action mailed Sep. 18, 2012, 15 pgs.
U.S. Appl. No. 12/788,973, Restriction Requirement mailed Dec. 6, 2011, 9 pgs.
U.S. Appl. No. 12/788,973, Supplemental Notice of Allowance mailed May 24, 2013, 2 pgs.
U.S. Appl. No. 12/788,978, Advisory Action mailed Dec. 24, 2013, 4 pgs.
U.S. Appl. No. 12/788,978, Applicant's Summary of Examiner Interview filed Dec. 12, 2013, 2 pgs.
U.S. Appl. No. 12/788,978, Corrected Notice of Allowance mailed Apr. 30, 2014, 2 pgs.
U.S. Appl. No. 12/788,978, Examiner Interview Summary mailed Jan. 28, 2014, 3 pgs.
U.S. Appl. No. 12/788,978, Examiner Interview Summary mailed Mar. 22, 2013, 3 pgs.
U.S. Appl. No. 12/788,978, Examiner Interview Summary mailed Sep. 11, 2012, 3 pgs.
U.S. Appl. No. 12/788,978, Examiner Interview Summary mailed Oct. 29, 2013, 4 pgs.
U.S. Appl. No. 12/788,978, Examiner Interview Summary mailed Dec. 16, 2013, 3 pgs.
U.S. Appl. No. 12/788,978, Examiner Interview Summary mailed Dec. 27, 2012, 3 pgs.
U.S. Appl. No. 12/788,978, Final Office Action mailed Aug. 20, 2013, 17 pgs.
U.S. Appl. No. 12/788,978, Final Office Action mailed Nov. 2, 2012, 14 pgs.
U.S. Appl. No. 12/788,978, Non Final Office Action mailed Jan. 11, 2013, 16 pgs.
U.S. Appl. No. 12/788,978, Non Final Office Action mailed Jul. 13, 2012, 17 pgs.
U.S. Appl. No. 12/788,978, Notice of Allowance mailed Jan. 24, 2014, 9 pgs.
U.S. Appl. No. 12/788,978, Notice of Non-Compliant Amendment mailed Jun. 6, 2013, 3 pgs.
U.S. Appl. No. 12/788,978, Response filed Jan. 2, 2013 to Final Office Action mailed Nov. 2, 2012, 13 pgs.
U.S. Appl. No. 12/788,978, Response filed Jan. 20, 2014 to Advisory Action mailed Dec. 24, 2013, 4 pgs.
U.S. Appl. No. 12/788,978, Response filed Apr. 8, 2013 to Non Final Office Action mailed Jan. 11, 2013, 16 pgs.
U.S. Appl. No. 12/788,978, Response filed May 21, 2012 to Restriction Requirement mailed Apr. 20, 2012, 12 pgs.
U.S. Appl. No. 12/788,978, Response filed Jul. 3, 2013 to Notice of Non-Compliant Amendment mailed Jun. 6, 2013, 17 pgs.
U.S. Appl. No. 12/788,978, Response filed Oct. 5, 2012 to Non Final Office Action mailed Jul. 13, 2012, 20 pgs.
U.S. Appl. No. 12/788,978, Response filed Nov. 20, 2013 to Final Office Action mailed Aug. 20, 2013, 15 pgs.
U.S. Appl. No. 12/788,978, Restriction Requirement mailed Apr. 20, 2012, 8 pgs.
U.S. Appl. No. 12/828,977, Examiner Interview Summary mailed Jul. 9, 2012, 3 pgs.
U.S. Appl. No. 12/828,977, Non Final Office Action mailed May 3, 2012, 9 pgs.
U.S. Appl. No. 12/828,977, Notice of Allowance mailed Sep. 5, 2012, 9 pgs.
U.S. Appl. No. 12/828,977, Preliminary Amendment filed Jul. 19, 2011, 10 pgs.
U.S. Appl. No. 12/828,977, Response filed Mar. 14, 2012 to Restriction Requirement mailed Feb. 13, 2012, 9 pgs.
U.S. Appl. No. 12/828,977, Response filed Jul. 25, 2012 to Non Final Office Action mailed May 3, 2012, 11 pgs.
U.S. Appl. No. 12/828,977, Restriction Requirement mailed Feb. 13, 2012, 7 pgs.
U.S. Appl. No. 12/915,962, Examiner Interview Summary mailed Jul. 25, 2012, 3 pgs.
U.S. Appl. No. 12/915,962, Non Final Office Action mailed May 7, 2012, 11 pgs.
U.S. Appl. No. 12/915,962, Non Final Office Action mailed Oct. 15, 2012, 9 pgs.
U.S. Appl. No. 12/915,962, Notice of Allowance mailed Jun. 10, 2013, 12 pgs.
U.S. Appl. No. 12/915,962, Response filed Jan. 10, 2013 to Non Final Office Action mailed Oct. 15, 2012, 21 pgs.
U.S. Appl. No. 12/915,962, Response filed Mar. 16, 2012 to Restriction Requirement mailed Feb. 15, 2012, 15 pgs.
U.S. Appl. No. 12/915,962, Response filed Aug. 7, 2012 to Non Final Office Action mailed May 7, 2012, 26 pgs.
U.S. Appl. No. 12/915,962, Restriction Requirement mailed Feb. 15, 2012, 8 pgs.
U.S. Appl. No. 12/938,902, Examiner Interview Summary mailed Dec. 3, 2012, 3 pgs.
U.S. Appl. No. 12/976,328, Examiner Interview Summary mailed Feb. 13, 2012, 3 pgs.
U.S. Appl. No. 12/976,328, Non Final Office Action mailed Dec. 15, 2011, 13 pgs.
U.S. Appl. No. 12/976,328, Notice of Allowance mailed Apr. 30, 2012, 9 pgs.
U.S. Appl. No. 12/976,328, Response filed Mar. 2, 2012 to Non Final Office Action mailed Dec. 15, 2011, 15 pgs.
U.S. Appl. No. 13/045,689, Examiner Interview Summary mailed May 14, 2012, 3 pgs.
U.S. Appl. No. 13/045,689, Non Final Office Action mailed Mar. 20, 2012, 11 pgs.
U.S. Appl. No. 13/045,689, Notice of Allowance mailed Aug. 10, 2012, 10 pgs.

(56) References Cited

OTHER PUBLICATIONS

U.S. Appl. No. 13/045,689, Notice of Allowance mailed Sep. 24, 2012, 7 pgs.
U.S. Appl. No. 13/045,689, Response filed Jan. 30, 2012 to Restriction Requirement mailed Dec. 29, 2011, 13 pgs.
U.S. Appl. No. 13/045,689, Response filed Jun. 8, 2012 to Non Final Office Action mailed Mar. 20, 2012, 15 pgs.
U.S. Appl. No. 13/045,689, Restriction Requirement mailed Dec. 29, 2011, 6 pgs.
U.S. Appl. No. 13/045,691, Examiner Interview Summary mailed May 14, 2012, 3 pgs.
U.S. Appl. No. 13/045,691, Non Final Office Action mailed Mar. 20, 2012, 12 pgs.
U.S. Appl. No. 13/045,691, Notice of Allowance mailed Jun. 19, 2012, 10 pgs.
U.S. Appl. No. 13/045,691, Response filed Feb. 9, 2012 to Restriction Requirement mailed Jan. 9, 2012, 1 pg.
U.S. Appl. No. 13/045,691, Response filed Jun. 8, 2012 to Non Final Office Action mailed Mar. 20, 2012, 17 pgs.
U.S. Appl. No. 13/045,691, Restriction Requirement mailed Jan. 9, 2012, 6 pgs.
U.S. Appl. No. 13/071,563, Final Office Action mailed May 23, 2014, 13 pgs.
U.S. Appl. No. 13/071,563, Non Final Office Action mailed Oct. 23, 2013, 18 pgs.
U.S. Appl. No. 13/071,563, Notice of Allowance mailed Aug. 15, 2014, 7 pgs.
U.S. Appl. No. 13/071,563, Preliminary Amendment filed May 1, 2012, 8 pgs.
U.S. Appl. No. 13/071,563, Preliminary Amendment filed Dec. 6, 2011, 7 pgs.
U.S. Appl. No. 13/071,563, Response filed Jan. 21, 2014 to Non Final Office Action mailed Oct. 23, 2013, 13 pgs.
U.S. Appl. No. 13/071,563, Response filed Jul. 23, 2014 to Final Office Action mailed May 23, 2014, 14 pgs.
U.S. Appl. No. 13/071,563, Response filed Sep. 19, 2013 to Restriction Requirement mailed Aug. 19, 2013, 11 pgs.
U.S. Appl. No. 13/071,563, Restriction Requirement mailed Aug. 19, 2013, 7 pgs.
U.S. Appl. No. 13/098,897, Notice of Allowance mailed Jun. 11, 2013, 13 pgs.
U.S. Appl. No. 13/098,897, Response filed Aug. 30, 2012 to Restriction Requirement mailed Jul. 30, 2012, 16 pgs.
U.S. Appl. No. 13/098,897, Response filed Dec. 18, 2012 to Non Final Office Action mailed Sep. 21, 2012, 21 pgs.
U.S. Appl. No. 13/098,897, Restriction Requirement mailed Jul. 30, 2012, 8 pgs.
U.S. Appl. No. 13/098,927, Advisory Action mailed Aug. 8, 2013, 3 pgs.
U.S. Appl. No. 13/098,927, Applicant's Summary of Examiner Interview filed Sep. 23, 2013, 12 pgs.
U.S. Appl. No. 13/098,927, Examiner Interview Summary mailed Jun. 28, 2013, 3 pgs.
U.S. Appl. No. 13/098,927, Examiner Interview Summary mailed Sep. 20, 2013, 3 pgs.
U.S. Appl. No. 13/098,927, Notice of Allowance mailed Jan. 8, 2014, 5 pgs.
U.S. Appl. No. 13/098,927, Notice of Allowance mailed Sep. 26, 2013, 14 pgs.
U.S. Appl. No. 13/098,927, Response filed Jul. 22, 2015 to Final Office Action mailed May 22, 2013, 17 pgs.
U.S. Appl. No. 13/098,927, Response filed Aug. 27, 2012 to Restriction Requirement mailed Jul. 25, 2012, 14 pgs.
U.S. Appl. No. 13/098,927, Response filed Dec. 21, 2012 to Non Final Office Action mailed Sep. 24, 2012, 21 pgs.
U.S. Appl. No. 13/098,927, Restriction Requirement mailed Jul. 25, 2012, 8 pgs.
U.S. Appl. No. 13/109,667, Advisory Action mailed Feb. 4, 2014, 4 pgs.
U.S. Appl. No. 13/109,667, Examiner Interview Summary mailed Dec. 20, 2013, 3 pgs.
U.S. Appl. No. 13/109,667, Final Office Action mailed Oct. 11, 2013, 19 pgs.
U.S. Appl. No. 13/109,667, Non Final Office Action mailed May 21, 2013, 21 pgs.
U.S. Appl. No. 13/109,667, Notice of Allowance mailed Feb. 18, 2014, 10 pgs.
U.S. Appl. No. 13/109,667, Response filed Jan. 13, 2014 to Final Office Action mailed Oct. 11, 2013, 20 pgs.
U.S. Appl. No. 13/109,667, Response filed May 2, 2013 to Restriction Requirement mailed Apr. 2, 2013, 1 pg.
U.S. Appl. No. 13/109,667, Response filed Aug. 21, 2013 to Non Final Office Action mailed May 21, 2013, 27 pgs.
U.S. Appl. No. 13/109,667, Restriction Requirement mailed Apr. 2, 2013, 8 pgs.
U.S. Appl. No. 13/109,667, Supplemental Notice of Allowability mailed Jun. 12, 2014, 3 pgs.
U.S. Appl. No. 13/109,667, Supplemental Notice of Allowance mailed May 28, 2014, 2 pgs.
U.S. Appl. No. 13/109,667, Supplemental Preliminary Amendment filed Feb. 4, 2014, 16 pgs.
U.S. Appl. No. 13/109,672, 312 Amendment filed Jan. 15, 2015, 3 pgs.
U.S. Appl. No. 13/109,672, Non Final Office Action mailed May 15, 2014, 10 pgs.
U.S. Appl. No. 13/109,672, Notice of Allowance mailed Feb. 3, 2015, 2 pgs.
U.S. Appl. No. 13/109,672, Notice of Allowance mailed Sep. 29, 2014, 9 pgs.
U.S. Appl. No. 13/109,672, PTO Response to Rule 312 Communication mailed Jan. 27, 2015, 2 pgs.
U.S. Appl. No. 13/109,672, Response filed Apr. 14, 2014 to Restriction Requirement mailed Feb. 14, 2014, 15 pgs.
U.S. Appl. No. 13/109,672, Response filed Aug. 15, 2014 to Non Final Office Action mailed May 15, 2014, 20 pgs.
U.S. Appl. No. 13/109,672, Response filed Nov. 4, 2013 to Restriction Requirement mailed Oct. 2, 2013, 10 pgs.
U.S. Appl. No. 13/109,672, Restriction Requirement mailed Feb. 14, 2014, 7 pgs.
U.S. Appl. No. 13/109,672, Restriction Requirement mailed Oct. 2, 2013, 7 pgs.
U.S. Appl. No. 13/111,564, Corrected Notice of Allowance mailed Oct. 9, 2013, 2 pgs.
U.S. Appl. No. 13/111,564, Examiner Interview Summary mailed Jun. 18, 2013, 3 pgs.
U.S. Appl. No. 13/111,564, Non Final Office Action mailed Mar. 18, 2013, 8 pgs.
U.S. Appl. No. 13/111,564, Notice of Allowance mailed Jun. 28, 2013, 12 pgs.
U.S. Appl. No. 13/111,564, Response filed Feb. 4, 2013 to Restriction Requirement mailed Jan. 3, 2013, 20 pgs.
U.S. Appl. No. 13/111,564, Response filed Jun. 18, 2013 to Non Final Office Action mailed Mar. 18, 2013, 25 pgs.
U.S. Appl. No. 13/111,564, Restriction Requirement mailed Jan. 3, 2013, 5 pgs.
U.S. Appl. No. 13/177,153, Final Office Action mailed May 28, 2013, 11 pgs.
U.S. Appl. No. 13/177,153, Non Final Office Action mailed Oct. 2, 2012, 11 pgs.
U.S. Appl. No. 13/177,153, Notice of Allowance mailed Jan. 7, 2014, 4 pgs.
U.S. Appl. No. 13/177,153, Notice of Allowance mailed Sep. 17, 2013, 13 pgs.
U.S. Appl. No. 13/177,153, Response filed Aug. 28, 2013 to Final Office Action mailed May 28, 2013, 19 pgs.
U.S. Appl. No. 13/177,153, Response filed Sep. 4, 2012 to Restriction Requirement mailed Aug. 2, 2012, 15 pgs.
U.S. Appl. No. 13/177,153, Response filed Dec. 20, 2012 to Non Final Office Action mailed Oct. 2, 2012, 16 pgs.
U.S. Appl. No. 13/177,153, Restriction Requirement mailed Aug. 2, 2012, 9 pgs.

(56) References Cited

OTHER PUBLICATIONS

U.S. Appl. No. 13/181,729, Examiner Interview Summary mailed May 9, 2013, 3 pgs.
U.S. Appl. No. 13/181,729, Notice of Allowance mailed May 23, 2013, 9 pgs.
U.S. Appl. No. 13/181,729, Response filed May 13, 2013 to Final Office Action mailed Mar. 13, 2013, 13 pgs.
U.S. Appl. No. 13/181,729, Response filed Dec. 20, 2012 to Non Final Office Action mailed Oct. 2, 2012, 15 pgs.
U.S. Appl. No. 13/269,097, Final Office Action mailed Aug. 8, 2013, 7 pgs.
U.S. Appl. No. 13/269,097, Non Final Office Action mailed Feb. 12, 2013, 10 pgs.
U.S. Appl. No. 13/269,097, Notice of Allowance mailed Feb. 3, 2014, 5 pgs.
U.S. Appl. No. 13/269,097, Notice of Allowance mailed Oct. 21, 2013, 9 pgs.
U.S. Appl. No. 13/269,097, Response filed May 13, 2013 to Non Final Office Action mailed Feb. 12, 2013, 17 pgs.
U.S. Appl. No. 13/269,097, Response filed Oct. 8, 2013 to Final Office Action mailed Aug. 8, 2013, 12 pgs.
U.S. Appl. No. 13/269,097, Response filed Nov. 13, 2012 to Restriction Requirement mailed Oct. 17, 2012, 1 pg.
U.S. Appl. No. 13/269,097, Restriction Requirement mailed Oct. 17, 2012, 8 pgs.
U.S. Appl. No. 13/278,341, Notice of Allowance mailed Jun. 18, 2013, 10 pgs.
U.S. Appl. No. 13/278,341, Response filed Mar. 8, 2013 to Restriction Requirement mailed Feb. 11, 2013, 1 pg.
U.S. Appl. No. 13/278,341, Restriction Requirement mailed Feb. 11, 2013, 6 pgs.
U.S. Appl. No. 13/281,009, Non Final Office Action mailed Jun. 2, 2015, 9 pgs.
U.S. Appl. No. 13/281,009, Notice of Allowance mailed Feb. 24, 2016, 9 pgs.
U.S. Appl. No. 13/281,009, Notice of Allowance mailed Oct. 29, 2015, 8 pgs.
U.S. Appl. No. 13/281,009, Response filed Sep. 2, 2015 to Non Final Office Action mailed Jun. 2, 2015, 13 pgs.
U.S. Appl. No. 13/281,009, Restriction Requirement mailed Feb. 11, 2015, 6 pgs.
U.S. Appl. No. 13/288,459, Examiner Interview Summary mailed Feb. 6, 2015, 3 pgs.
U.S. Appl. No. 13/288,459, Non Final Office Action mailed Jun. 24, 2015, 10 pgs.
U.S. Appl. No. 13/288,459, Notice of Allowance mailed Jan. 11, 2016, 13 pgs.
U.S. Appl. No. 13/288,459, Notice of Allowance mailed May 10, 2016, 7 pgs.
U.S. Appl. No. 13/288,459, Response filed Mar. 3, 2015 to Non Final Office Action mailed Nov. 4, 2014, 16 pgs.
U.S. Appl. No. 13/288,459, Response filed Oct. 13, 2014 to Restriction Requirement mailed Aug. 11, 2014, 15 pgs.
U.S. Appl. No. 13/288,459, Response filed Oct. 23, 2015 to Non Final Office Action mailed Jun. 24, 2015, 14 pgs.
U.S. Appl. No. 13/288,459, Restriction Requirement mailed Aug. 11, 2014, 9 pgs.
U.S. Appl. No. 13/288,463, Examiner Interview Summary mailed Jun. 3, 2014, 3 pgs.
U.S. Appl. No. 13/288,463, Non Final Office Action mailed Feb. 24, 2014, 13 pgs.
U.S. Appl. No. 13/288,463, Notice of Allowance mailed Aug. 27, 2014, 9 pgs.
U.S. Appl. No. 13/288,463, Response filed May 27, 2014 to Non Final Office Action mailed Feb. 24, 2014, 15 pgs.
U.S. Appl. No. 13/288,463, Supplemental Notice of Allowability mailed Dec. 8, 2014, 5 pgs.
U.S. Appl. No. 13/288,463, Supplemental Notice of Allowability mailed Dec. 19, 2014, 5 pgs.
U.S. Appl. No. 13/293,825, Notice of Allowability mailed Jun. 22, 2015, 7 pgs.
U.S. Appl. No. 13/293,825, Notice of Allowance mailed May 19, 2015, 9 pgs.
U.S. Appl. No. 13/293,825, Response filed Apr. 15, 2015 to Restriction Requirement mailed Feb. 12, 2015, 17 pgs.
U.S. Appl. No. 13/293,825, Restriction Requirement mailed Feb. 12, 2015, 9 pgs.
U.S. Appl. No. 13/295,126, Non Final Office Action mailed May 19, 2015, 9 pgs.
U.S. Appl. No. 13/295,126, Notice of Allowance mailed Oct. 22, 2015, 9 pgs.
U.S. Appl. No. 13/295,126, Response filed Apr. 13, 2015 to Restriction Requirement mailed Feb. 12, 2015, 1 pgs.
U.S. Appl. No. 13/295,126, Response filed Aug. 17, 2015 to Non Final Office Action mailed May 19, 2015, 21 pgs.
U.S. Appl. No. 13/295,126, Restriction Requirement mailed Feb. 12, 2015, 9 pgs.
U.S. Appl. No. 13/311,936, Examiner Interview Summary mailed Feb. 12, 2015, 2 pgs.
U.S. Appl. No. 13/311,936, Non Final Office Action mailed Feb. 9, 2015, 13 pgs.
U.S. Appl. No. 13/311,936, Non Final Office Action mailed Oct. 19, 2015, 8 pgs.
U.S. Appl. No. 13/311,936, Notice of Allowance mailed Mar. 29, 2016, 8 pgs.
U.S. Appl. No. 13/311,936, PTO Response to Rule 312 Communication mailed May 10, 2016, 2 pgs.
U.S. Appl. No. 13/311,936, Response filed Jan. 18, 2016 to Non Final Office Action mailed Oct. 19, 2015, 8 pgs.
U.S. Appl. No. 13/311,936, Response filed Jun. 9, 2015 to Non Final Office Action mailed Feb. 9, 2015, 12 pgs.
U.S. Appl. No. 13/311,936, Response filed Oct. 3, 2014 to Restriction Requirement mailed Aug. 5, 2014, 10 pgs.
U.S. Appl. No. 13/311,936, Restriction Requirement mailed Aug. 5, 2014, 7 pgs.
U.S. Appl. No. 13/350,985, Final Office Action mailed Apr. 16, 2015, 8 pgs.
U.S. Appl. No. 13/350,985, Non Final Office Action mailed Dec. 15, 2014, 8 pgs.
U.S. Appl. No. 13/350,985, Notice of Allowance mailed Jul. 27, 2015, 5 pgs.
U.S. Appl. No. 13/350,985, Response filed Mar. 13, 2015 to Non Final Office Action mailed Dec. 15, 2014, 10 pgs.
U.S. Appl. No. 13/350,985, Response filed Jul. 9, 2015 to Final Office Action mailed Apr. 16, 2015, 8 pgs.
U.S. Appl. No. 13/350,985, Response filed Dec. 2, 2014 to Restriction Requirement mailed Oct. 2, 2014, 9 pgs.
U.S. Appl. No. 13/350,985, Restriction Requirement mailed Oct. 2, 2014, 6 pgs.
U.S. Appl. No. 13/399,125, Corrected Notice of Allowance mailed Aug. 28, 2014, 2 pgs.
U.S. Appl. No. 13/399,125, Examiner Interview Summary mailed May 17, 2013, 3 pgs.
U.S. Appl. No. 13/399,125, Notice of Allowance mailed May 16, 2014, 8 pgs.
U.S. Appl. No. 13/399,125, Response filed Jan. 10, 2013 to Non Final Office Action mailed Oct. 24, 2012, 15 pgs.
U.S. Appl. No. 13/399,125, Response filed May 20, 2013 to Final Office Action mailed Mar. 20, 2013, 14 pgs.
U.S. Appl. No. 13/412,105, Advisory Action mailed Feb. 24, 2014, 3 pgs.
U.S. Appl. No. 13/412,105, Examiner Interview Summary mailed Feb. 6, 2014, 3 pgs.
U.S. Appl. No. 13/412,105, Examiner Interview Summary mailed Oct. 11, 2013, 3 pgs.
U.S. Appl. No. 13/412,105, Non Final Office Action mailed Jul. 15, 2013, 10 pgs.
U.S. Appl. No. 13/412,105, Notice of Allowance mailed Aug. 18, 2014, 9 pgs.
U.S. Appl. No. 13/412,105, Response filed Feb. 10, 2014 to Final Office Action mailed Dec. 13, 2013, 14 pgs.

(56) References Cited

OTHER PUBLICATIONS

U.S. Appl. No. 13/412,105, Response filed Mar. 13, 2014 to Advisory Action mailed Feb. 24, 2014, 19 pgs.
U.S. Appl. No. 13/412,105, Response filed May 6, 2013 to Restriction Requirement mailed Apr. 5, 2013, 9 pgs.
U.S. Appl. No. 13/412,105, Response filed Oct. 14, 2013 to Non Final Office Action mailed Jul. 15, 2013, 13 pgs.
U.S. Appl. No. 13/412,105, Restriction Requirement mailed Apr. 5, 2013, 9 pgs.
U.S. Appl. No. 13/412,116, Corrected Notice of Allowance mailed Jun. 2, 2014, 2 pgs.
U.S. Appl. No. 13/412,116, Examiner Interview Summary mailed Dec. 13, 2013, 3 pgs.
U.S. Appl. No. 13/412,116, Notice of Allowance mailed Feb. 19, 2014, 9 pgs.
U.S. Appl. No. 13/412,116, Response filed Jul. 3, 2013 to Restriction Requirement mailed Jun. 19, 2013, 1 pg.
U.S. Appl. No. 13/412,116, Response filed Dec. 11, 2013 to Non Final Office Action mailed Sep. 11, 2013, 11 pgs.
U.S. Appl. No. 13/412,116, Restriction Requirement mailed Jun. 19, 2013, 9 pgs.
U.S. Appl. No. 13/412,127, Examiner Interview Summary mailed Nov. 5, 2013, 3 pgs.
U.S. Appl. No. 13/412,127, Response filed May 23, 2013 to Restriction Requirement mailed Apr. 24, 2013, 2 pgs.
U.S. Appl. No. 13/412,127, Response filed Nov. 5, 2013 to Non Final Office Action mailed Aug. 7, 2013, 16 pgs.
U.S. Appl. No. 13/412,127, Restriction Requirement mailed Apr. 24, 2013, 10 pgs.
U.S. Appl. No. 13/587,374, Final Office Action mailed Nov. 6, 2013, 9 pgs.
U.S. Appl. No. 13/587,374, Notice of Allowance mailed Feb. 28, 2014, 5 pgs.
U.S. Appl. No. 13/587,374, Preliminary Amendment filed Jun. 21, 2013, 9 pgs.
U.S. Appl. No. 13/587,374, Response filed Jan. 24, 2014 to Final Office Action mailed Nov. 6, 2013, 15 pgs.
U.S. Appl. No. 13/587,374, Response filed Oct. 14, 2013 to Non Final Office Action mailed Jul. 17, 2013, 14 pgs.
U.S. Appl. No. 13/625,413, Final Office Action mailed Oct. 30, 2015, 8 pgs.
U.S. Appl. No. 13/625,413, Non Final Office Action mailed Jun. 8, 2015, 11 pgs.
U.S. Appl. No. 13/625,413, Notice of Allowance mailed Apr. 1, 2016, 8 pgs.
U.S. Appl. No. 13/625,413, Notice of Allowance mailed Dec. 11, 2015, 9 pgs.
U.S. Appl. No. 13/625,413, Response filed May 11, 2015 to Restriction Requirement mailed Mar. 10, 2015, 1 pg.
U.S. Appl. No. 13/625,413, Response filed Sep. 8, 2015 to Non Final Office Action mailed Jun. 8, 2015, 16 pgs.
U.S. Appl. No. 13/625,413, Response filed Dec. 1, 2015 to Final Office Action mailed Oct. 30, 2015, 9 pgs.
U.S. Appl. No. 13/625,413, Restriction Requirement mailed Mar. 10, 2015, 7 pgs.
U.S. Appl. No. 13/645,964, Advisory Action mailed Feb. 4, 2016, 2 pgs.
U.S. Appl. No. 13/645,964, Final Office Action mailed Oct. 6, 2015, 17 pgs.
U.S. Appl. No. 13/645,964, Non Final Office Action mailed Mar. 15, 2016, 15 pgs.
U.S. Appl. No. 13/645,964, Non Final Office Action mailed Mar. 17, 2015, 15 pgs.
U.S. Appl. No. 13/645,964, Response filed Jul. 17, 2015 to Non Final Office Action mailed Mar. 17, 2015, 17 pgs.
U.S. Appl. No. 13/645,964, Response filed Dec. 4, 2015 to Final Office Action mailed Oct. 6, 2015, 14 pgs.
U.S. Appl. No. 13/656,821, Notice of Allowance mailed Jun. 18, 2015, 11 pgs.
U.S. Appl. No. 13/656,821, Response filed May 11, 2015 to Restriction Requirement mailed Mar. 10, 2015, 1 pg.
U.S. Appl. No. 13/656,821, Restriction Requirement mailed Mar. 10, 2015, 6 pgs.
U.S. Appl. No. 13/720,648, Final Office Action mailed Nov. 16, 2015, 7 pgs.
U.S. Appl. No. 13/720,648, Non Final Office Action mailed Jun. 10, 2015, 11 pgs.
U.S. Appl. No. 13/720,648, Notice of Allowance mailed Feb. 5, 2016, 11 pgs.
U.S. Appl. No. 13/720,648, Response filed Jan. 13, 2016 to Final Office Action mailed Nov. 16, 2015, 9 pgs.
U.S. Appl. No. 13/720,648, Response filed May 11, 2015 to Restriction Requirement mailed Mar. 10, 2015, 8 pgs.
U.S. Appl. No. 13/720,648, Response filed Oct. 9, 2015 to Non Final Office Action mailed Jun. 10, 2015, 12 pgs.
U.S. Appl. No. 13/720,648, Restriction Requirement mailed Mar. 10, 2015, 8 pgs.
U.S. Appl. No. 13/721,970, Notice of Allowance mailed Aug. 12, 2013, 13 pgs.
U.S. Appl. No. 13/721,970, Preliminary Amendment filed Mar. 15, 2013, 13 pgs.
U.S. Appl. No. 13/721,970, Response filed Mar. 18, 2013 to Restriction Requirement mailed Apr. 11, 2013, 1 pgs.
U.S. Appl. No. 13/721,970, Restriction Requirement mailed Apr. 11, 2013, 6 pgs.
U.S. Appl. No. 13/751,846, Final Office Action mailed Nov. 17, 2015, 9 pgs.
U.S. Appl. No. 13/751,846, Non Final Office Action mailed Jun. 15, 2015, 10 pgs.
U.S. Appl. No. 13/751,846, Notice of Allowance mailed Mar. 16, 2016, 11 pgs.
U.S. Appl. No. 13/751,846, Response filed Feb. 5, 2016 to Final Office Action mailed Nov. 17, 2015, 14 pgs.
U.S. Appl. No. 13/751,846, Response filed May 11, 2015 to Restriction Requirement mailed Mar. 10, 2015, 15 pgs.
U.S. Appl. No. 13/751,846, Response filed Oct. 9, 2015 to Non Final Office Action mailed Jun. 15, 2015, 20 pgs.
U.S. Appl. No. 13/751,846, Restriction Requirement mailed Mar. 10, 2015, 7 pgs.
U.S. Appl. No. 13/757,003, Non Final Office Action mailed Jun. 25, 2015, 8 pgs.
U.S. Appl. No. 13/757,003, Notice of Allowance mailed Feb. 8, 2016, 10 pgs.
U.S. Appl. No. 13/757,003, Response filed May 12, 2015 to Restriction Requirement mailed Mar. 12, 2015, 9 pgs.
U.S. Appl. No. 13/757,003, Response filed Oct. 26, 2015 to Non Final Office Action mailed Jul. 25, 2015, 8 pgs.
U.S. Appl. No. 13/757,003, Restriction Requirement mailed Mar. 12, 2015, 6 pgs.
U.S. Appl. No. 13/757,019, Non Final Office Action mailed Jun. 25, 2015, 11 pgs.
U.S. Appl. No. 13/757,019, Notice of Allowance mailed Dec. 10, 2015, 10 pgs.
U.S. Appl. No. 13/757,019, Response filed May 11, 2015 to Restriction Requirement mailed Mar. 11, 2015, 9 pgs.
U.S. Appl. No. 13/757,019, Response filed Oct. 26, 2015 to Non Final Office Action mailed Jun. 25, 2015, 9 pgs.
U.S. Appl. No. 13/757,019, Restriction Requirement mailed Mar. 11, 2015, 10 pgs.
U.S. Appl. No. 13/767,401, Non Final Office Action mailed Aug. 26, 2015, 9 pgs.
U.S. Appl. No. 13/767,401, Notice of Allowance mailed Apr. 8, 2016, 9 pgs.
U.S. Appl. No. 13/767,401, Notice of Allowance mailed Dec. 30, 2015, 9 pgs.
U.S. Appl. No. 13/767,401, Response filed May 18, 2015 to Restriction Requirement mailed Mar. 17, 2015, 15 pgs.
U.S. Appl. No. 13/767,401, Response filed Nov. 6, 2015 to Non Final Office Action mailed Aug. 26, 2015, 12 pgs.
U.S. Appl. No. 13/767,401, Restriction Requirement mailed Mar. 17, 2015, 8 pgs.

(56) References Cited

OTHER PUBLICATIONS

U.S. Appl. No. 13/790,982, Examiner Interview Summary mailed Jun. 9, 2015, 3 pgs.
U.S. Appl. No. 13/790,982, Non Final Office Action mailed Sep. 16, 2015, 11 pgs.
U.S. Appl. No. 13/790,982, Notice of Allowance mailed Feb. 24, 2016, 10 pgs.
U.S. Appl. No. 13/790,982, Response filed Jun. 2, 2015 to Restriction Requirement mailed Apr. 2, 2015, 11 pgs.
U.S. Appl. No. 13/790,982, Response filed Dec. 16, 2015 to Non Final Office Action mailed Sep. 16, 2015, 10 pgs.
U.S. Appl. No. 13/790,982, Restriction Requirement mailed Apr. 2, 2015, 10 pgs.
U.S. Appl. No. 13/790,997, Examiner Interview Summary mailed Jun. 8, 2015, 3 pgs.
U.S. Appl. No. 13/790,997, Non Final Office Action mailed Sep. 21, 2015, 8 pgs.
U.S. Appl. No. 13/790,997, Notice of Allowance mailed Mar. 2, 2016, 9 pgs.
U.S. Appl. No. 13/790,997, Response filed Jun. 2, 2015 to Restriction Requirement mailed Apr. 2, 2015, 12 pgs.
U.S. Appl. No. 13/790,997, Response filed Dec. 18, 2015 to Non Final Office Action mailed Sep. 21, 2015, 9 pgs.
U.S. Appl. No. 13/790,997, Restriction Requirement mailed Apr. 2, 2015, 8 pgs.
U.S. Appl. No. 13/833,567, Advisory Action mailed Apr. 28, 2016, 3 pgs.
U.S. Appl. No. 13/833,567, Final Office Action mailed Mar. 9, 2016, 9 pgs.
U.S. Appl. No. 13/833,567, Non Final Office Action mailed Oct. 23, 2015, 10 pgs.
U.S. Appl. No. 13/833,567, Response filed Jan. 22, 2016 to Non Final Office Action mailed Oct. 23, 2015, 11 pgs.
U.S. Appl. No. 13/833,567, Response filed Jun. 25, 2015 to Restriction Requirement mailed Apr. 3, 2015, 10 pgs.
U.S. Appl. No. 13/833,567, Restriction Requirement mailed Apr. 3, 2015, 6 pgs.
U.S. Appl. No. 13/838,755, Final Office Action mailed Feb. 22, 2016, 9 pgs.
U.S. Appl. No. 13/838,755, Non Final Office Action mailed Sep. 17, 2015, 11 pgs.
U.S. Appl. No. 13/838,755, Notice of Allowance mailed Apr. 27, 2016, 7 pgs.
U.S. Appl. No. 13/838,755, Response filed Apr. 15, 2016 to Final Office Action mailed Feb. 22, 2016, 11 pgs.
U.S. Appl. No. 13/838,755, Response filed Jun. 8, 2015 to Restriction Requirement mailed Apr. 6, 2015, 1 pg.
U.S. Appl. No. 13/838,755, Response filed Dec. 1, 2015 to Non Final Office Action mailed Sep. 17, 2015, 13 pgs.
U.S. Appl. No. 13/838,755, Restriction Requirement mailed Apr. 6, 2015, 6 pgs.
U.S. Appl. No. 13/889,851, Non Final Office Action mailed Apr. 6, 2015, 10 pgs.
U.S. Appl. No. 13/889,851, Notice of Allowance mailed Aug. 12, 2015, 8 pgs.
U.S. Appl. No. 13/889,851, Response filed Feb. 26, 2015 to Restriction Requirement mailed Jan. 21, 2015, 12 pgs.
U.S. Appl. No. 13/889,851, Response filed Jul. 6, 2015 to Non Final Office Action mailed Apr. 6, 2015, 14 pgs.
U.S. Appl. No. 13/889,851, Restriction Requirement mailed Jan. 21, 2015, 6 pgs.
U.S. Appl. No. 13/889,851, Supplemental Amendment and Response filed Jul. 6, 2015 to Non Final Office Action mailed Apr. 6, 2015, 8 pgs.
U.S. Appl. No. 13/959,145, Examiner Interview Summary mailed Sep. 16, 2015, 3 pgs.
U.S. Appl. No. 13/959,145, Final Office Action mailed Jan. 29, 2016, 16 pgs.
U.S. Appl. No. 13/959,145, Final Office Action mailed Feb. 5, 2015, 22 pgs.
U.S. Appl. No. 13/959,145, Non Final Office Action mailed Jul. 31, 2015, 21 pgs.
U.S. Appl. No. 13/959,145, Non Final Office Action mailed Sep. 15, 2014, 20 pgs.
U.S. Appl. No. 13/959,145, Notice of Allowance mailed Apr. 13, 2016, 5 pgs.
U.S. Appl. No. 13/959,145, Response filed Mar. 28, 2016 to Final Office Action mailed Jan. 29, 2016, 10 pgs.
U.S. Appl. No. 13/959,145, Response filed Jul. 6, 2015 to Final Office Action mailed Feb. 5, 2015, 18 pgs.
U.S. Appl. No. 13/959,145, Response filed Oct. 30, 2015 to Non Final Office Action mailed Jul. 31, 2015, 14 pgs.
U.S. Appl. No. 13/959,145, Response filed Dec. 15, 2014 to Non Final Office Action mailed Sep. 15, 2014, 21 pgs.
U.S. Appl. No. 14/055,172, Response filed May 4, 2016 to Restriction Requirement mailed Mar. 4, 2016, 8 pgs.
U.S. Appl. No. 14/055,172, Restriction Requirement mailed Mar. 4, 2016, 6 pgs.
U.S. Appl. No. 14/055,191, Non Final Office Action mailed May 16, 2016, 8 pgs.
U.S. Appl. No. 14/055,191, Response filed Apr. 29, 2016 to Restriction Requirement mailed Mar. 7, 2016, 8 pgs.
U.S. Appl. No. 14/055,191, Restriction Requirement mailed Mar. 7, 2016, 6 pgs.
U.S. Appl. No. 14/071,295, Non Final Office Action mailed Aug. 15, 2014, 6 pgs.
U.S. Appl. No. 14/071,295, Notice of Allowance mailed Dec. 10, 2014, 8 pgs.
U.S. Appl. No. 14/071,295, Response filed Nov. 17, 2014 to Non Final Office Action mailed Aug. 15, 2014, 14 pgs.
U.S. Appl. No. 14/071,295, Supplemental Notice of Allowability mailed Jan. 26, 2015, 2 pgs.
U.S. Appl. No. 14/095,614, Preliminary Amendment filed Apr. 15, 2014, 17 pgs.
U.S. Appl. No. 14/159,094, Restriction Requirement mailed Apr. 20, 2016, 6 pgs.
U.S. Appl. No. 14/182,038, Restriction Requirement mailed Apr. 26, 2016, 7 pgs.
U.S. Appl. No. 14/182,046, Restriction Requirement mailed Apr. 26, 2016, 6 pgs.
U.S. Appl. No. 14/211,977, Preliminary Amendment filed Mar. 2, 2016, 7 pgs.
U.S. Appl. No. 14/211,977, Response filed Apr. 29, 2016 to Restriction Requirement mailed Mar. 11, 2016, 8 pgs.
U.S. Appl. No. 14/211,977, Restriction Requirement mailed Mar. 11, 2016, 6 pgs.
U.S. Appl. No. 14/215,550, Restriction Requirement mailed Apr. 28, 2016, 6 pgs.
U.S. Appl. No. 14/275,548, Examiner Interview Summary mailed Apr. 25, 2016, 3 pgs.
U.S. Appl. No. 14/275,548, Non Final Office Action mailed Feb. 19, 2016, 14 pgs.
U.S. Appl. No. 14/275,548, Response filed May 19, 2016 to Non Final Office Action mailed Feb. 19, 2016, 19 pgs.
U.S. Appl. No. 14/324,688, Non Final Office Action mailed Jan. 8, 2016, 18 pgs.
U.S. Appl. No. 14/324,688, Response filed Apr. 8, 2016 to Non Final Office Action mailed Jan. 8, 2016, 15 pgs.
U.S. Appl. No. 14/456,286, Non Final Office Action mailed Dec. 30, 2015, 16 pgs.
U.S. Appl. No. 14/456,286, Response filed Mar. 30, 2016 to Non Final Office Action mailed Dec. 30, 2015, 15 pgs.
U.S. Appl. No. 14/456,286, Response filed Dec. 11, 2015 to Restriction Requirement mailed Oct. 29, 2015, 6 pgs.
U.S. Appl. No. 14/456,286, Restriction Requirement mailed Oct. 29, 2015, 9 pgs.
U.S. Appl. No. 14/589,101, Final Office Action mailed Oct. 2, 2015, 10 pgs.
U.S. Appl. No. 14/589,101, Non Final Office Action mailed Feb. 12, 2015, 10 pgs.
U.S. Appl. No. 14/589,101, Non Final Office Action mailed May 5, 2016, 14 pgs.

(56) References Cited

OTHER PUBLICATIONS

U.S. Appl. No. 14/589,101, Response filed Jun. 12, 2015 to Non Final Office Action mailed Feb. 12, 2015, 11 pgs.
U.S. Appl. No. 14/589,101, Response filed Dec. 29, 2015 to Final Office Action mailed Oct. 2, 2015, 15 pgs.
U.S. Appl. No. 14/697,140, Non Final Office Action mailed Apr. 8, 2016, 8 pgs.
U.S. Appl. No. 14/794,309, Preliminary Amendment filed Sep. 22, 2015, 6 pgs.
U.S. Appl. No. 14/794,309, Supplemental Preliminary Amendment filed Mar. 3, 2016, 8 pgs.
U.S. Appl. No. 14/876,167, Preliminary Amendment filed Oct. 27, 2015, 8 pgs.
U.S. Appl. No. 14/936,831, Preliminary Amendment filed Nov. 11, 2015, 6 pgs.
U.S. Appl. No. 14/956,724, Preliminary Amendment filed Dec. 7, 2015, 8 pgs.
U.S. Appl. No. 14/956,724, Supplemental Preliminary Amendment filed Feb. 11, 2016, 7 pgs.
U.S. Appl. No. 14/983,108, Preliminary Amendment filed Dec. 30, 2015, 7 pgs.
U.S. Appl. No. 14/983,747, Preliminary Amendment filed Jan. 4, 2016, 5 pgs.
U.S. Appl. No. 15/060,007, Preliminary Amendment filed Mar. 9, 2016, 9 pgs.
U.S. Appl. No. 15/061,352, Preliminary Amendment filed Mar. 7, 2016, 8 pgs.
U.S. Appl. No. 15/074,553, Preliminary Amendment filed Mar. 21, 2016, 8 pgs.
U.S. Appl. No. 12/938,902, Non Final Office Action mailed Sep. 17, 2012, 11 pgs.
U.S. Appl. No. 12/938,902, Notice of Allowance mailed Jun. 21, 2013, 13 pgs.
U.S. Appl. No. 12/938,902, Notice of Allowance mailed Oct. 1, 2013, 9 pgs.
U.S. Appl. No. 12/938,902, Response filed Aug. 6, 2012 to Restriction Requirement mailed Jul. 6, 2012, 14 pgs.
U.S. Appl. No. 12/938,902, Response filed Dec. 10, 2012 to Non Final Office Action mailed Sep. 17, 2012, 20 pgs.
U.S. Appl. No. 12/938,902, Restriction Requirement mailed Jul. 6, 2012, 8 pgs.
U.S. Appl. No. 13/833,567, Response filed Apr. 20, 2016 to Final Office Action mailed Mar. 9, 2016, 10 pgs.
"Bio-Intrafix Tibial Soft Tissue Fastener, Building on the Legacy of IntraFix", DePuy Mitek brochure, (Feb. 2007), 6 pgs.
"Bio-Intrafix Tibial Soft Tissue Fasteners, Building on the Legacy of IntraFix", (Feb. 2007), 6 pgs.
European Application Serial No. 10727548.9, Examination Notification Art. 94(3) mailed Sep. 18, 2014, 6 pgs.
European Application Serial No. 10727548.9, Office Action mailed Jan. 11, 2016, 6 pgs.
European Application Serial No. 10727548.9, Office Action mailed Jan. 19, 2012, 2 pgs.
European Application Serial No. 10727548.9, Response filed Mar. 19, 2015 to Examination Notification Art. 94(3) mailed Sep. 18, 2014, 23 pgs.
European Application Serial No. 11707316.3, Examination Notification Art. 94(3) mailed Feb. 4, 2014, 3 pgs.
European Application Serial No. 11707316.3, Examination Notification Art. 94(3) mailed Dec. 17, 2014, 5 pgs.
European Application Serial No. 11707316.3, Office Action mailed Nov. 10, 2015, 6 pgs.
European Application Serial No. 11707316.3, Response filed Jun. 5, 2014 to Examination Notification Art. 94(3) mailed Feb. 4, 2014, 7 pgs.
European Application Serial No. 11707316.3, Response filed Jun. 29, 2015 to Examination Notification Art. 94(3) mailed Dec. 17, 2014, 25 pgs.
European Application Serial No. 12721676.0, Communication pursuant to Article 94(3) EPC mailed Sep. 30, 2015, 4 pgs.
European Application Serial No. 12721676.0, Office Action mailed Jan. 3, 2014, 2 pgs.
European Application Serial No. 12721676.0, Preliminary Amendment filed Nov. 19, 2013, 9 pgs.
European Application Serial No. 12721676.0, Response filed Jul. 10, 2014 to Office Action mailed Jan. 3, 2014, 2 pgs.
European Application Serial No. 12791902.5, Examination Notification Art. 94(3) mailed Aug. 14, 2015, 4 pgs.
European Application Serial No. 12791902.5, Office Action mailed Jul. 15, 2014, 2 pgs.
European Application Serial No. 12806211.4, Examination Notification Art. 94(3) mailed Aug. 13, 2015, 5 pgs.
European Application Serial No. 12806211.4, Office Action mailed Jul. 18, 2014, 2 pgs.
European Application Serial No. 13818131.8, Office Action mailed Jul. 28, 2015, 2 pgs.
European Application Serial No. 13818131.8, Response filed Feb. 8, 2016 to Office Action mailed Jul. 28, 2015, 14 pgs.
European Application Serial No. 14716173.1, Office Action mailed Nov. 5, 2015, 2 pgs.
International Application Serial No. PCT/US2009/039580, International Preliminary Report on Patentability mailed Nov. 4, 2010, 9 pgs.
International Application Serial No. PCT/US2009/039580, International Search Report mailed Jul. 30, 2009, 4 pgs.
International Application Serial No. PCT/US2009/039580, Written Opinion mailed Jul. 30, 2009, 7 pgs.
International Application Serial No. PCT/US2010/036602, International Preliminary Report on Patentability mailed Dec. 8, 2011, 9 pgs.
International Application Serial No. PCT/US2010/036602, International Search Report mailed Nov. 8, 2010, 6 pgs.
International Application Serial No. PCT/US2010/036602, Written Opinion mailed Nov. 8, 2010, 7 pgs.
International Application Serial No. PCT/US2012/030294, International Preliminary Report on Patentability mailed Oct. 10, 2013, 9 pgs.
International Application Serial No. PCT/US2012/030294, International Search Report mailed May 23, 2012, 6 pgs.
International Application Serial No. PCT/US2012/030294, Written Opinion mailed May 23, 2012, 7 pgs.
International Application Serial No. PCT/US2012/037703, Written Opinion mailed Nov. 28, 2013.
International Application Serial No. PCT/US2012/062738, International Preliminary Report on Patentability mailed May 15, 2014, 9 pgs.
International Application Serial No. PCT/US2012/062738, International Search Report mailed Mar. 6, 2013, 6 pgs.
International Application Serial No. PCT/US2012/062738, Written Opinion mailed Mar. 6, 2013, 7 pgs.
International Application Serial No. PCT/US2013/075989, International Preliminary Report on Patentability mailed Jul. 2, 2015, 10 pgs.
International Application Serial No. PCT/US2014/026413, International Preliminary Report on Patentability mailed Sep. 24, 2015, 10 pgs.
"Mallory-Head Modular Calcar Revision System", Biomet Orthopedics, Inc., (2006), 20 pgs.
"SportMesh™ Soft Tissue Reinforcment, Made from . . . Artelon® optimal tissue repair", Biomet® Sports Medicine, Inc., (2007), 8 pgs.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Anitua, Eduardo, et al., "Autologous platelets as a source of proteins for healing and tissue regeneration", Thromb Haemost, vol. 91, (2004), 4-15.
Arthrotek, "A Biomet Company; Sure fire Hybrid Meniscal Device", Fall AANA, (2004), 37 pgs.
Charlton, Timothy, "Ziptight™ Fixation System Featuring Zip Loop™ Technology. Ankle Syndesmosis. Surgical Protocol", Biomet Sports® Medicine brochure, (Jun. 15, 2011), 8 pgs.

(56) References Cited

OTHER PUBLICATIONS

Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.

Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.

Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.

Mithoefer, Kai MD, et al., "The Microfracture Technique for the Treatment of Articular Cartilage Lesions in the Knee. A Prospective Cohort Study", The Journal of Bone and Joint Surgery 87(9), (Sep. 2005), 1911-1920.

Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.

Roseberg, MD, Thomas D, "ACL Reconstruction with Acufex Director Drill Guide and Endobutton CL Fixation System", Smith & Nephew: Knee Series, Technique Guide, (2005), 12 pgs.

Steadman, et al., "Microfracture: Surgical Technique and Rehalibitation to Treat Chondral Defects", Clinical Orthopaedics and Related Research 391, (2001), S362-S369.

\* cited by examiner

METHOD AND APPARATUS FOR COUPLING SOFT TISSUE TO A BONE

CROSS-REFERENCE TO RELATED APPLICATIONS

This application is a divisional of U.S. patent application Ser. No. 13/278,341 filed on Oct. 21, 2011, which is a continuation of U.S. patent application Ser. No. 12/474,802 filed on May 29, 2009, now U.S. Pat. No. 8,088,130 issued on Jan. 3, 2012; which is a continuation-in-part of: (1.) U.S. patent application Ser. No. 11/541,506 filed on Sep. 29, 2006, now U.S. Pat. No. 7,601,165 issued on Oct. 13, 2009; (2.) U.S. patent application Ser. No. 11/541,505 filed on Sep. 29, 2006, now U.S. Pat. No. 7,658,751 issued on Feb. 9, 2010; (3.) U.S. patent application Ser. No. 12/014,399 filed on Jan. 15, 2008, now U.S. Pat. No. 7,909,851 issued on Mar. 22, 2011; (4.) U.S. patent application Ser. No. 12/014,340 filed on Jan. 15, 2008, now U.S. Pat. No. 7,905,904 issued on Mar. 15, 2011; (5.) U.S. patent application Ser. No. 11/935,681 filed on Nov. 6, 2007, now U.S. Pat. No. 7,905,903 issued on Mar. 15, 2011; (6.) U.S. patent application Ser. No. 11/869,440 filed on Oct. 9, 2007, now U.S. Pat. No. 7,857,830 issued on Dec. 28, 2010; (7.) U.S. patent application Ser. No. 11/784,821 filed on Apr. 10, 2007; (8.) U.S. patent application Ser. No. 11/347,661 filed on Feb. 3, 2006, now U.S. Pat. No. 7,749,350 issued on Jul. 6, 2010; (9.) U.S. patent application Ser. No. 11/347,662 filed on Feb. 3, 2006, now abandoned.

This application is also a continuation-in-part of U.S. patent application Ser. No. 13/412,105 filed on Mar. 5, 2012, which is a continuation-in-part of: (1.) U.S. patent application Ser. No. 12/196,405 filed on Aug. 22, 2008, now U.S. Pat. No. 8,128,658 issued on Mar. 6, 2012; (2.) U.S. patent application Ser. No. 12/196,407, filed on Aug. 22, 2008, now U.S. Pat. No. 8,137,382 issued on Mar. 20, 2012; and (3.) U.S. patent application Ser. No. 12/196,410, filed on Aug. 22, 2008, now U.S. Pat. No. 8,118,836 issued on Feb. 21, 2012.

The disclosures of the above applications are incorporated herein by reference.

FIELD

The present disclosure relates to method of coupling soft tissue and, more particularly, to a method of coupling soft tissue to a bone.

BACKGROUND

The statements in this section merely provide background information related to the present disclosure and may not constitute prior art.

It is commonplace in arthroscopic procedures to employ sutures and anchors to secure soft tissues to bone. Despite their widespread use, several improvements in the use of sutures and suture anchors may be made. For example, the procedure of tying knots may be very time consuming, thereby increasing the cost of the procedure and limiting the capacity of the surgeon. Furthermore, the strength of the repair may be limited by the strength of the knot. This latter drawback may be of particular significance if the knot is tied improperly as the strength of the knot in such situations may be significantly lower than the tensile strength of the suture material.

To improve on these uses, sutures having a single preformed loop have been provided. FIG. 1 represents a prior art suture construction. As shown, one end of the suture is passed through a passage defined in the suture itself. The application of tension to the ends of the suture pulls a portion of the suture through the passage, causing a loop formed in the suture to close. Relaxation of the system, however may allow a portion of the suture to translate back through the passage, thus relieving the desired tension.

It is an object of the present teachings to provide an alternative device for anchoring sutures to bone and soft tissue. The device, which is relatively simple in design and structure, is highly effective for its intended purpose.

SUMMARY

This section provides a general summary of the disclosure, and is not a comprehensive disclosure of its full scope or all of its features.

The present teachings provide for a method for coupling soft tissue to bone. The method includes the following: forming a first bore in a bone; forming a second bore in the bone; positioning a first anchor in the first bore, the first anchor having a first self-locking adjustable suture construct extending therefrom, the first construct including a first adjustable loop, a second adjustable loop, and a pair of first ends; positioning a second anchor in the second bore, the second anchor having a second self-locking adjustable suture construct extending therefrom, the second construct including a third adjustable loop, and a second end; positioning the first adjustable loop relative to the soft tissue; positioning the second adjustable loop about the third adjustable loop; and tensioning the pair of first ends and the second end to pull the first adjustable loop against the soft tissue, couple the second adjustable loop to the third adjustable loop, pull the second adjustable loop against the soft tissue, and pull the third adjustable loop against the soft tissue to thereby couple the soft tissue to the bone.

The present teachings also provide for a method for coupling soft tissue to bone that includes the following: inserting a first anchor in a first bone bore, the first anchor having a first self-locking adjustable suture construct extending therefrom, the first construct including a first adjustable loop, a second adjustable loop, and a pair of first ends; inserting a second anchor in a second bone bore, the second anchor having a second self-locking adjustable suture construct extending therefrom, the second construct including a third adjustable loop, and a second end; positioning the first adjustable loop relative to the soft tissue; compressing a first coupling element connected to the first adjustable loop against the soft tissue by tensioning the pair of first ends; and connecting the second adjustable loop to the third adjustable loop with a second coupling element and compressing both the second adjustable loop and the first adjustable loop against the soft tissue by tensioning the pair of first ends and the second end.

The present teachings further provide for a method for coupling soft tissue to bone including: positioning a first anchor in a first bone bore, the first anchor having a first self-locking adjustable suture construct extending therefrom, the first construct including a first adjustable loop, a second adjustable loop, and a pair of first ends; positioning a second anchor in a second bone bore, the second anchor having a second self-locking adjustable suture construct extending therefrom, the second construct including at least a third adjustable loop, and at least one second end; positioning the first adjustable loop about a first portion of the soft tissue; collapsing a first coupling element connected to the first adjustable loop against the soft tissue by tensioning the pair of first ends; collapsing a second coupling element connected to the third adjustable loop against the second adjustable loop to couple the second adjustable loop to the third adjustable loop by tensioning the second end; and compressing the second adjustable loop and the third adjustable loop against the soft tissue by tensioning both the pair of first ends and the second end.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
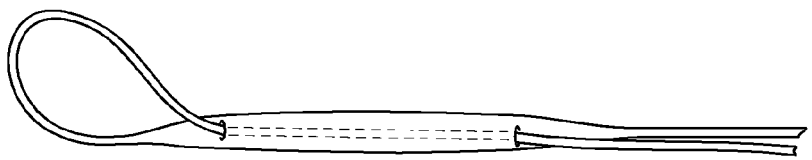
FIG. 1 represents a prior art suture configuration.

The following description is merely exemplary in nature and is not intended to limit the present disclosure, application, or uses. It should be understood that throughout the drawings, corresponding reference numerals indicate like or corresponding parts and features.

Figure 2A:
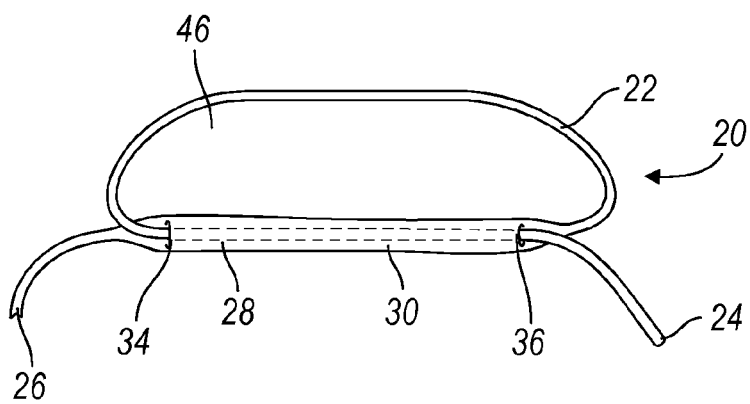
FIGS. 2A and 2B represent suture constructions according to the teachings.

FIG. 2A represents a suture construction 20 according to the present teachings. Shown is a suture 22 having a first end 24 and a second end 26. The suture 22 is formed of a braided body 28 that defines a longitudinally formed hollow passage 30 therein. First and second apertures 32 and 34 are defined in the braided body 28 at first and second locations of the longitudinally formed passage 30.

Figure 2B:
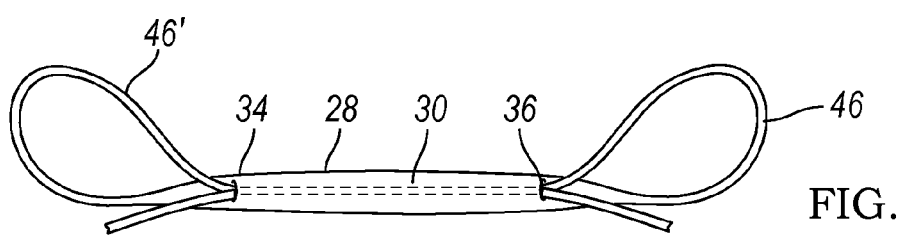
Figure 3:
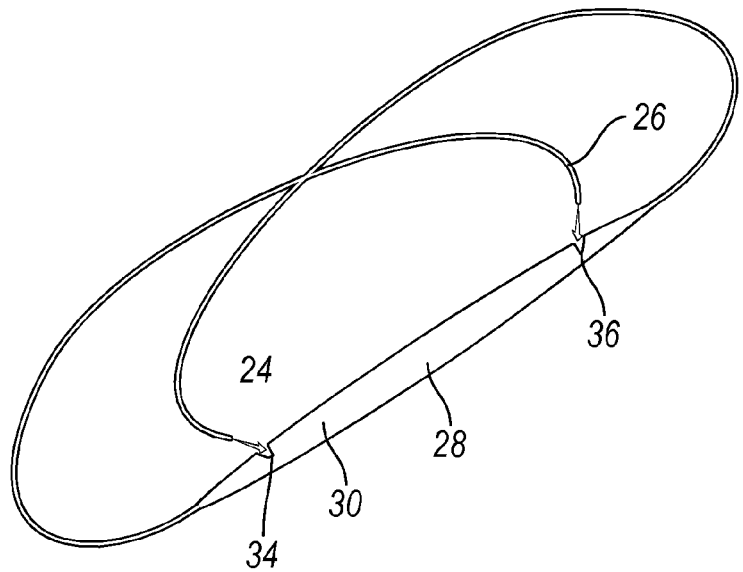
FIG. 3 represents the formation of the suture configuration shown in FIG. 2A.

Briefly referring to FIG. 3, a first end 24 of the suture 22 is passed through the first aperture 32 and through longitudinal passage 30 formed by a passage portion and out the second aperture 34. The second end 26 is passed through the second aperture 34, through the passage 30 and out the first aperture 32. This forms two loops 46 and 46'. As seen in FIG. 2B, the relationship of the first and second apertures 32 and 34 with respect to the first and second ends 24 and 26 can be modified so as to allow a bow-tie suture construction 36. As described below, the longitudinal and parallel placement of first and second suture portions 38 and 40 of the suture 22 within the longitudinal passage 30 resists the reverse relative movement of the first and second portions 38 and 40 of the suture once it is tightened.

The first and second apertures are formed during the braiding process as loose portions between pairs of fibers defining the suture. As further described below, the first and second ends 24 and 26 can be passed through the longitudinal passage 30 multiple times. It is envisioned that either a single or multiple apertures can be formed at the ends of the longitudinally formed passage.

Figure 4A:
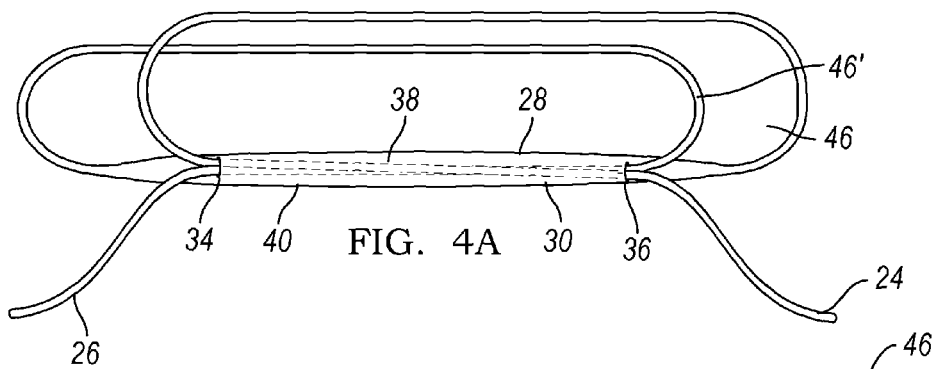
FIGS. 4A and 4B represent alternate suture configurations.
Figure 4B:
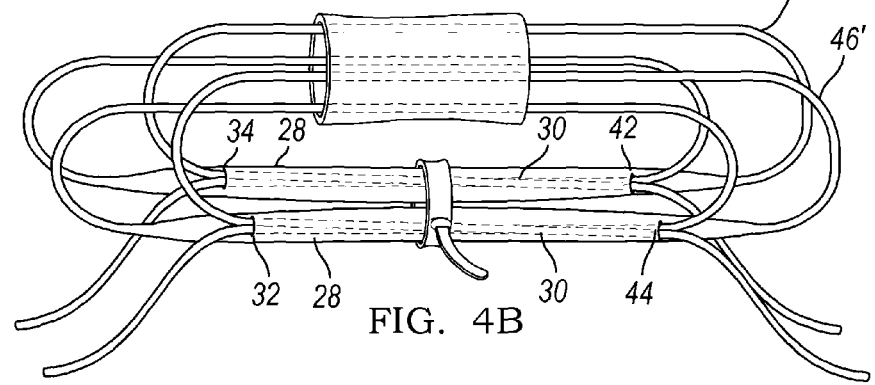

As best seen in FIGS. 4A and 4B, a portion of the braided body 28 of the suture defining the longitudinal passage 30 can be braided so as to have a diameter larger than the diameter of the first and second ends 24 and 26. Additionally shown are first through fourth apertures 32, 34, 42, and 44. These apertures can be formed in the braiding process or can be formed during the construction process. In this regard, the apertures 32, 34, 42, and 44 are defined between adjacent fibers in the braided body 28. As shown in FIG. 4B, and described below, it is envisioned the sutures can be passed through other biomedically compatible structures.

Figure 5:
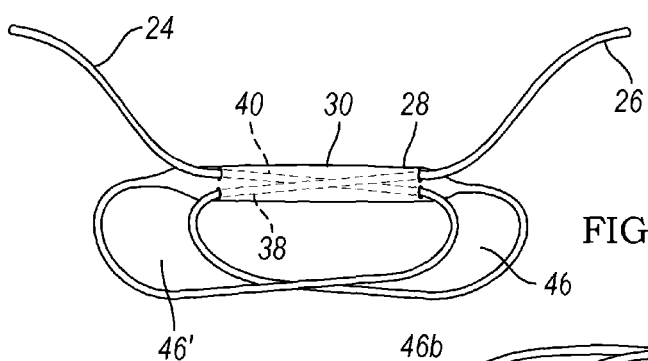
FIGS. 5-7 represent further alternate suture configurations.
Figure 6:
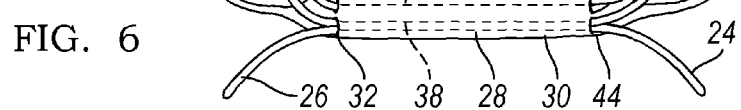
Figure 7:
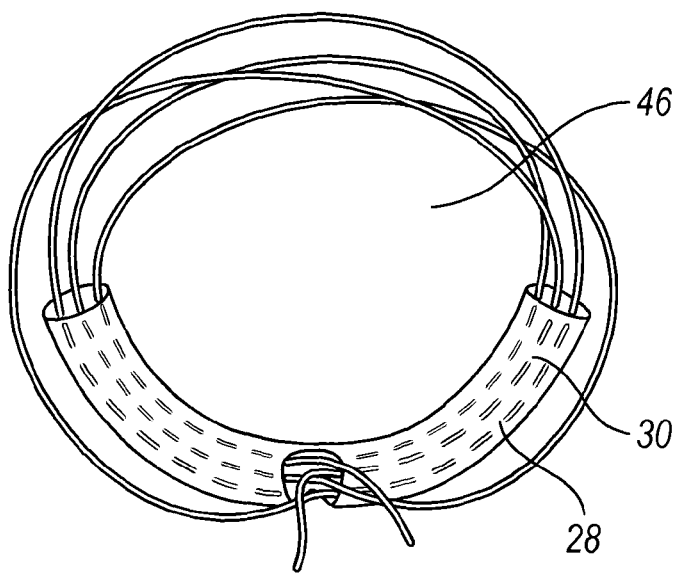
Figure 8:
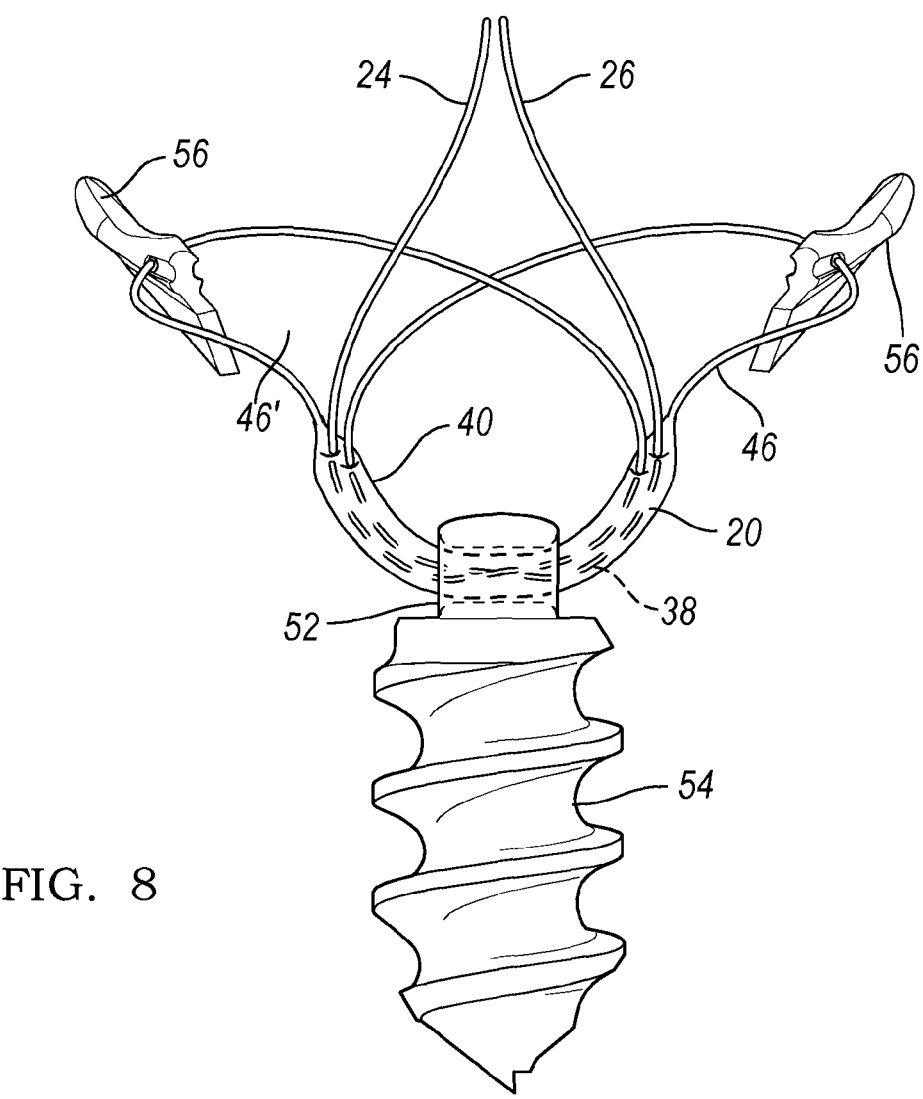
FIG. 8 represents the suture construction according to FIG. 5 coupled to a bone engaging fastener.
Figure 9:
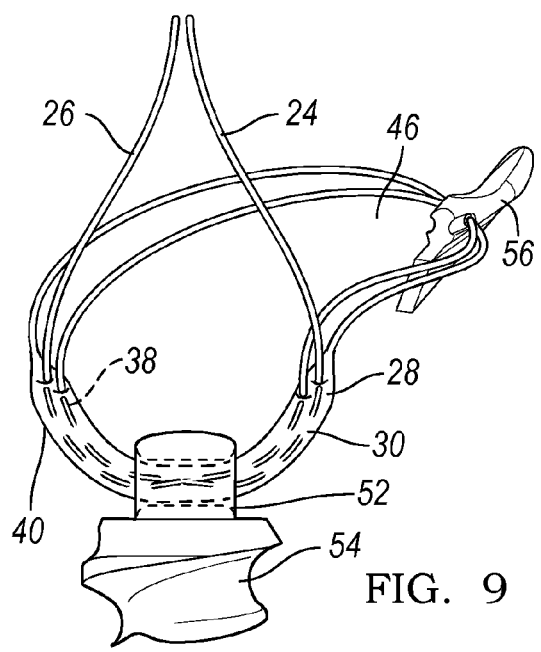
FIGS. 9-11B represent the coupling of the suture construction according to FIG. 5 to a bone screw.
Figure 10:
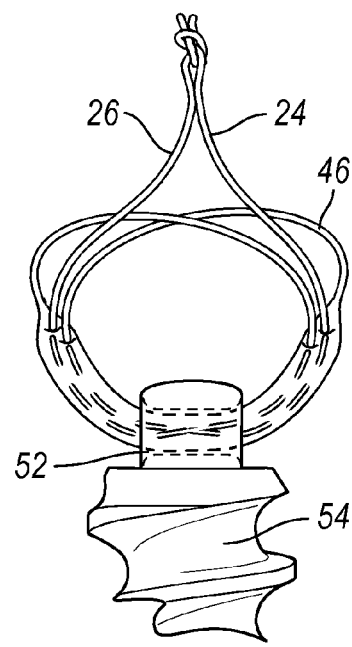

FIGS. 5-7 represent alternate constructions wherein a plurality of loops 46a-d are formed by passing the first and second ends 24 and 26 through the longitudinal passage 30 multiple times. The first and second ends 24 and 26 can be passed through multiple or single apertures defined at the ends of the longitudinal passage 30. The tensioning of the ends 24 and 26 cause relative translation of the sides of the suture with respect to each other.

Upon applying tension to the first and second ends 24 and 26 of the suture 22, the size of the loops 46a-d is reduced to a desired size or load.

At this point, additional tension causes the body of the suture defining the longitudinal passage 30 to constrict about the parallel portions of the suture within the longitudinal passage 30. This constriction reduces the diameter of the longitudinal passage 30, thus forming a mechanical interface between the exterior surfaces of the first and second parallel portions as well as the interior surface of the longitudinal passage 30.

As seen in FIGS. 8-11, the suture construction can be coupled to various biocompatible hardware. In this regard, the suture construction 20 can be coupled to an aperture 52 of the bone engaging fastener 54. Additionally, it is envisioned that soft tissue or bone engaging members 56 can be fastened to one or two loops 46. After fixing the bone engaging fastener 54, the members 56 can be used to repair, for instance, a meniscal tear. The first and second ends 24, 26 are then pulled, setting the tension on the loops 46, thus pulling the meniscus into place. Additionally, upon application of tension, the longitudinal passage 30 is constricted, thus preventing the relaxation of the tension caused by relative movement of the first and second parallel portions 38, 40, within the longitudinal passage 30.

As seen in FIGS. 9-11B, the loops 46 can be used to fasten the suture construction 20 to multiple types of prosthetic devices. As described further below, the suture 22 can further be used to repair and couple soft tissues in an anatomically desired position. Further, retraction of the first and second ends allows a physician to adjust the tension on the loops between the prosthetic devices.

Figure 11A:
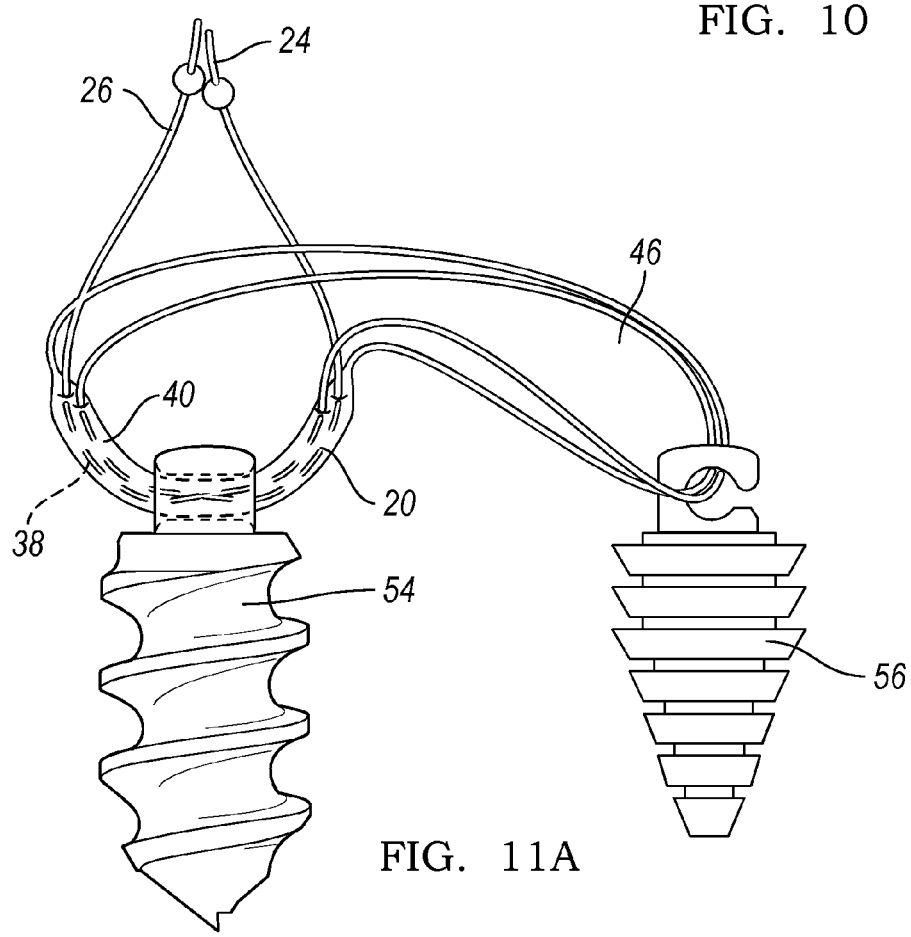
Figure 11B:
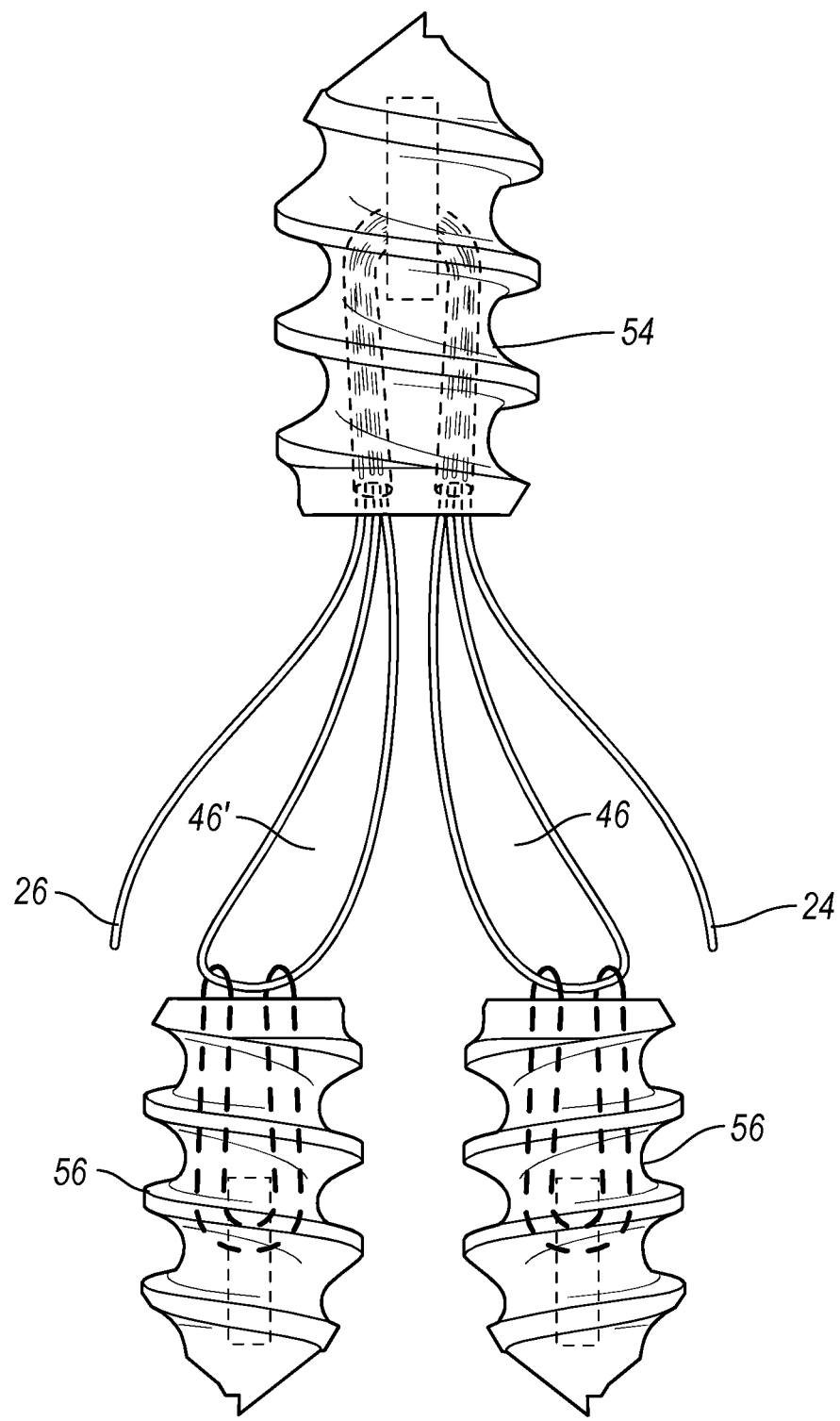

FIG. 11b represents the coupling of the suture construction according to FIG. 2B with a bone fastening member. Coupled to a pair of loops 46 and 46' are tissue fastening members 56. The application of tension to either the first or second end 24 or 26 will tighten the loops 46 or 46' separately.

Figure 12A:
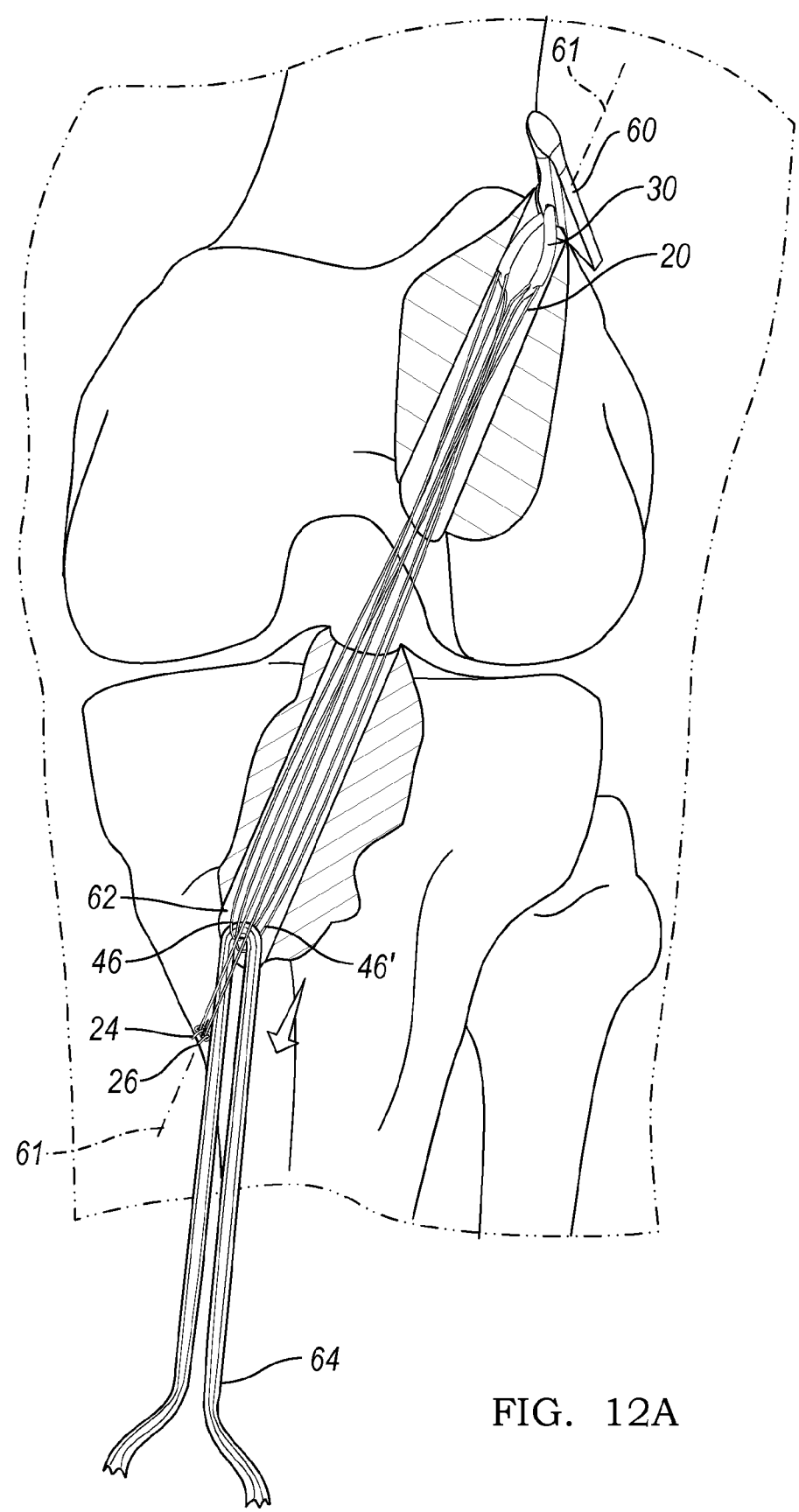
FIGS. 12A-12E represent the coupling of a soft tissue to an ACL replacement in a femoral/humeral reconstruction.
Figure 12B:
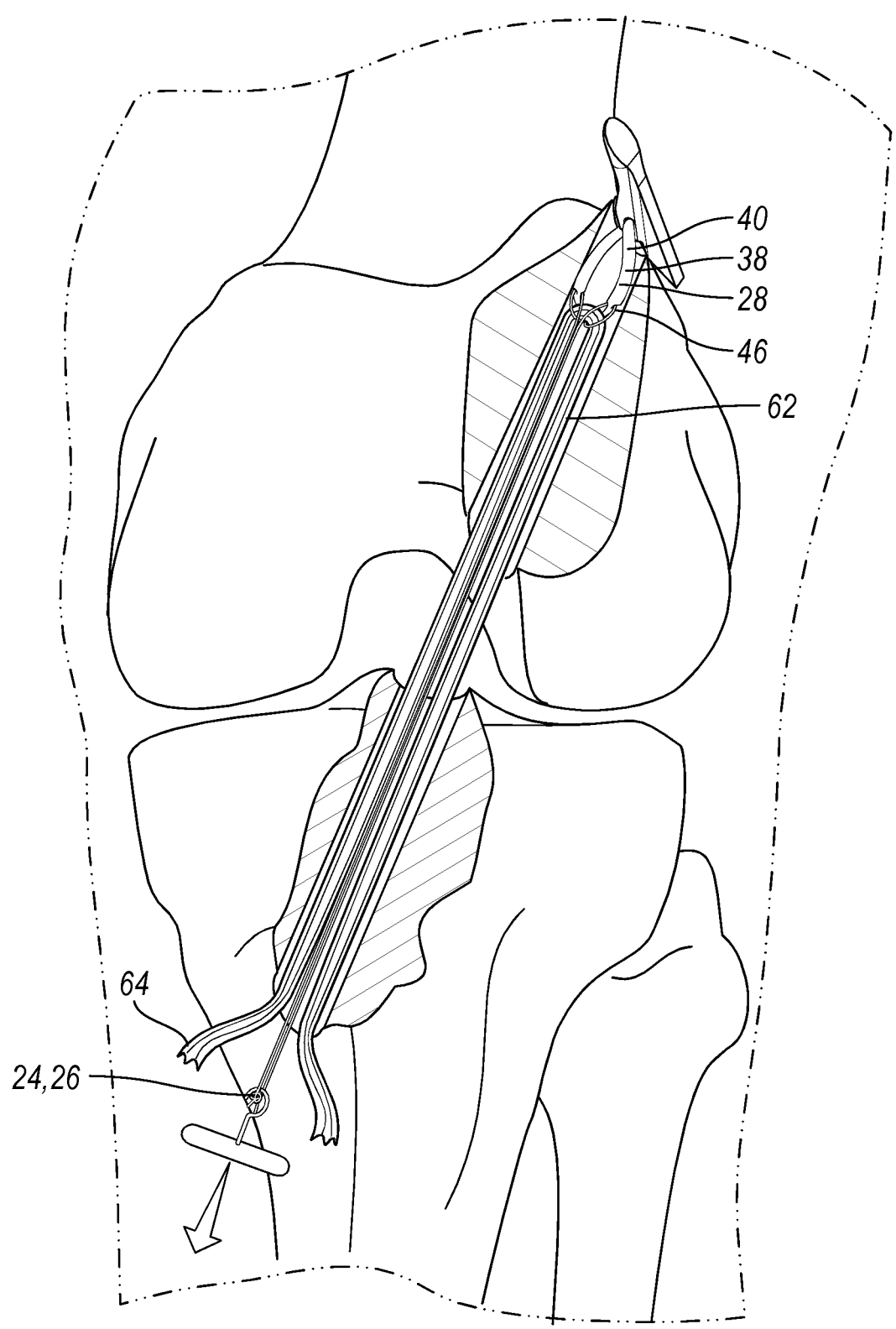

FIGS. 12A-12E represent potential uses of the suture constructions 20 in FIGS. 2A-7 in an ACL repair. As can be seen in FIG. 12A, the longitudinal passage portion 30 of suture construction 20 can be first coupled to a fixation member or fastener 60. The fixation member 60 can have a first profile which allows insertion of the fixation member 60 through the tunnel and a second profile which allows engagement with a positive locking surface upon rotation. The longitudinal passage portion 30 of the suture construction 20, fixation member 60, loops 46 and ends 24, 26 can then be passed through a femoral and tibial tunnel 62. The fixation member 60 is positioned or coupled to the femur. At this point, a natural or artificial ACL 64 can be passed through a loop or loops 46 formed in the suture construction 20. Tensioning of the first and second ends 24 and 26 applies tension to the loops 46, thus pulling the ACL 64 into the tunnel. In this regard, the first and second ends are pulled through the femoral and tibial tunnel, thus constricting the loops 46 about the ACL 64 (see FIG. 12B).

As shown, the suture construction 20 allows for the application of force along an axis 61 defining the femoral tunnel. Specifically, the orientation of the suture construction 20 and, more specifically, the orientation of the longitudinal passage portion 30, the loops 46, and ends 24, 26 allow for tension to be applied to the construction 20 without applying non-seating forces to the fixation member 60. As an example, should the loops 24, 26 be positioned at the fixation member 60, application of forces to the ends 24, 26 may reduce the seating force applied by the fixation member 60 onto the bone.

Figure 12C:
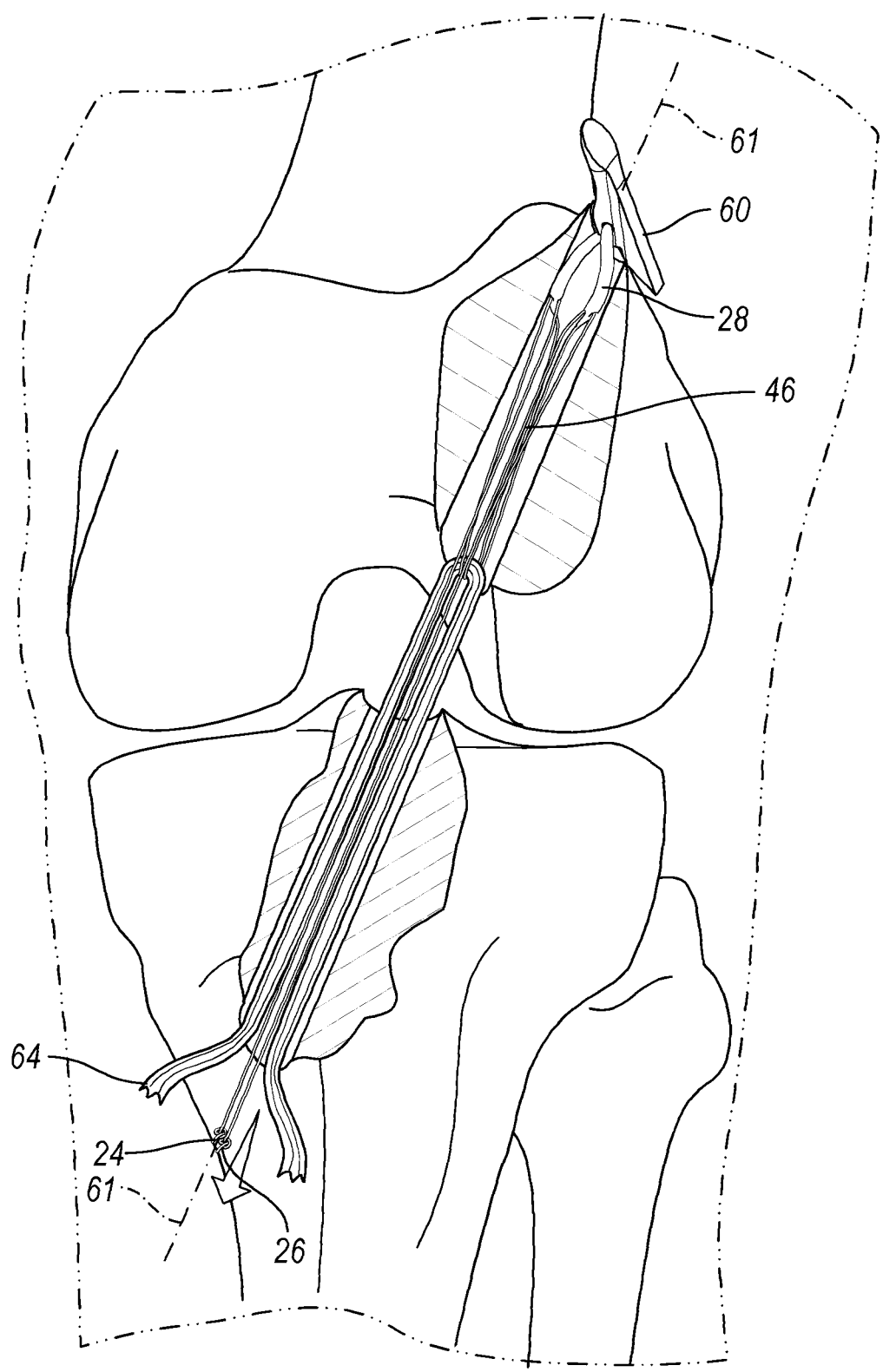
Figure 12D:
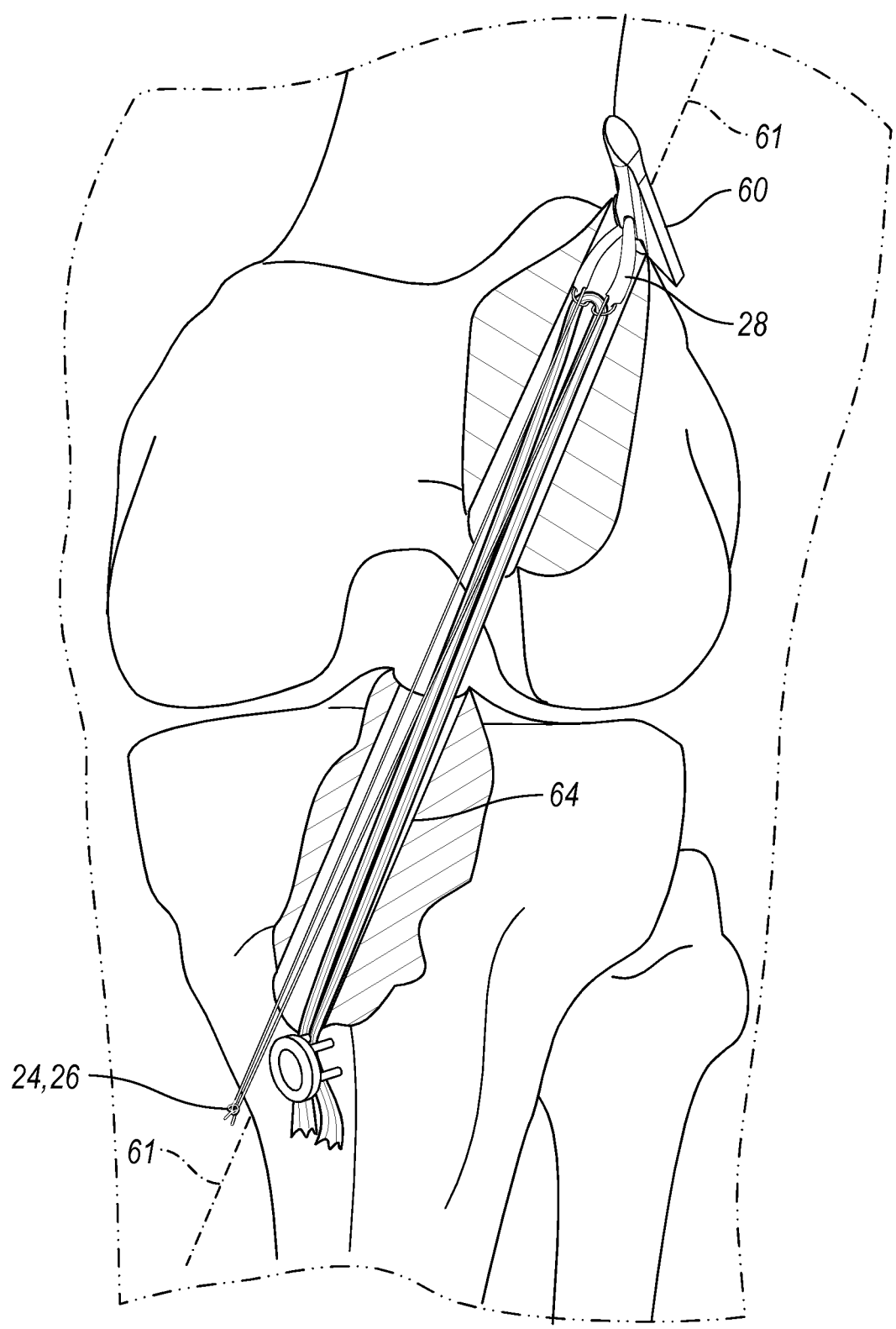

As best seen in FIG. 12C, the body portion 28 and parallel portions 38, 40 of the suture construction 20 remain disposed within to the fixation member 60. Further tension of the first ends draws the ACL 64 up through the tibial component into the femoral component. In this way, suture ends can be used to apply appropriate tension onto the ACL 64 component. The ACL 64 would be fixed to the tibial component using a plug or screw as is known.

Figure 12E:
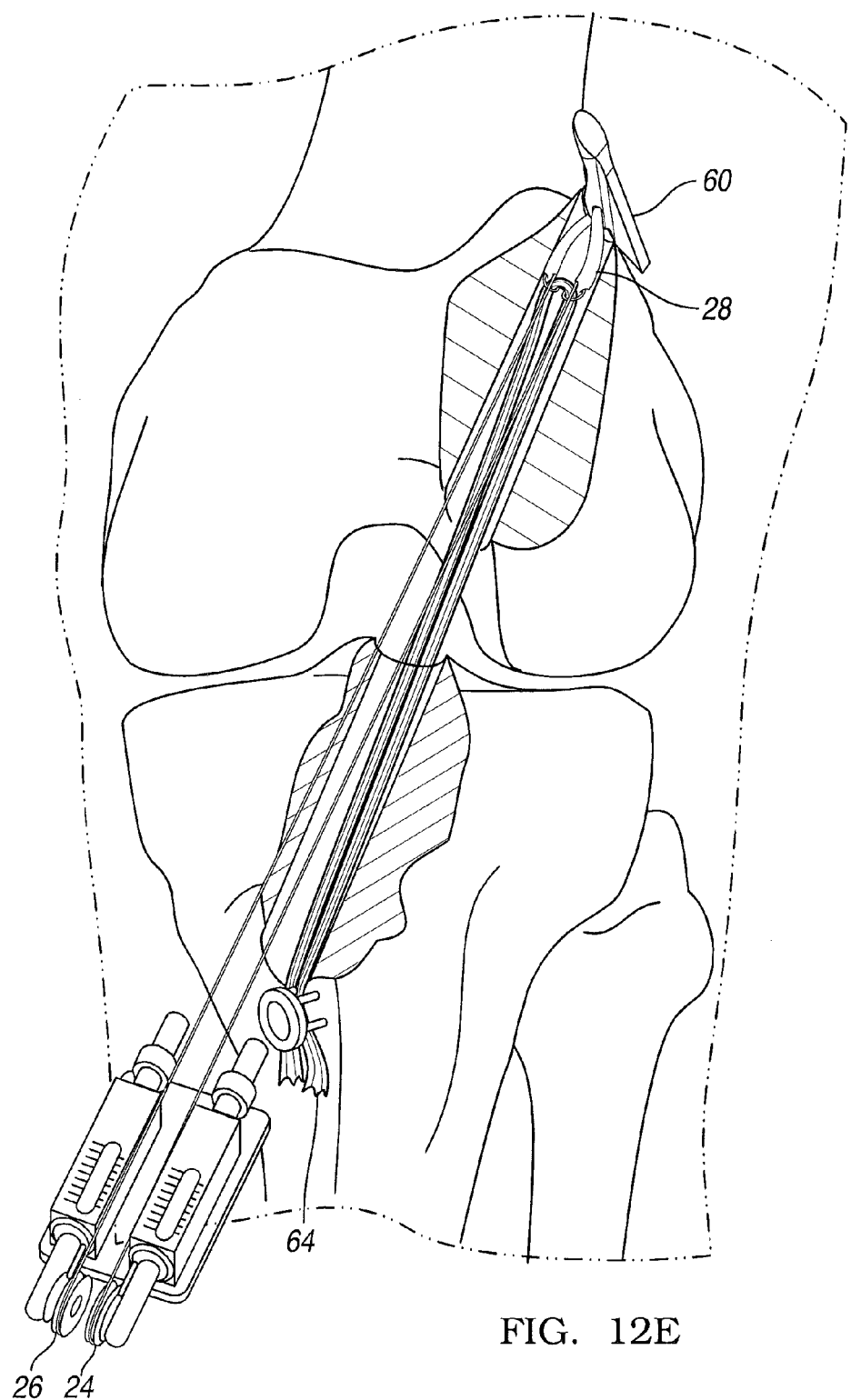
Figure 13A:
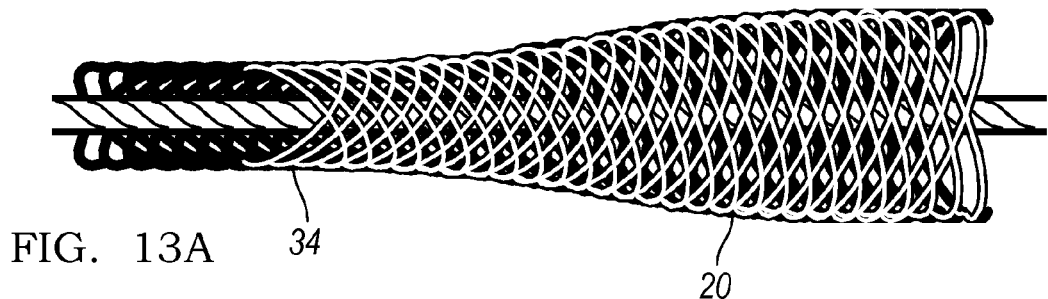
FIGS. 13A-13D represent a close-up view of the suture shown in FIGS. 1-11B.
Figure 13B:
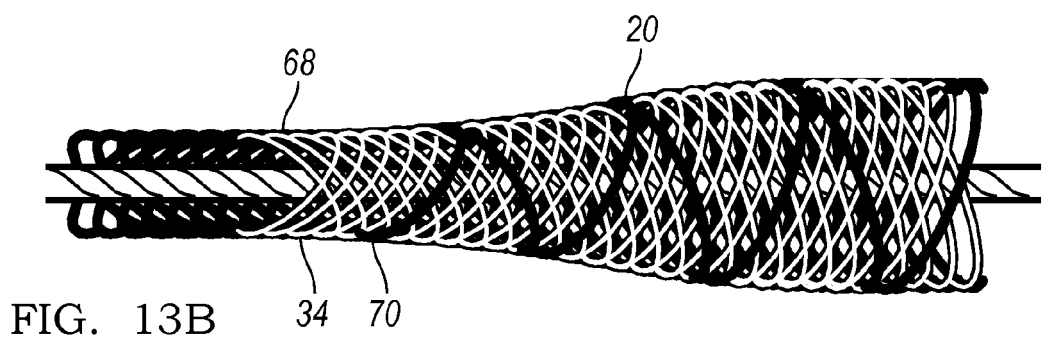
Figure 13C:
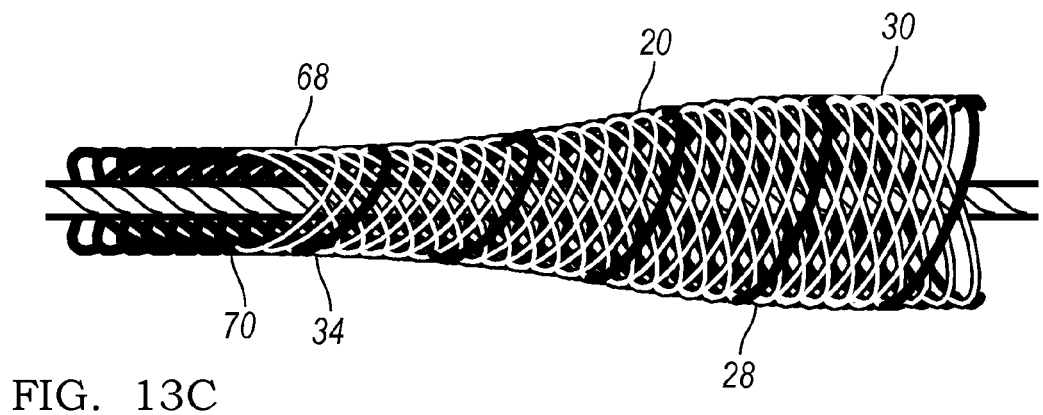
Figure 13D:
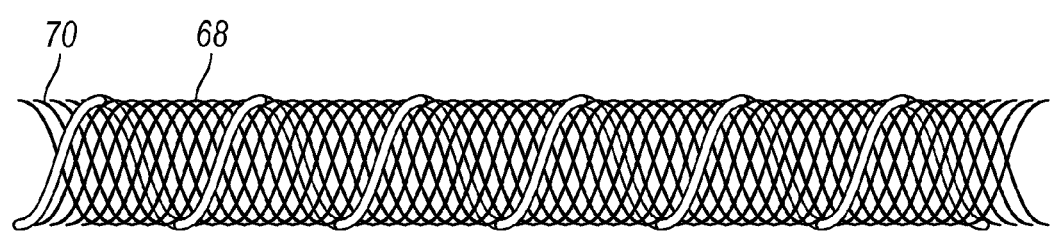

After feeding the ACL 64 through the loops 46, tensioning of the ends allows engagement of the ACL with bearing surfaces defined on the loops. The tensioning pulls the ACL 64 through a femoral and tibial tunnel. The ACL 64 could be further coupled to the femur using a transverse pin or plug. As shown in FIG. 12E, once the ACL is fastened to the tibia, further tensioning can be applied to the first and second ends 24, 26 placing a desired predetermined load on the ACL.

This tension can be measured using a force gauge. This load is maintained by the suture configuration. It is equally envisioned that the fixation member 60 can be placed on the tibial component 66 and the ACL pulled into the tunnel through the femur. Further, it is envisioned that bone cement or biological materials may be inserted into the tunnel 62.

FIGS. 13A-13D represent a close-up of a portion of the suture 20. As can be seen, the portion of the suture defining the longitudinal passage 30 has a diameter $d_1$ which is larger than the diameter $d_2$ of the ends 24 and 26. The first aperture 32 is formed between a pair of fiber members. As can be seen, the apertures 32, 34 can be formed between two adjacent fiber pairs 68, 70. Further, various shapes can be braided onto a surface of the longitudinal passage 30.

The sutures are typically braided of from 8 to 16 fibers. These fibers are made of nylon or other biocompatible material. It is envisioned that the suture 22 can be formed of multiple type of biocompatible fibers having multiple coefficients of friction or size. Further, the braiding can be accomplished so that different portions of the exterior surface of the suture can have different coefficients of friction or mechanical properties. The placement of a carrier fiber having a particular surface property can be modified along the length of the suture so as to place it at varying locations within the braided constructions.

Figure 14A:
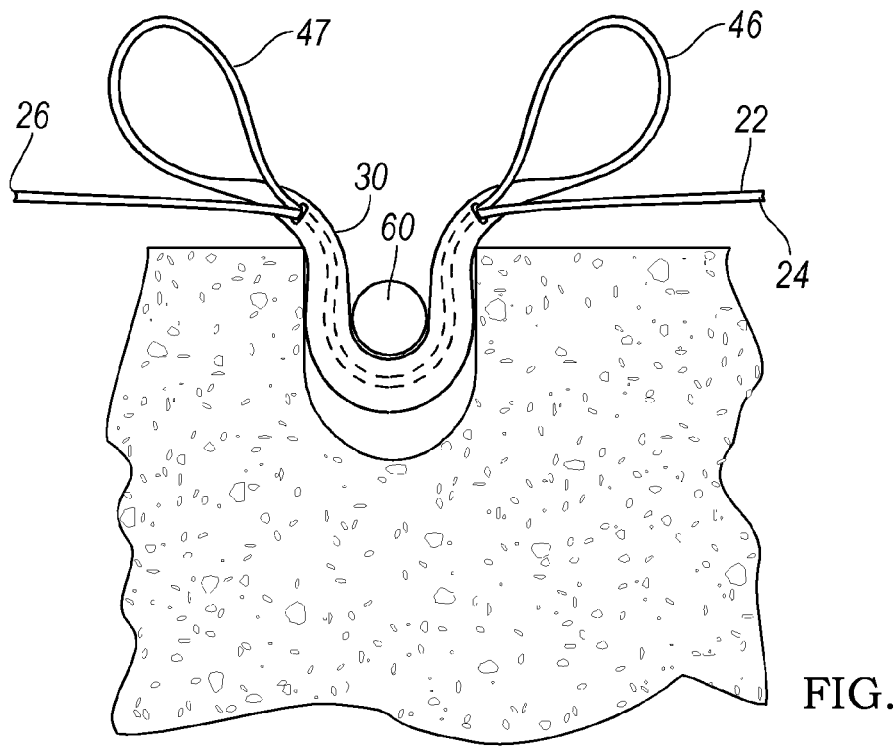
FIGS. 14A and 14B represent the coupling of the suture construction of FIG. 2A and FIG. 4 to bone.
Figure 14B:
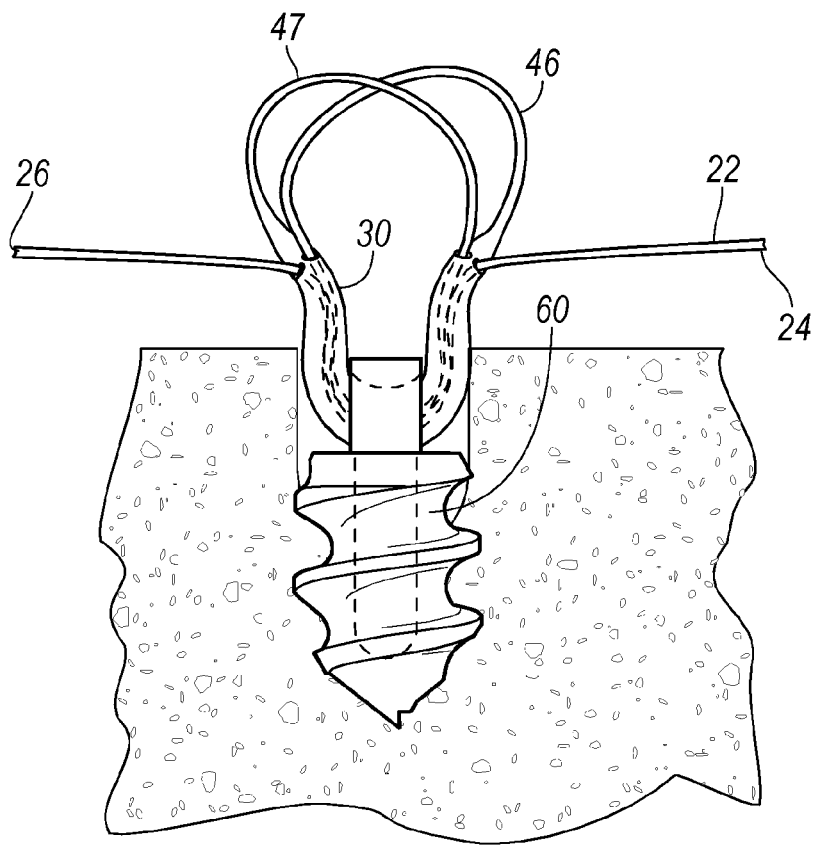

FIGS. 14A and 14B represent the coupling of suture construction 22 of FIG. 2A and FIG. 4 to a bone. The longitudinal passage 30 is coupled to a fixation member 60 which can be disposed within an aperture formed in the bone. The fixation member 60 can be, for example, a staple or a bone engaging screw. After coupling the suture construction 22 to the bone, loops 46 and 47 and ends 24 and 26 are readily accessible by the physician. The application of tension to the ends 24 and/or 26 causes the loops 46 and 47 to constrict. The loops 46 and 47 can be used to couple two or more portions of the anatomy. In this regard, the loops can be used to couple bone to bone or soft tissue to bone.

Figure 15A:
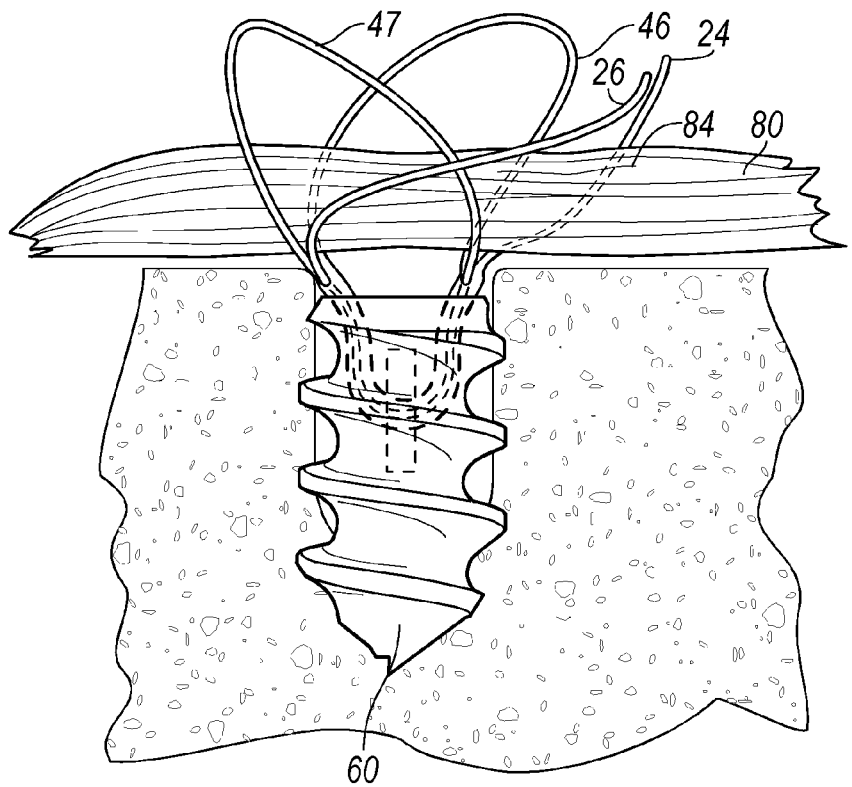
FIGS. 15A-15G represent the coupling of soft tissue to a bone according to the present teachings.
Figure 15B:
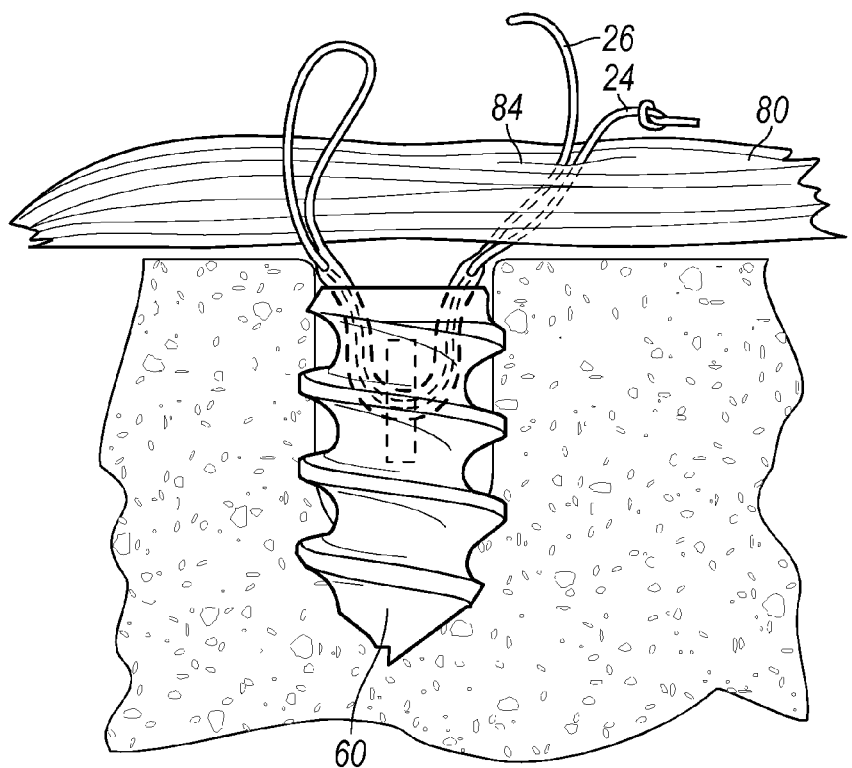

FIGS. 15A-15G represent the coupling of soft tissue 80 to bone. As shown in FIGS. 15A and 15B, the suture construction 22 is disposed about a portion of the soft tissue 80. Alternatively, an aperture or hole 84 can be formed in the soft tissue 80. A portion of the suture construction 22, for example, a loop 46 or loops 46, 47 or ends 24 and 26 can be threaded or pulled through the aperture 84. As seen in FIG. 15B, a single loop 46 of suture can be coupled to the fastener 60. This single loop 46 can be disposed over or around the soft tissue 80.

Figure 15C:
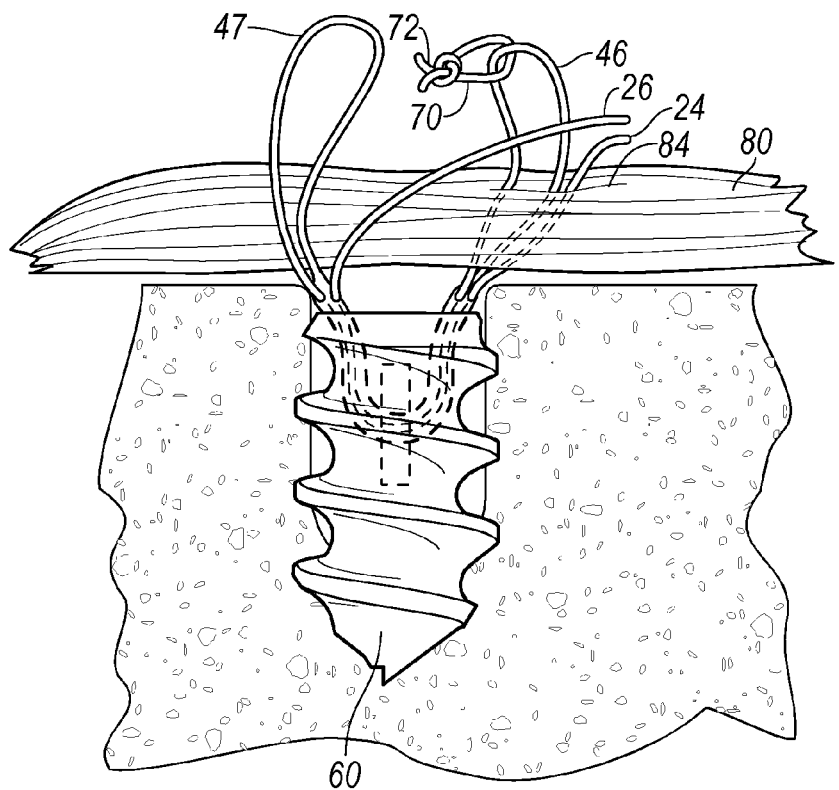

As shown in FIG. 15C, one loop 46 can have a fastening element 70 coupled thereto. This fastener element 70 can take the form of a loop of suture having a knot 72. This fastening element 70 along with the loop 46 and one or more strands 24 can be passed through the aperture 84 formed in the soft tissue 80.

Figure 15D:
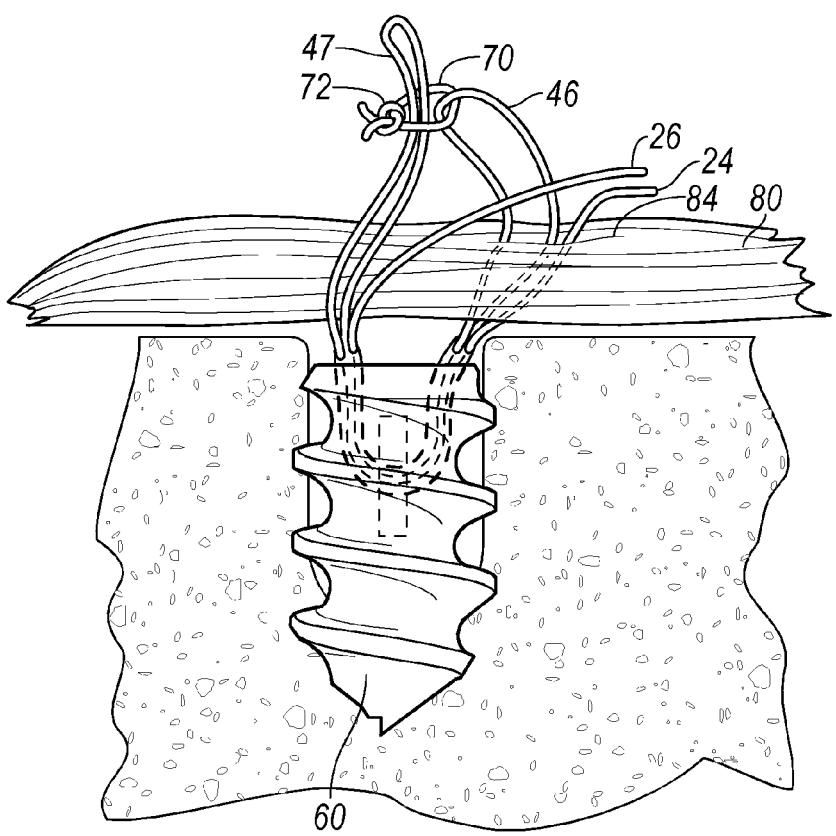

FIG. 15D shows the second loop 47 can be passed around the soft tissue and coupled to the fastening element 70. The first and second loops 46 and 47 are coupled together about the soft tissue 80, and optionally can be positioned about the knot 72.

Figure 15E:
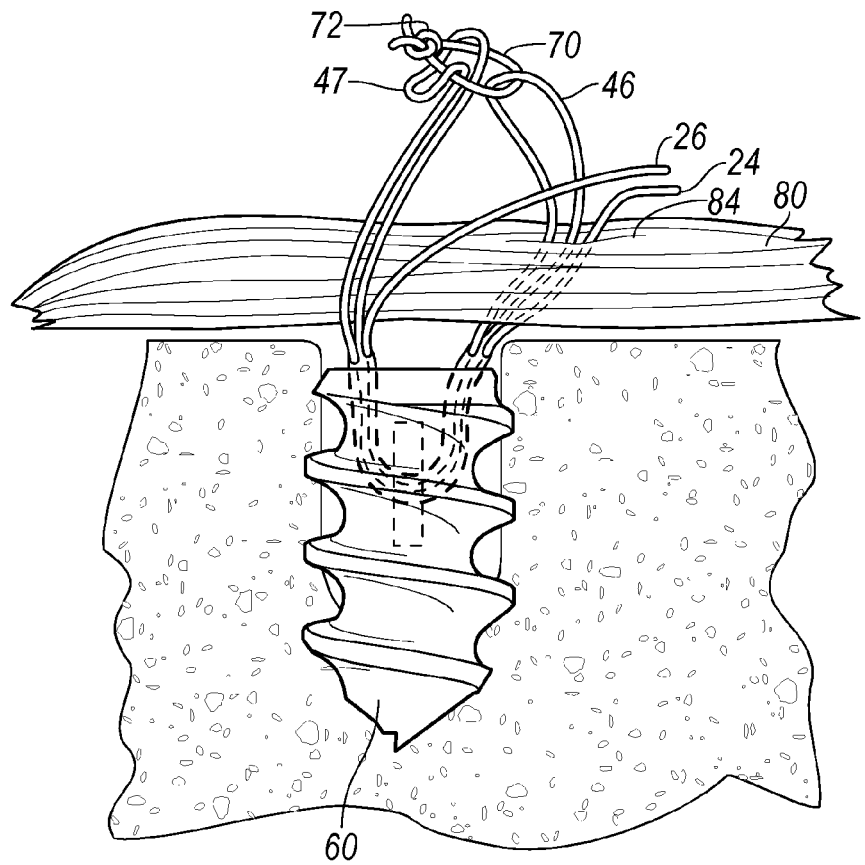
Figure 15F:
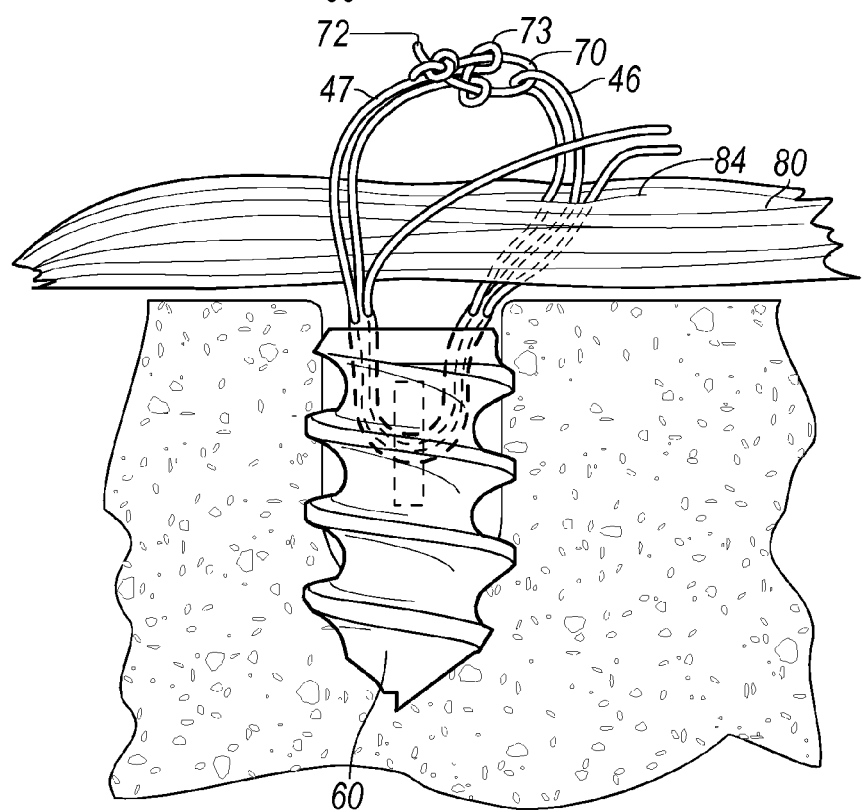
Figure 15G:
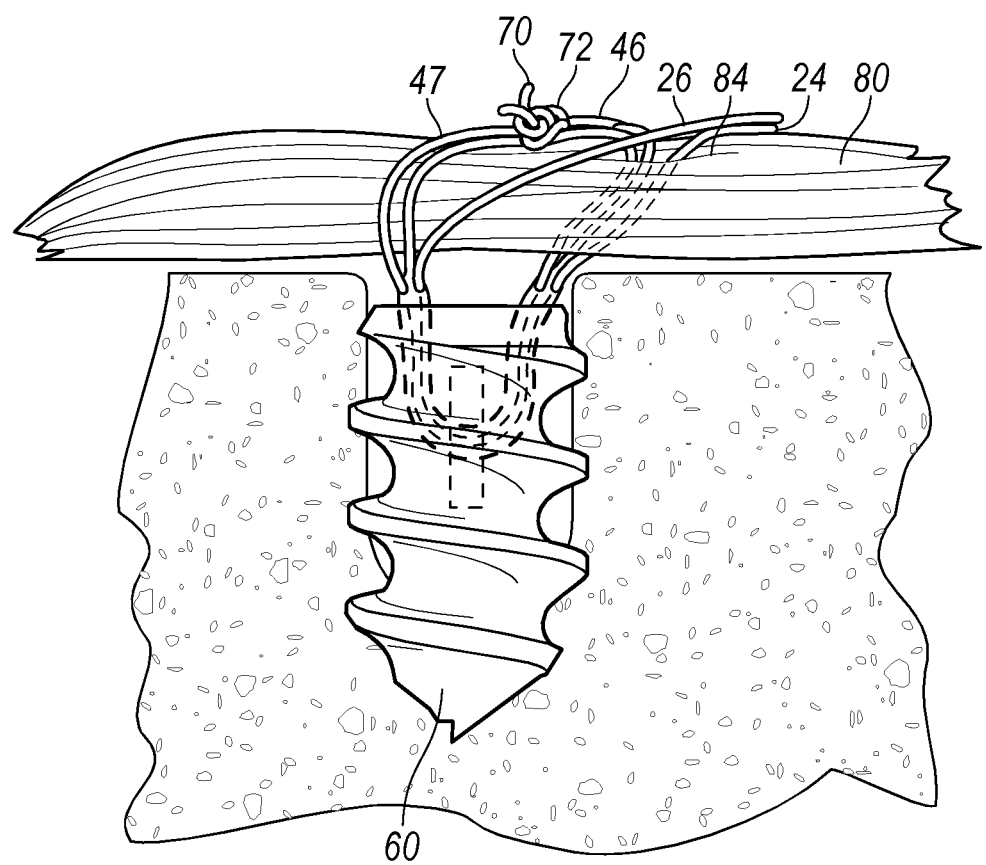

As shown in FIG. 15E, the first loop 46 and first end 24 can be passed through an aperture 84 of the soft tissue 80. Coupled to the first loop 46 is a fastener 70 in the form of a suture having a knot 72. The second loop 47 can be passed through the suture 70 and the knot 72 so as to form a pair of locking loops 73 (see FIG. 15F). FIG. 15G shows that tension can be applied to the first and second ends 24 and 26 of the suture 22 to constrict the suture 22 about the soft tissue

80. In this regard, the first and second loops 46 and 47 are tightened to constrict about and fix the soft tissue 80 to the bone.

Figure 16A:
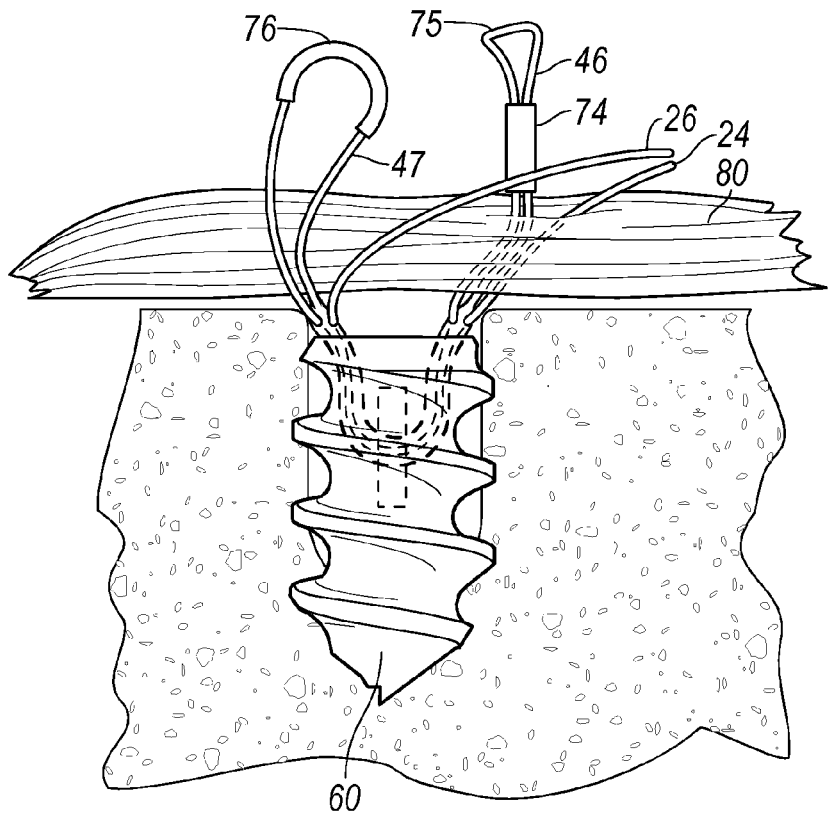
FIGS. 16A-16D represent the coupling of soft tissue to a bone using alternate teachings.

As seen in FIG. 16A, the construction of FIGS. 14A and 14B can be modified so as to place a pair of collapsible fabric tubes 74 and 76 about a portion of the suture 22. In this regard, collapsible tubes 74 and 76 can be coupled to the first and second suture loops 46 and 47. It is also envisioned several collapsible tubes can be coupled to a single loop 46 or the suture ends 26, 27.

Figure 16B:
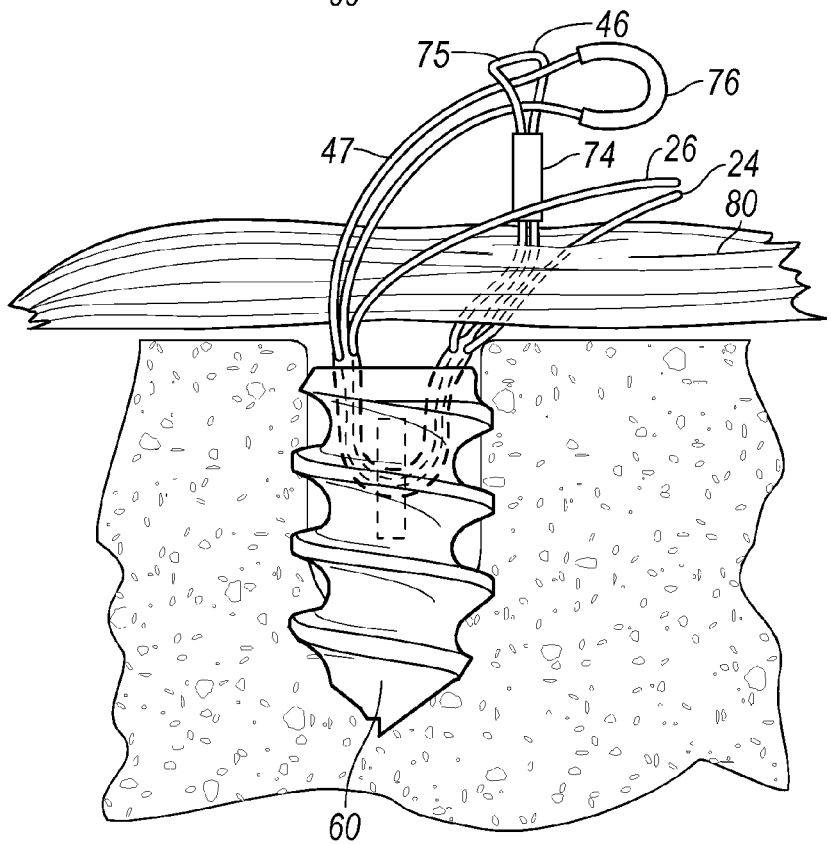
Figure 16C:
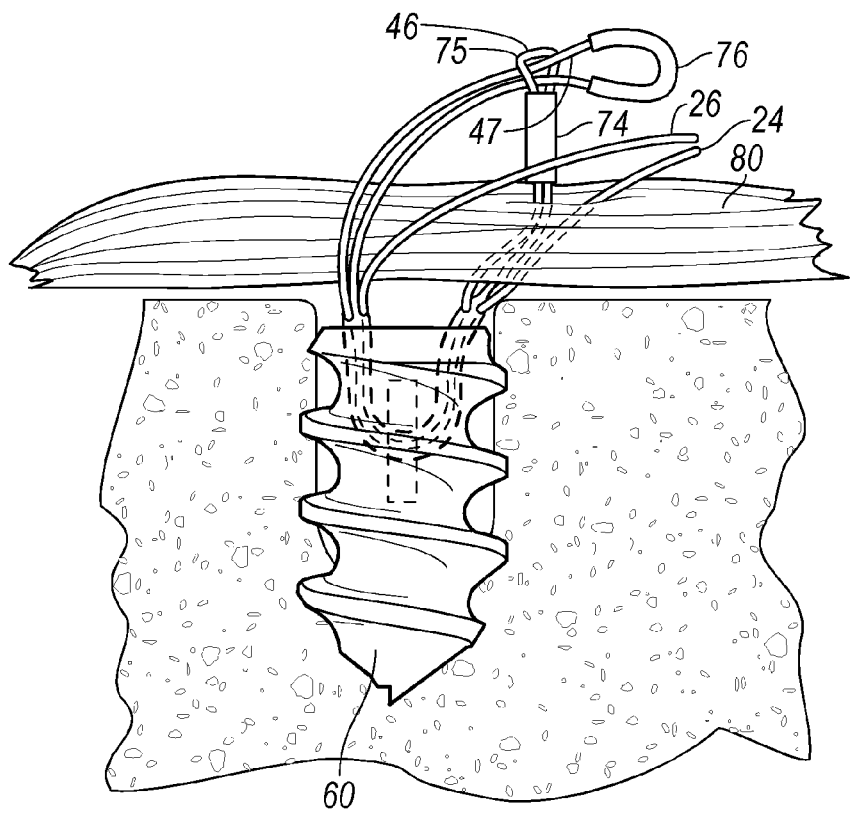
Figure 16D:
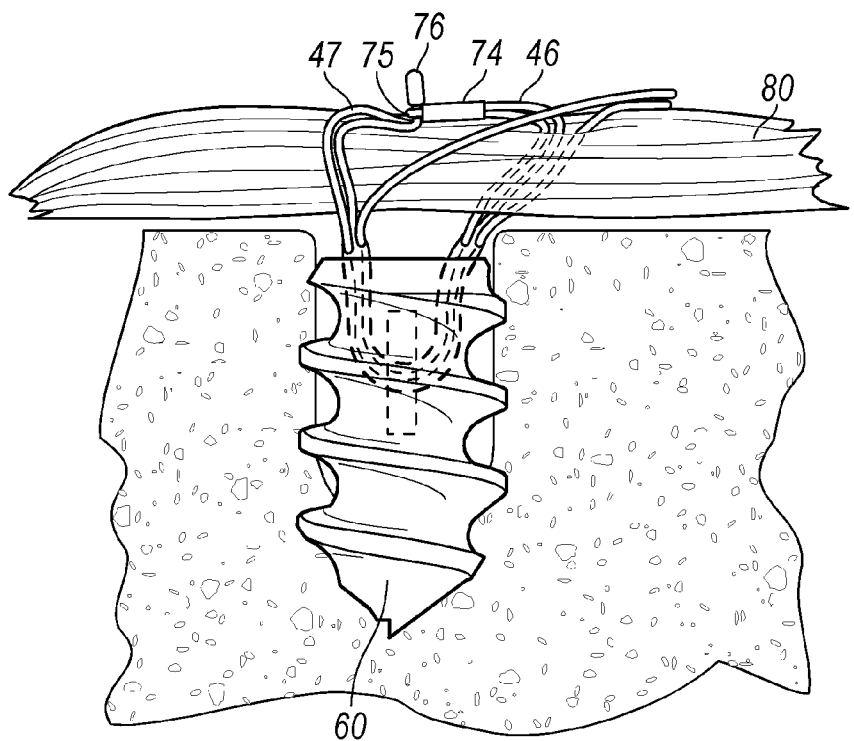

The collapsible tubes 74 and 76 can be either threaded onto (76) or disposed about a loop 75 formed in the suture loop 46. As seen in FIG. 16B, the first collapsible tube 76 can be fed through the loop 75. When tension is applied to the second end 26 of the sutures 47, the first loop 46 constricts about the second loop causing the collapse of the first collapsible tube 74. As shown in FIG. 16D, tension can be applied to the first suture end 24 causing the second loop 47 to constrict causing the collapse of the second collapsible tube 76 and the subsequent locking of the soft tissue 80 to the bone.

Figure 17A:
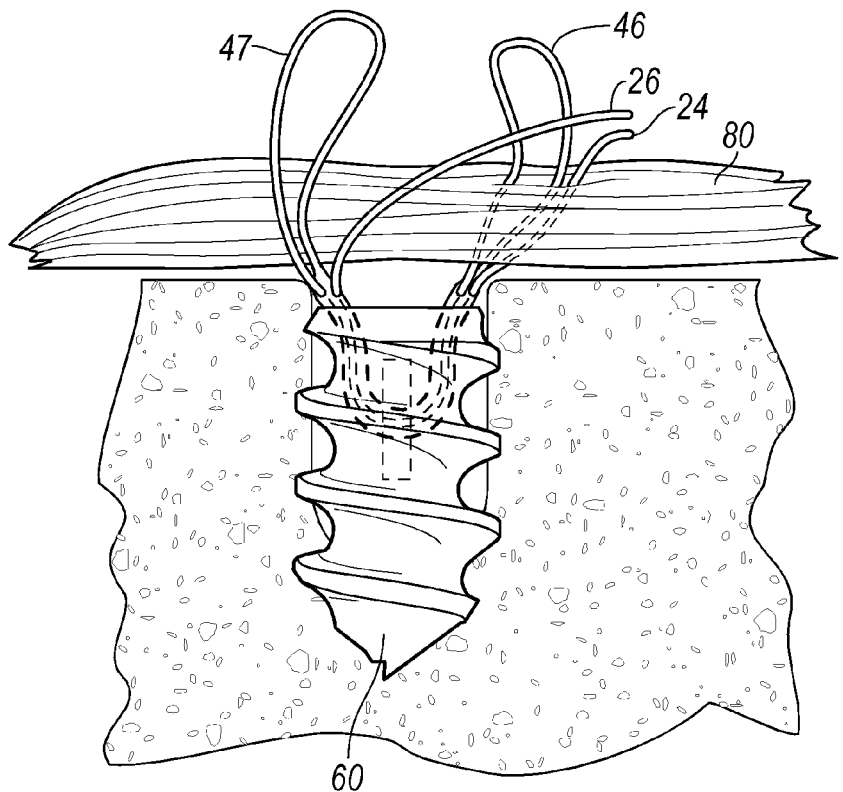
FIGS. 17A-17E represent the coupling of soft tissue to a bone using alternate teachings.
Figure 17B:
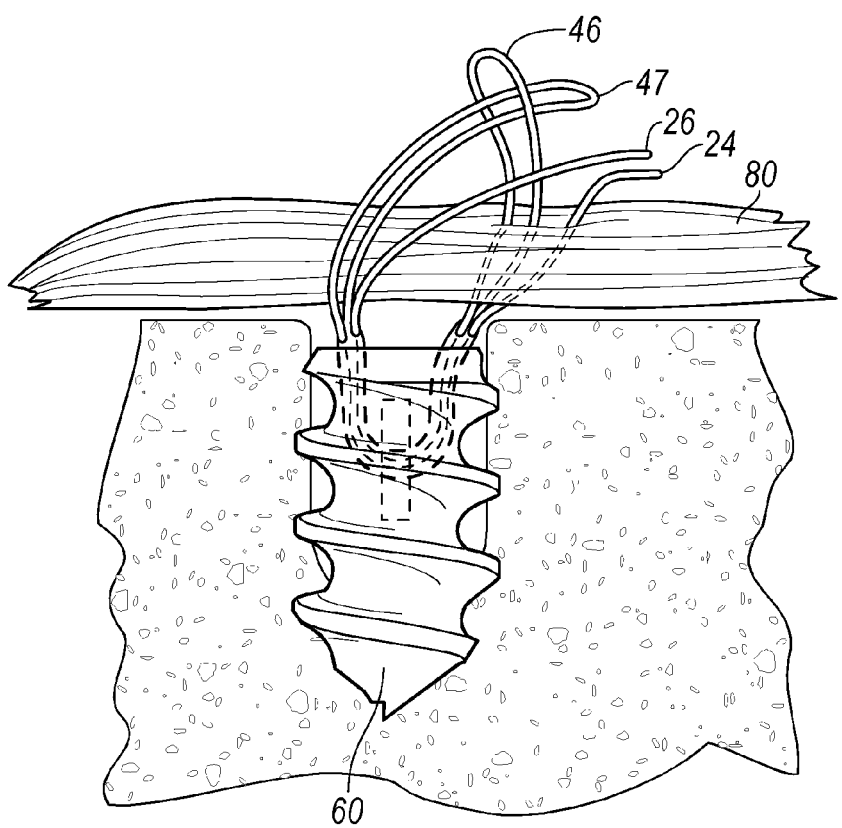
Figure 17C:
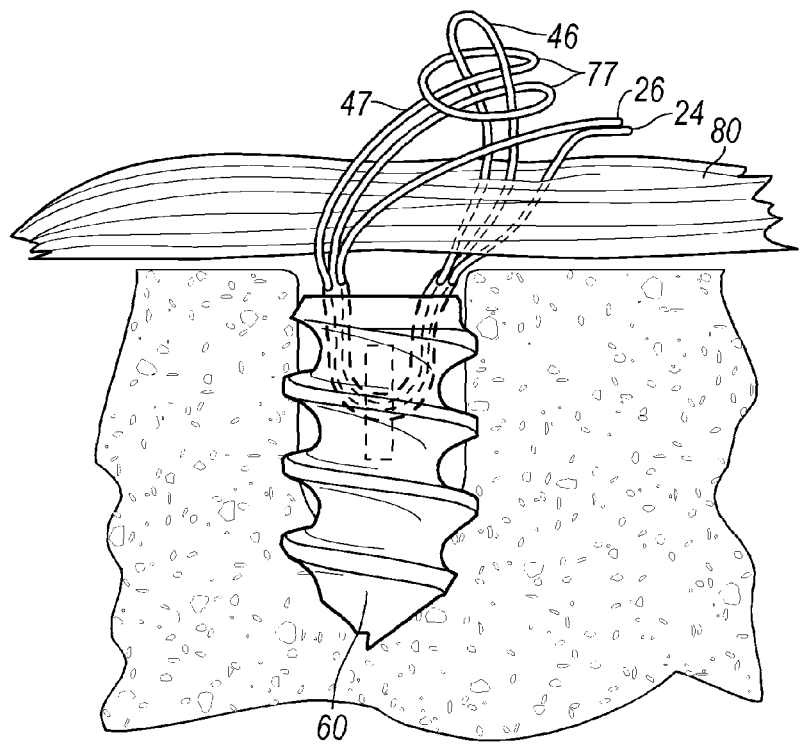

FIGS. 17A-17E represent an alternate method for coupling soft tissue 80 to a bone using the construction of FIGS. 14A and 14B. As shown in FIG. 17A, the first loop 46 and first suture end 24 are passed through an aperture 84 formed in the soft tissue 80. The second loop 47 is passed through the first loop 46.

Figure 17D:
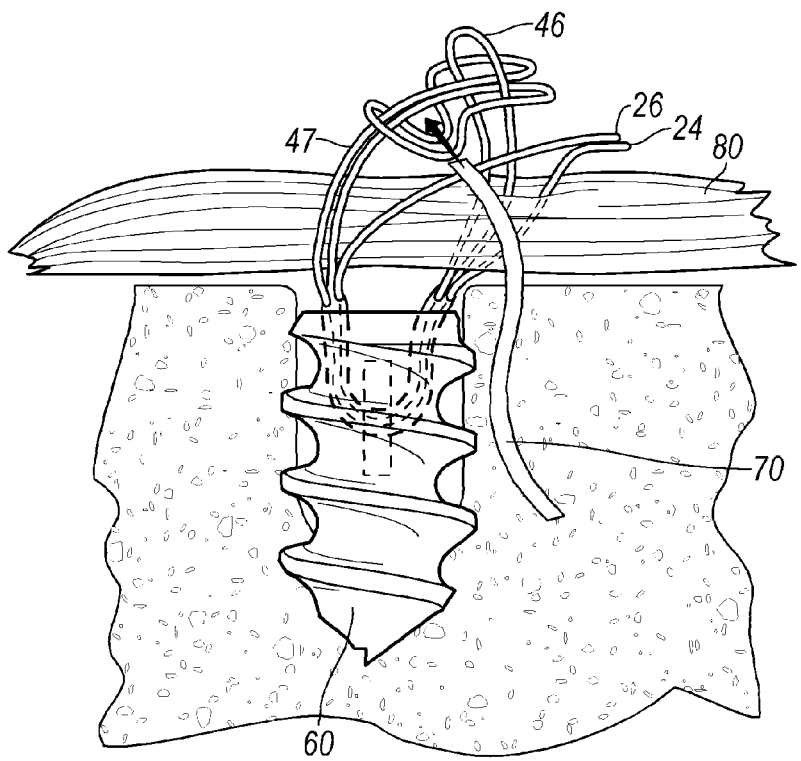
Figure 17E:
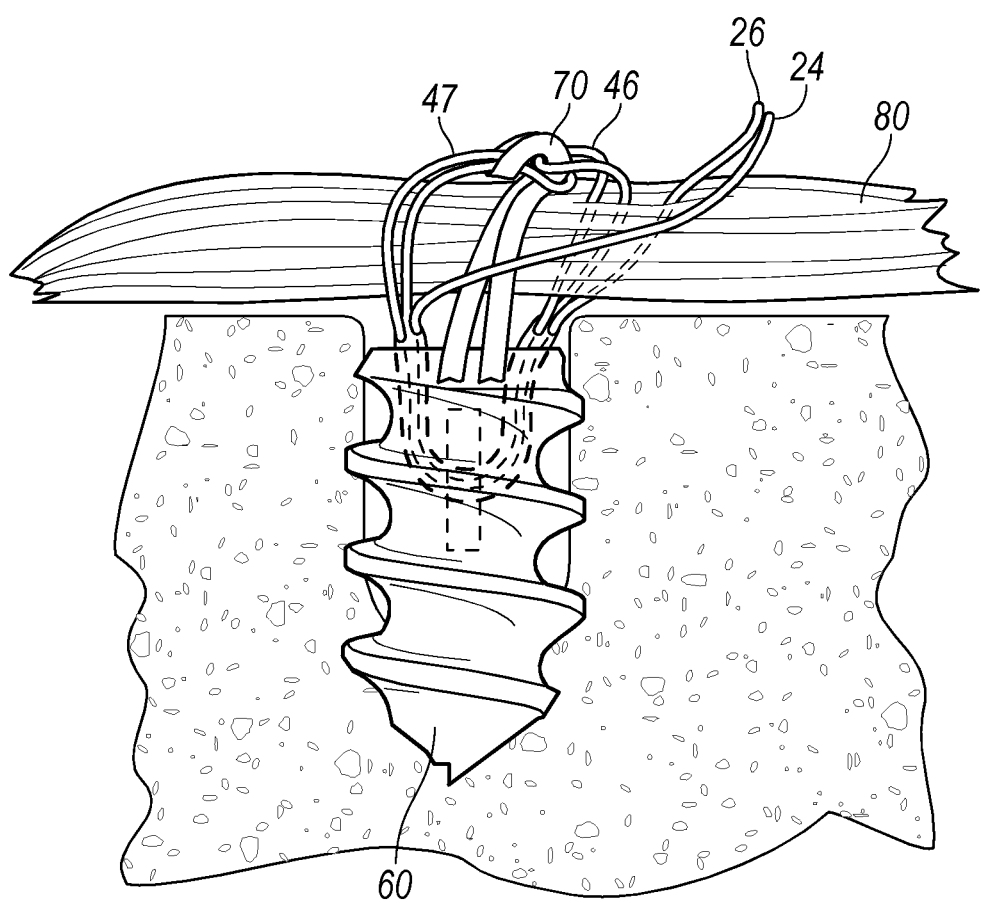

The second loop 47 is then doubled back over the first loop 46 causing a pair of intermediate loops 77. As shown in FIG. 17D, a locking member 70, soft or hard, can then be passed through the pair of intermediate loops 77 or a portion of the first loop 75 to lock the first and second loops 46 and 47 together. As shown in FIG. 17E, tension applied to the suture ends 26, 27 tighten the loops 46 and 47 about the locking member 70. The soft tissue 80 is also fixed to the bone.

Figure 18A:
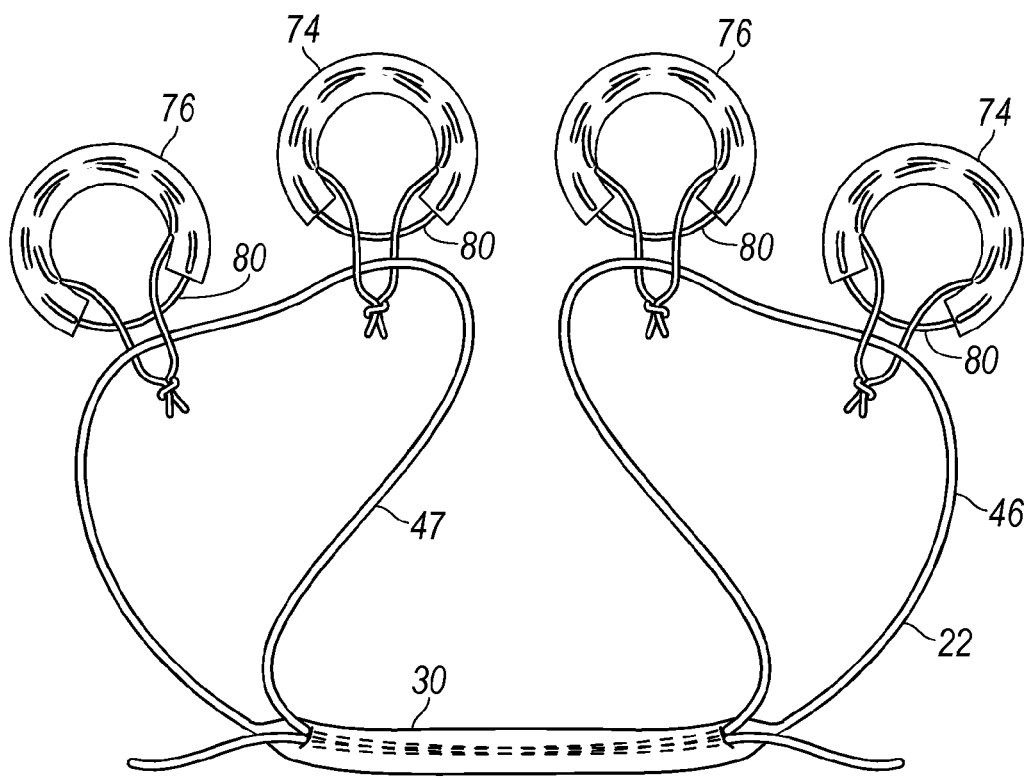
FIGS. 18A-18C represent the coupling of soft tissue to a bone using multiple collapsible loop structures.
Figure 18B:
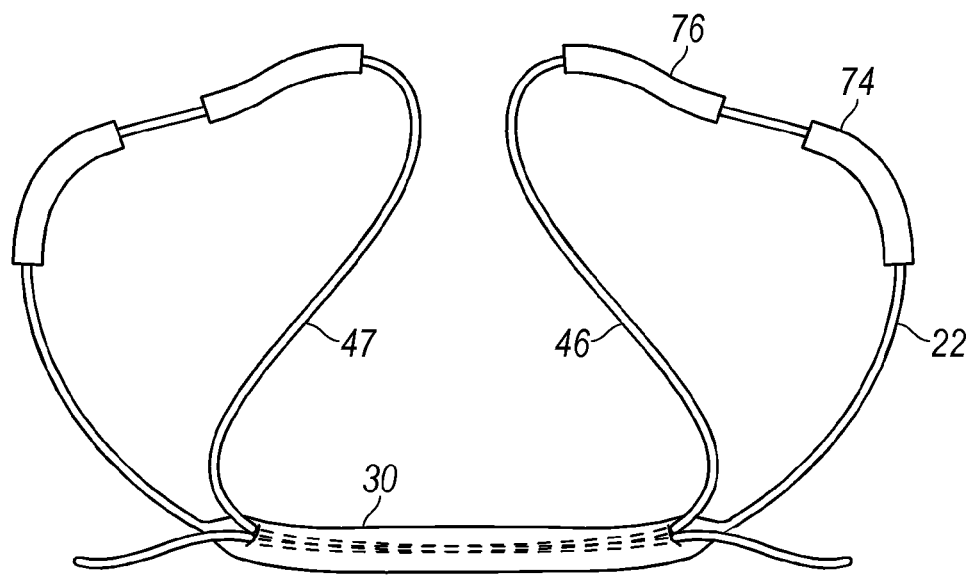
Figure 18C:
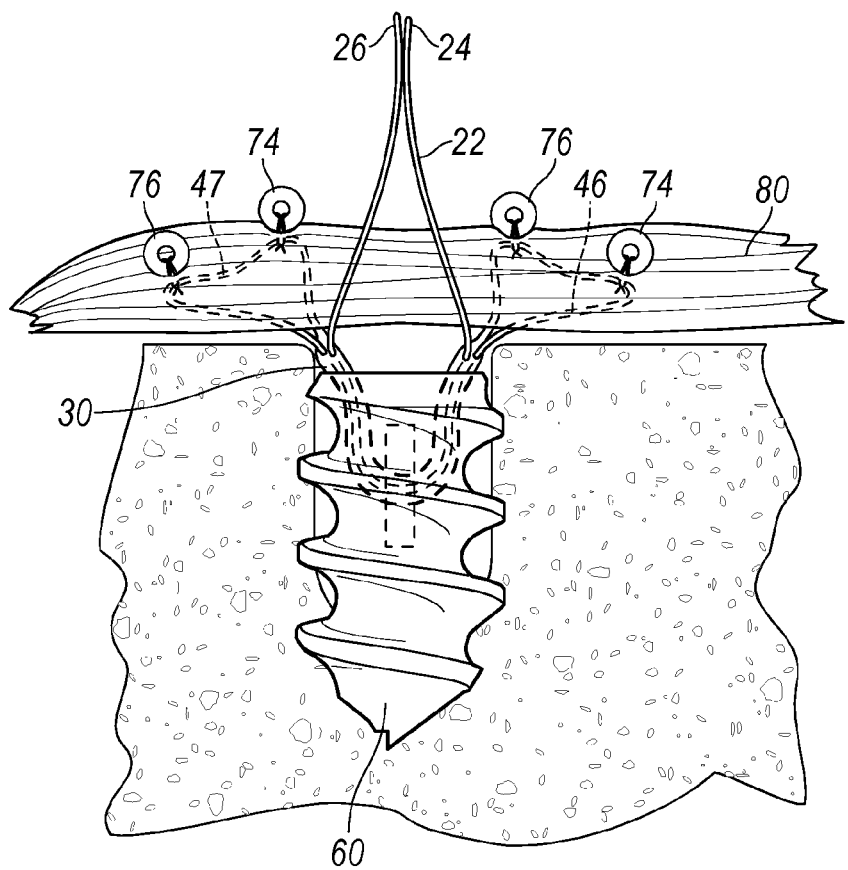

FIGS. 18A-18C represent alternate suture constructions 22 which are used to couple soft tissue 80 and 81 to bone. Disposed about the first and second loops 46 and 47 are collapsible tubes 74 and 76. The tubes 74 and 76 which can be, for example, fabric or polymer, can either be directly disposed about the suture 22 of the first and second loops 46 and 47, or can be coupled to the suture loops 46 and 47 using a separate loop member 81.

As shown in FIG. 18C, the suture construction 22 shown in FIGS. 18A or 18B, the collapsible tubes 74 and 76 are passed through the apertures 84 formed in the soft tissue 80. The application of tension to the ends 26 and 27 causes the soft tissue 80 to be drawn against the bone and cause compressive forces to be applied to the collapsible tubes 74 and 76. By tightening the suture which passes through the passage 30, the soft tissue 80 is coupled to the bone without the use of knots.

Figure 19A:
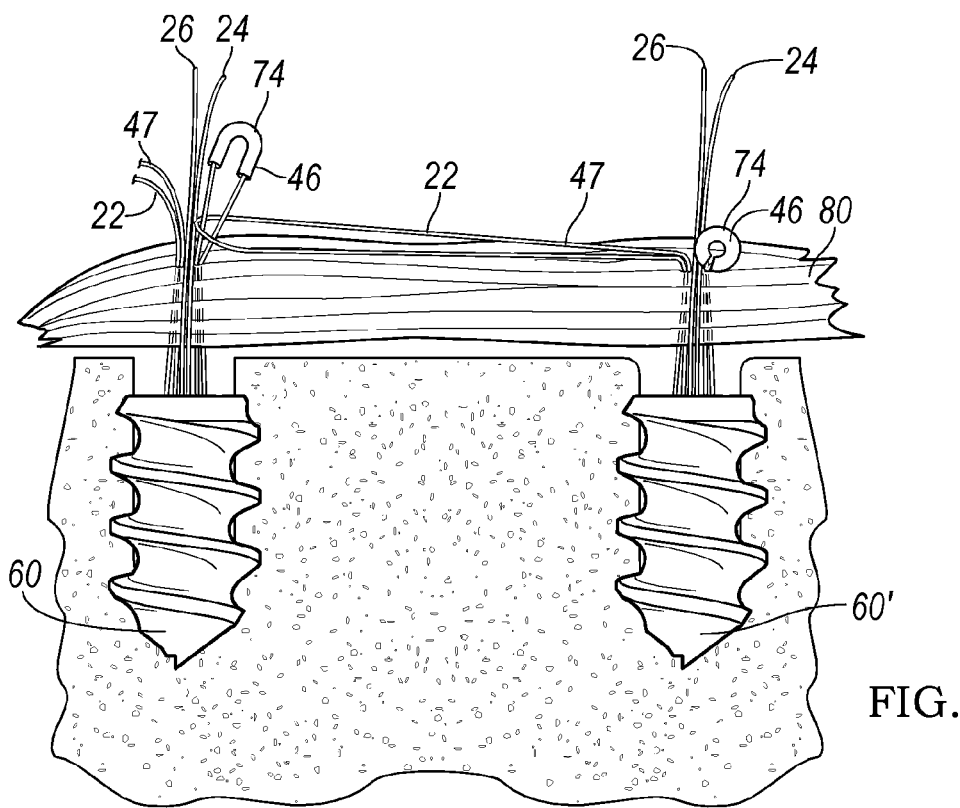
FIGS. 19A-19C represent the coupling of soft tissue to a bone using yet alternate teachings.
Figure 19B:
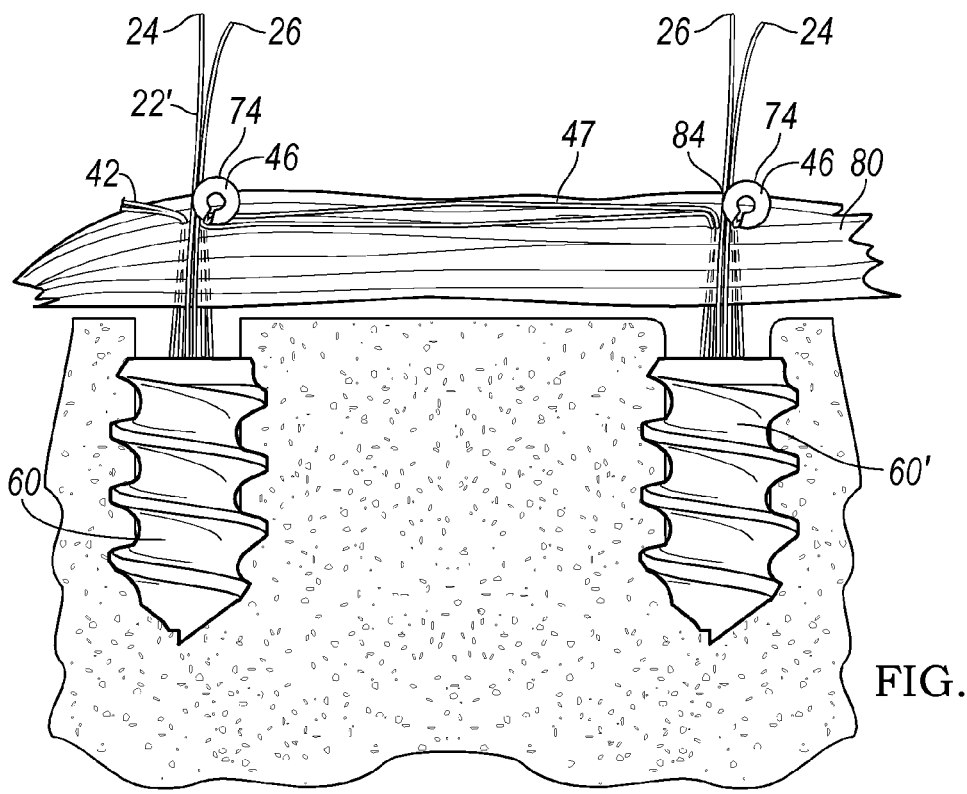
Figure 19C:
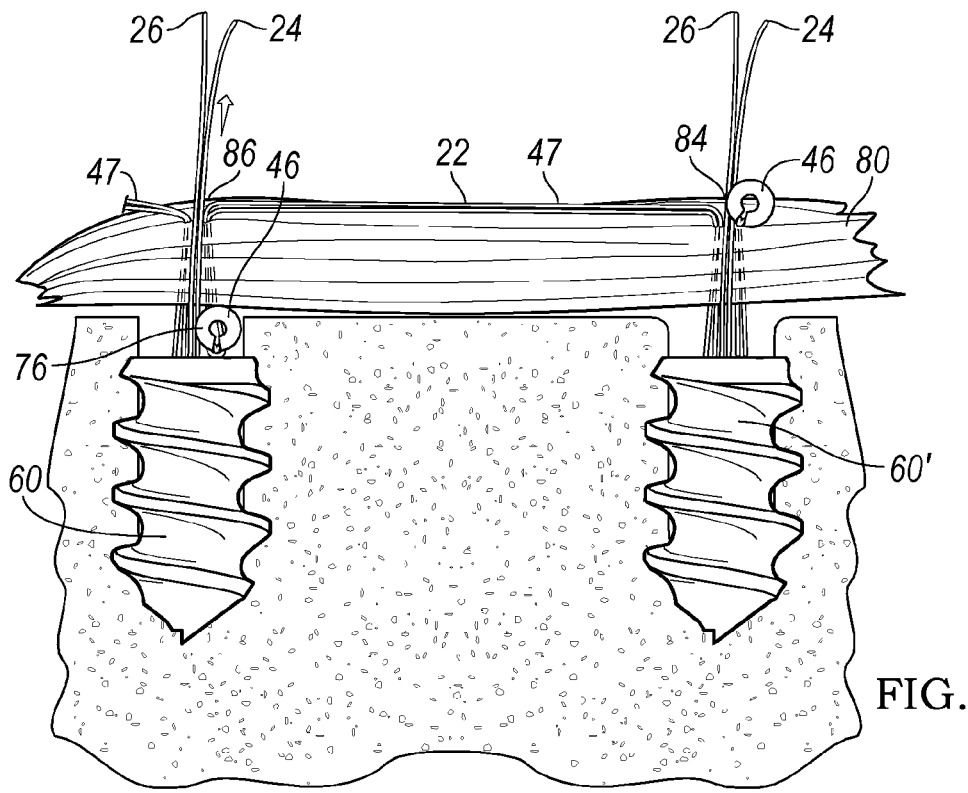

As can be seen in FIGS. 19A-19C, several fixation members 60 and 60' can be coupled to the suture construction 22 to fasten soft tissue 80 to bone. As seen in FIG. 19A, the collapsible tube 74 can be coupled to a first loop 46 while the second loop 47 can be used to couple the first suture 22 to the second fastener 60'. In this regard, they are coupled using a collapsible tube 76 of the second suture 22', thus allowing downward force along the entire length between the fasteners, thus providing bridge fixation as well as point fixation.

As seen in FIG. 19B, tension of the ends 24 and 26 of the first suture 22 draws the second loop 47 into the fixation member 60'. The second loop 47 of the first suture 22 is then coupled to the collapsed tube 76. This couples the first and second fasteners together and applies the downward force.

As seen in FIG. 19C, the second loop 47 of the first suture 22 can be passed through a second aperture 86 in the soft tissue 80. A second loop 47 is then coupled to the collapsible tube 76 associated with the second suture 22'. The collapsed tube 76 of the second suture 22' functions to fix the suture 22' to the fixation member 60'. It is envisioned the collapsed tube 76 can be found within a bore defined in the bone or the fastener 60.

Figure 20A:
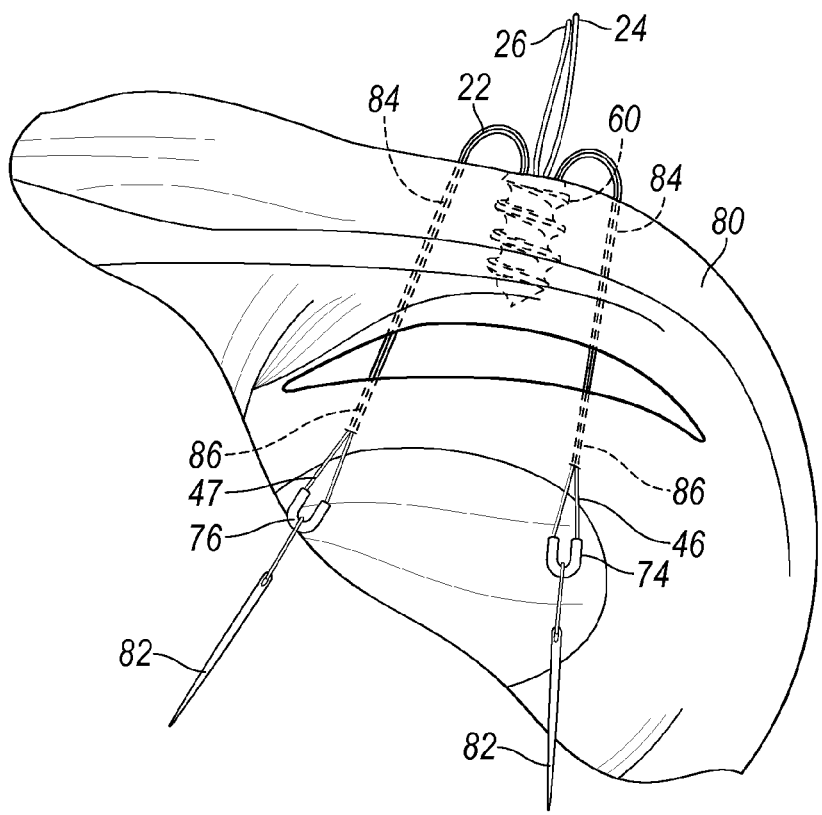
FIGS. 20A and 20B represent a meniscal repair according to the present teachings.
Figure 20B:
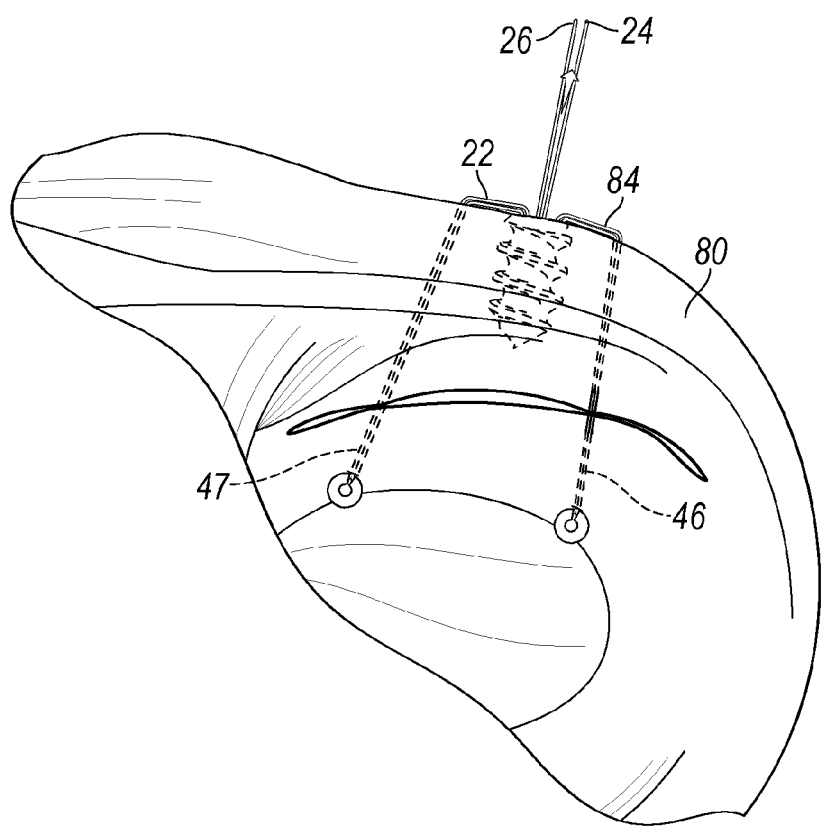

FIGS. 20A and 20B represent the use of a suture construction 22 to repair a meniscus. Fasteners 82 are coupled to first and second loops 46 and 47. After the fixation member 60 is coupled to bone or soft tissue, the first loop 46 is passed through a first aperture 84 in a first portion of the meniscus. The first loop and collapsible tube 74 is then passed through a second aperture 86 and a second portion of the meniscus. The second loop 47 and second collapsible tube 76 are similarly passed through the meniscus. Tension is applied to the first and second ends 24 and 26 of the suture 22 to pull the meniscus together. As seen in FIG. 20B, a first and second collapsible tube 74 and 76 are constricted so as to couple the suture to the meniscus.

Figure 21:
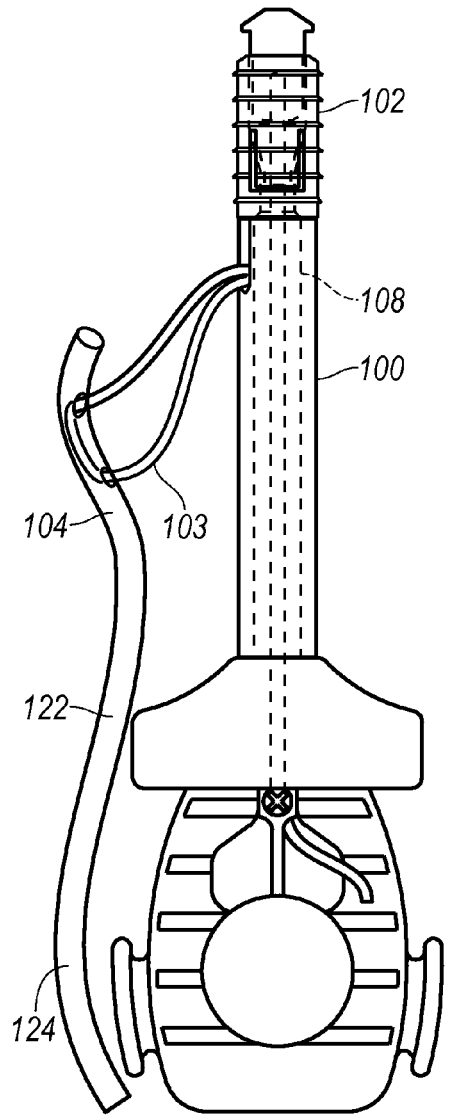
FIG. 21 represents an insertion tool with associated fastener and soft tissue anchor.

FIG. 21 represents a tool 100 with associated fastener 102 and soft tissue anchor 104. The tool 100 has a handle portion 106 which releasably engages the fastener 102. Associated with the handle portion 106 is a hollow longitudinal suture 103 which accepts a soft tissue anchor 104. Disposed at a distal end 110 of the hollow longitudinal portion 108 is a slot having a portion of the soft tissue anchor 104 disposed therethrough. The distal end 110 is further configured to support the fastener 102 for insertion into a bore defined within bone 112.

Figure 22:
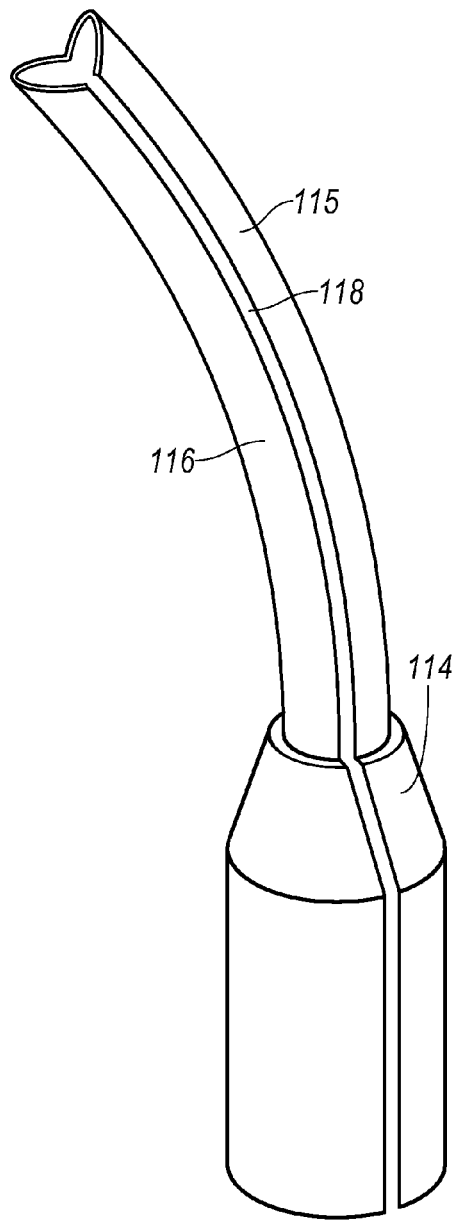
FIG. 22 represents an insertion sleeve associated with the tool shown in FIG. 21.

FIG. 22 represents an insertion guide 115 having a handle portion 114 and a curved longitudinal guide tube 116. The longitudinal guide tube 116 and handle portion 114 slidably accept the fastener 102 and soft tissue anchor 104. The curved longitudinal tube 116 and handle portion 112 define a slot 118 which also slidably accepts the suture 103 of soft tissue anchor 104.

Figure 23:
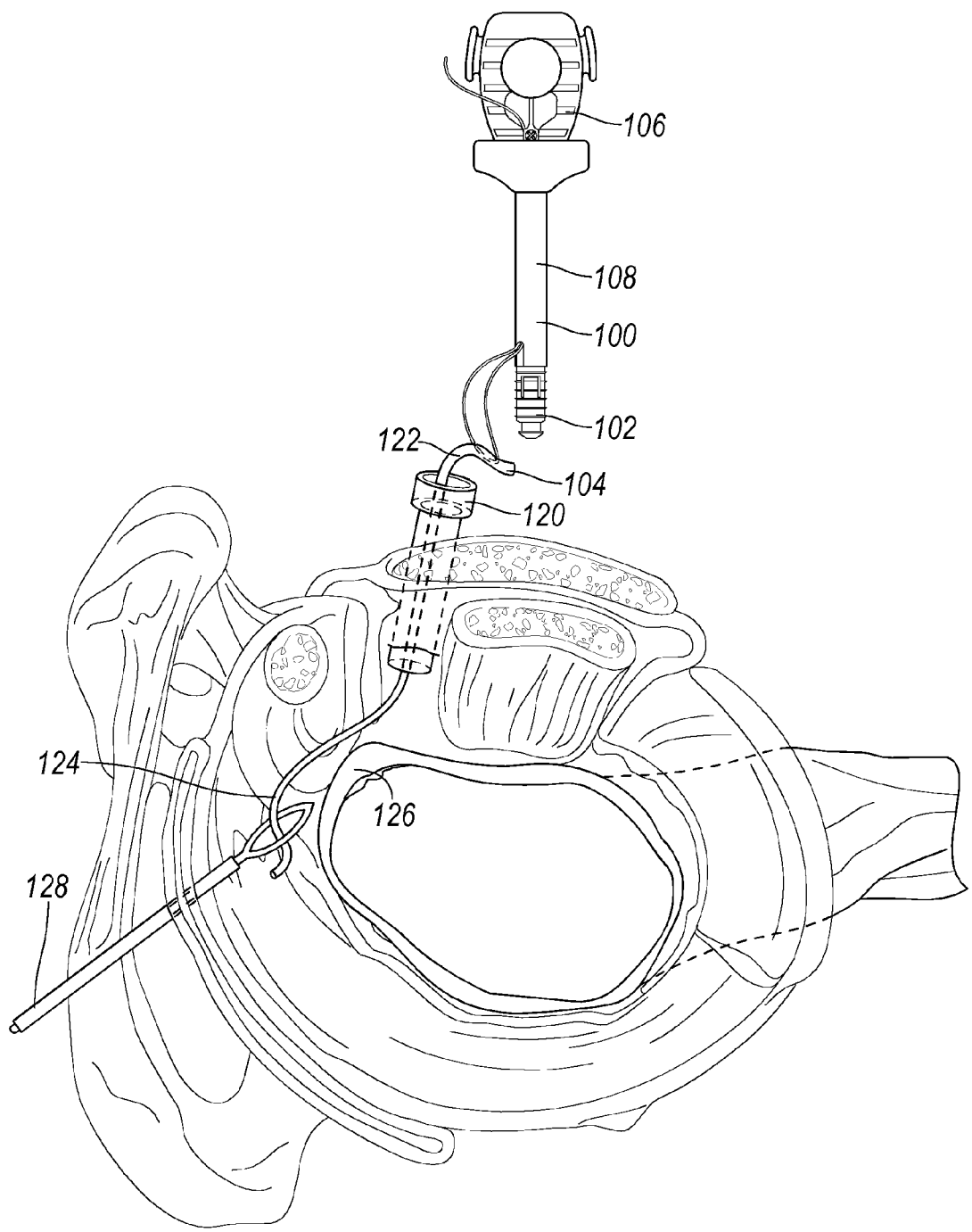
FIGS. 23-31 represent the repair of a rotator cuff using a tool shown in FIG. 21.

FIGS. 23-38 generally depict the repair of labral tissue of a glenoid. While the repair shown generally relates to a specific anatomical injury, it is envisioned the teachings herein can be applied to other anatomical regions which require the coupling of soft tissue to bone. For example, a meniscal repair in a knee may be performed using similar techniques. As shown in FIG. 23, access to the region of the injury is made through a tube 120. At this point, a collapsible tube 122 having an extended portion 124 is threaded through tube 120 into close proximity of the soft tissue 126 to be coupled to bone. A suture grabber 128 such as a speed pass by Biomet Sports Medicine is used to pierce the soft tissue 126 and to grab the extended portion 124 of the collapsible tube 122. This extended portion 124 is then pulled through the soft tissue 126.

Figure 24:
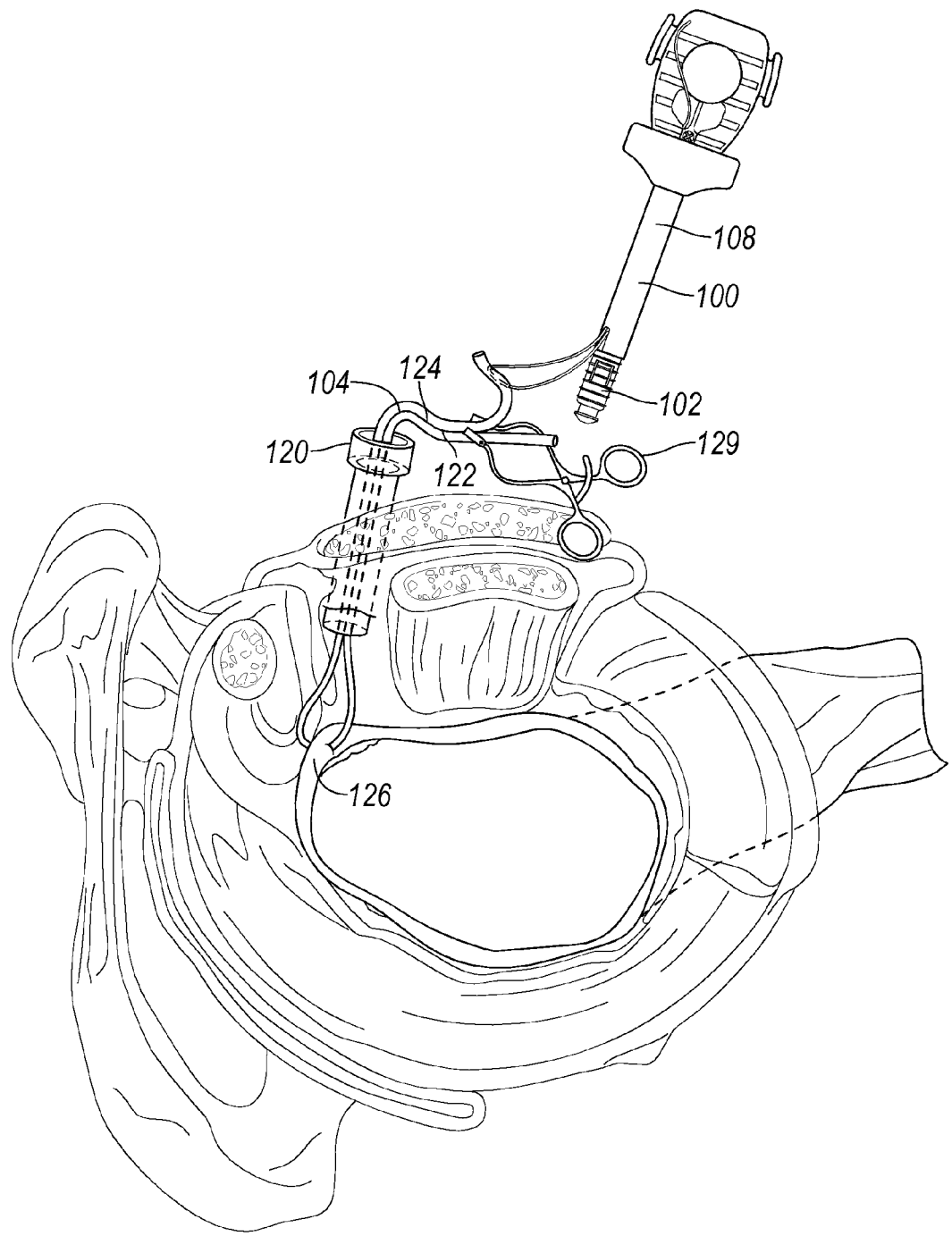
Figure 25:
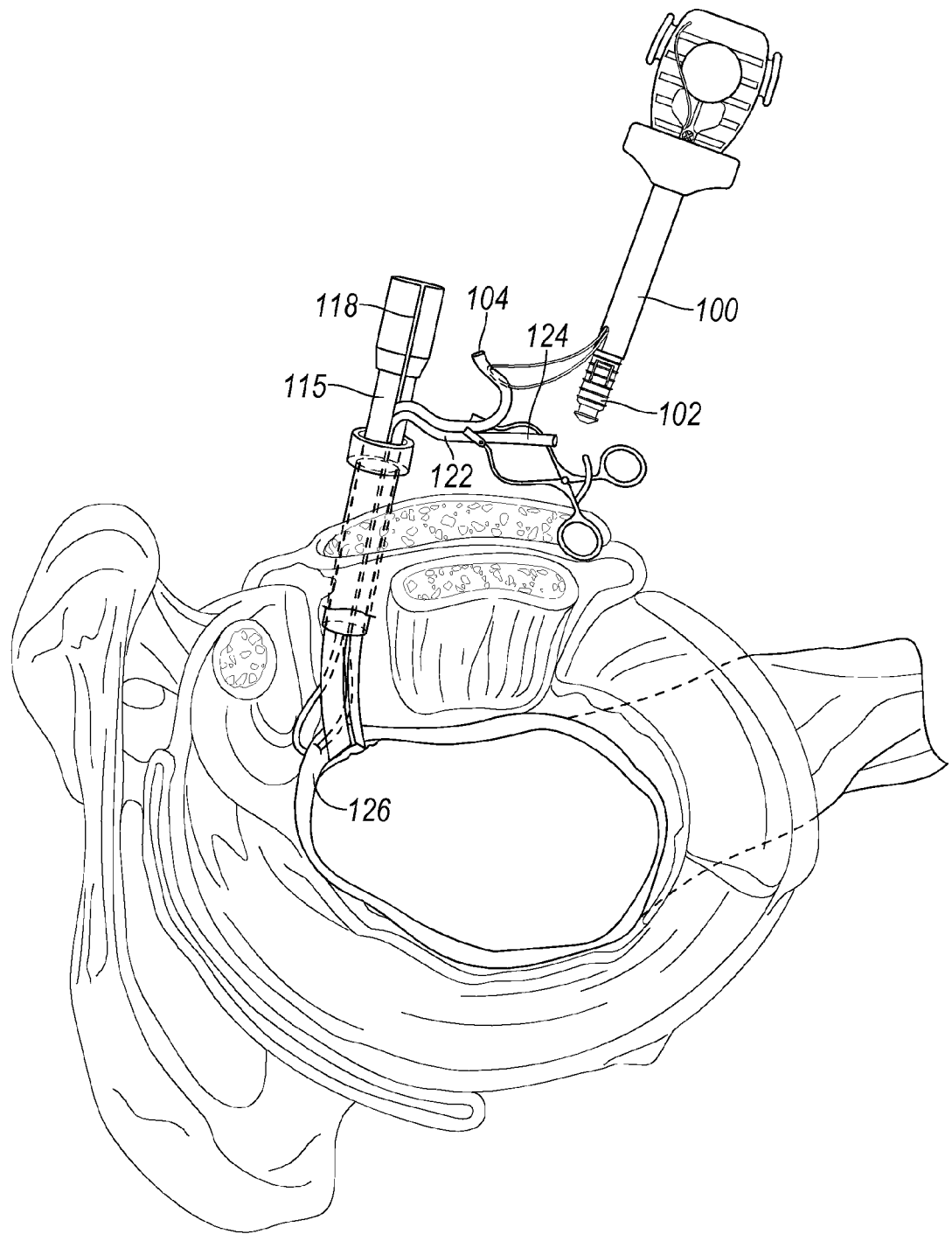

As shown in FIG. 24, the extended portion 124 of the collapsible tube 122 is fed back out the access tube 120 and clamped with clamp 129 so as to prevent inadvertent translation with respect to the tube. As shown in FIG. 25, the insertion sleeve 115 is placed through the access tube 120. The collapsible tube 122 is placed through the slot 118 defined in the handle portion 114 and longitudinal guide tube 116.

Figure 26:
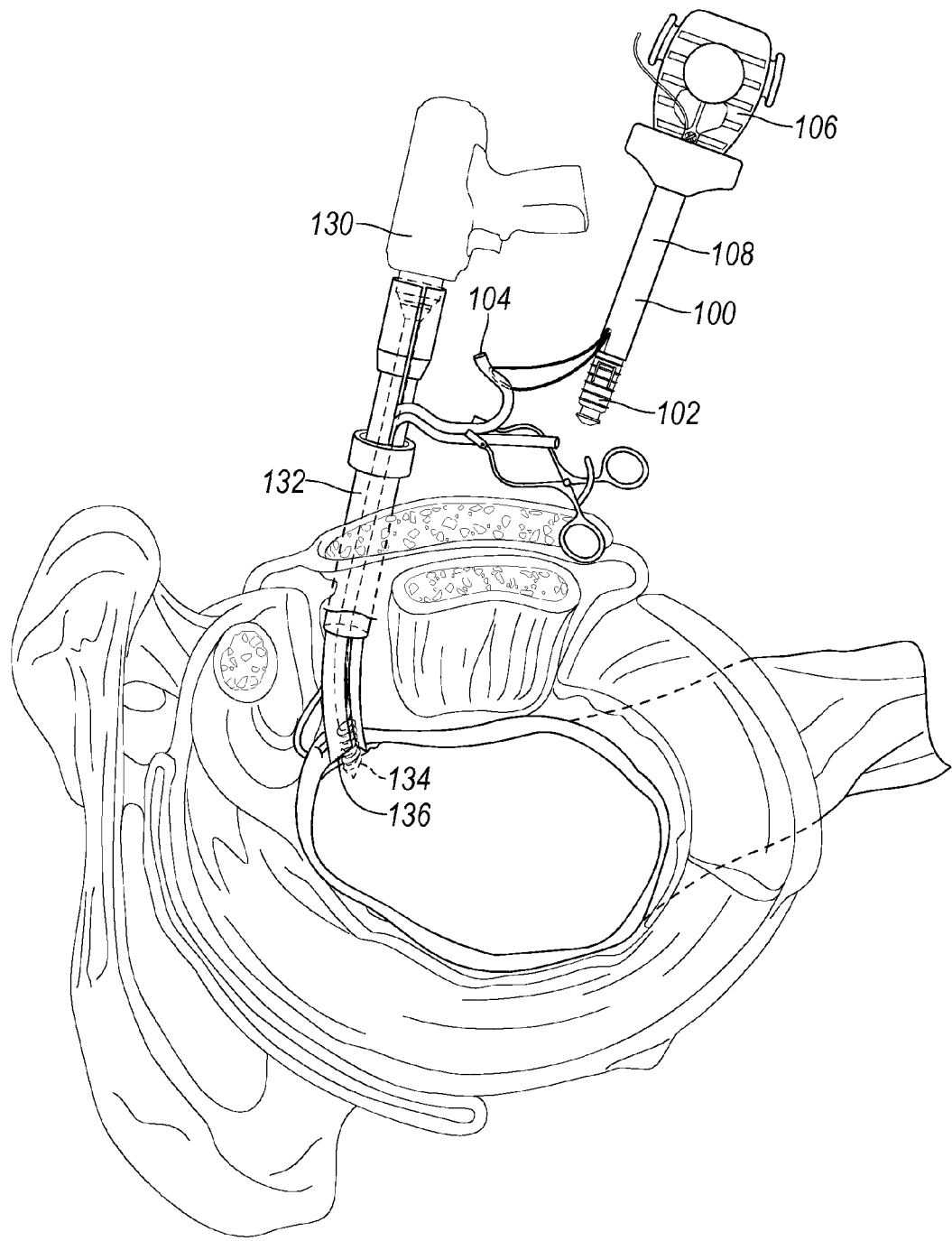
Figure 27:
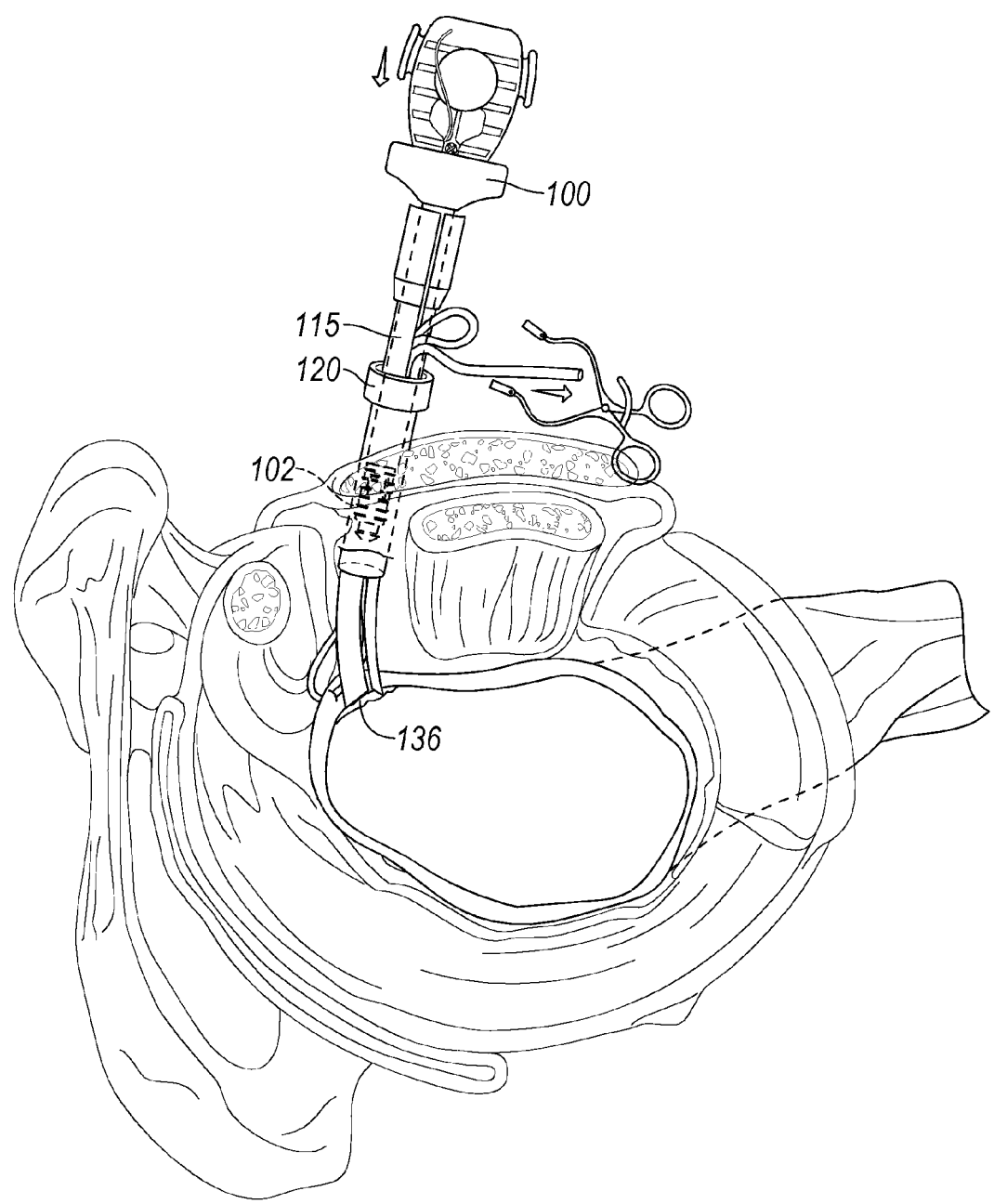

FIG. 26 shows a drill 130 having a flexible drive shaft 132 and a bone cutting drill bit 134. The drill bit 134 is placed through the guide tube 116 to form a bore 136 in bone at a location adjacent to a soft tissue repair. It is envisioned the bore 136 can be placed under or adjacent the soft tissue repair.

Figure 28:
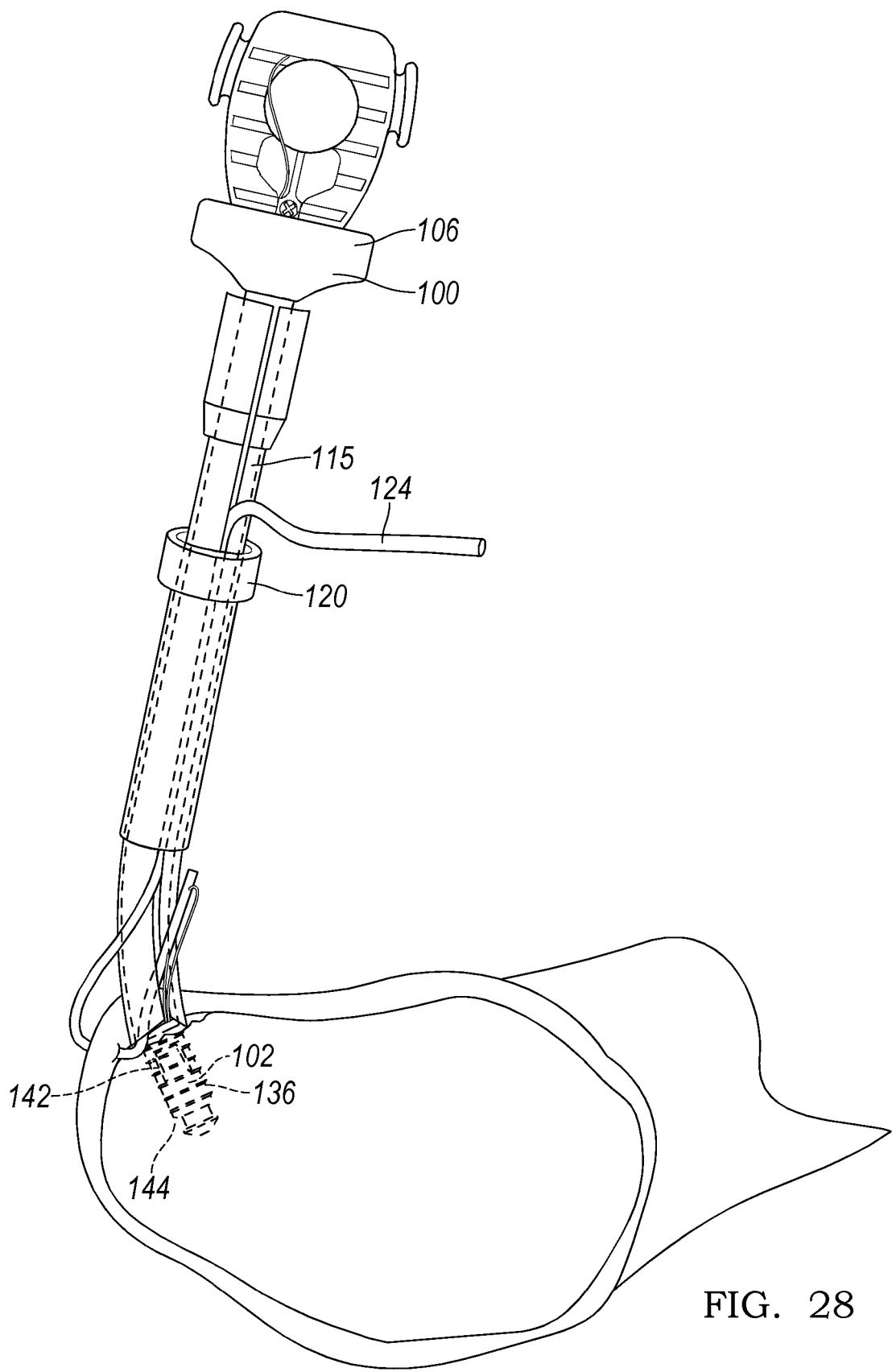
Figure 29:
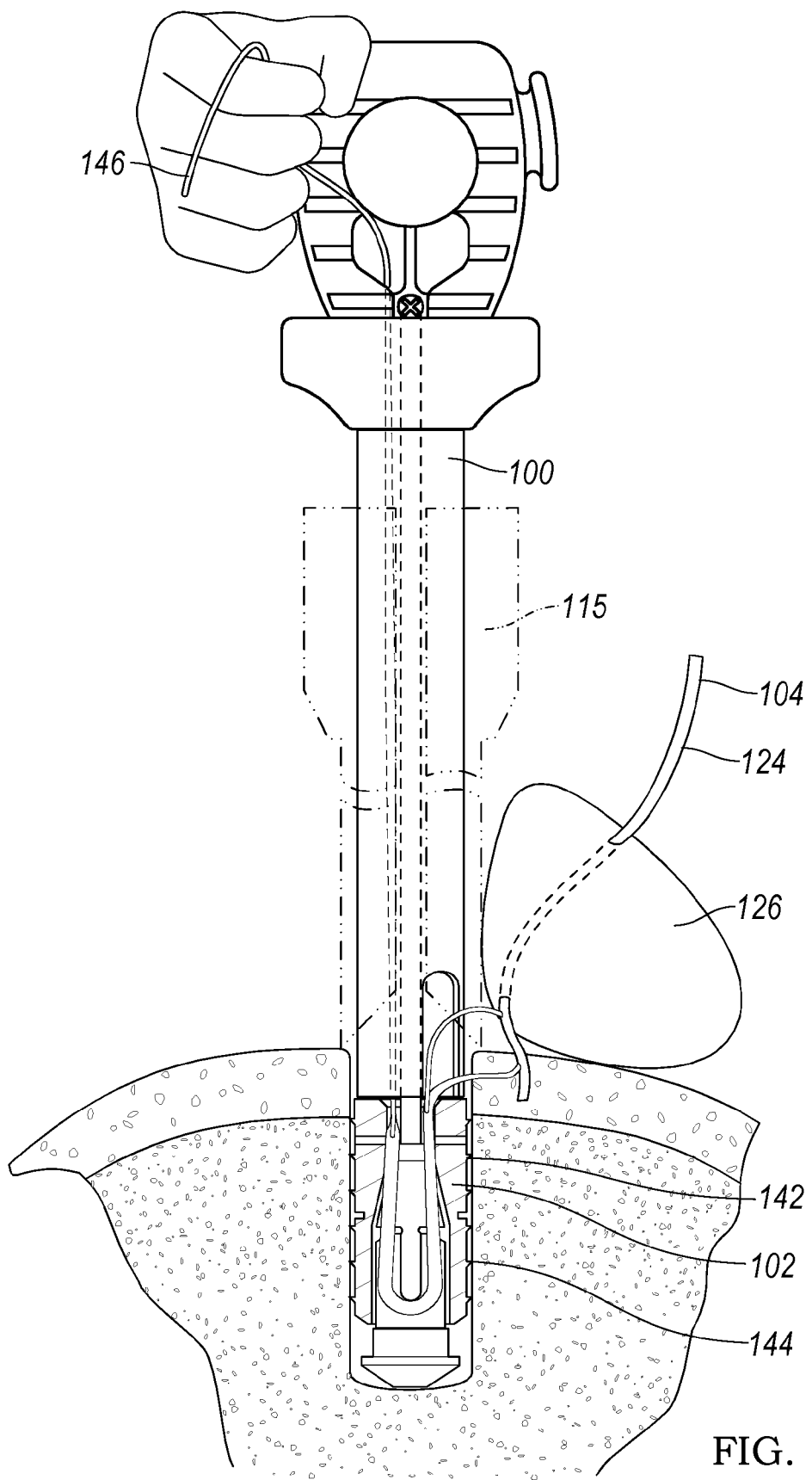

After the bore 136 has been formed in the bone, the tool 100, fastener 102, and associated soft tissue anchor 104 are placed through the insertion guide 115. As shown in FIG. 28, the fastener is inserted into the bore 136. It is envisioned the fastener 102 can be a two-part fastener having a first insertion portion 140 and a locking portion 142. The locking portion 142 can have a plurality of expandable bone engaging members 144.

Figure 30:
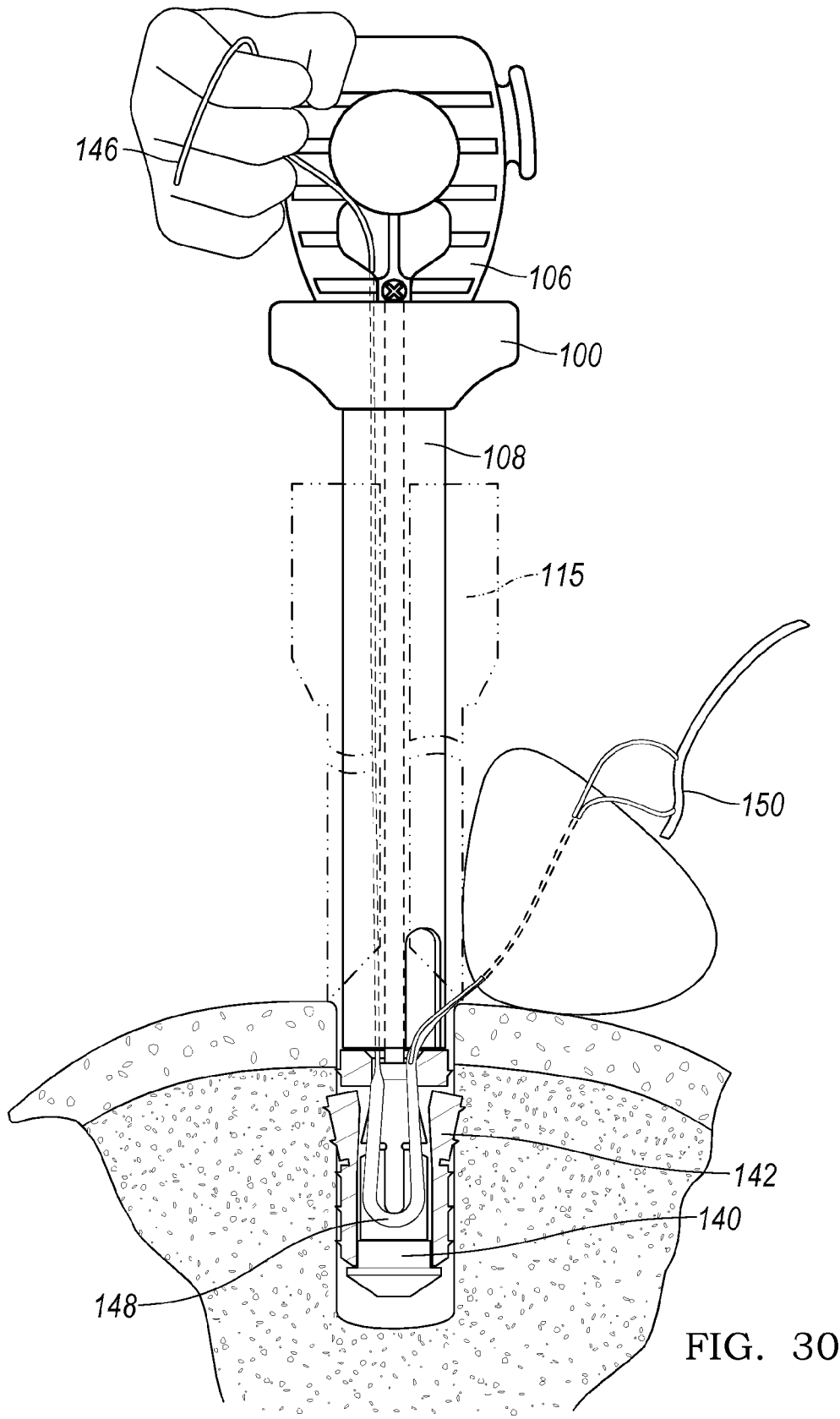

As seen in FIG. 30, the pair of sutures 146 can be pulled through the soft tissue 126. The sutures 146 can be coupled together using a suture construction shown in FIGS. 1A or 1B. In this regard, the suture 146 can be looped through an integrally formed collapsible member or tube 148 which can be used to fix the suture construction with respect to either the insert or locking portion 140, 142 of the fastener.

Figure 31:
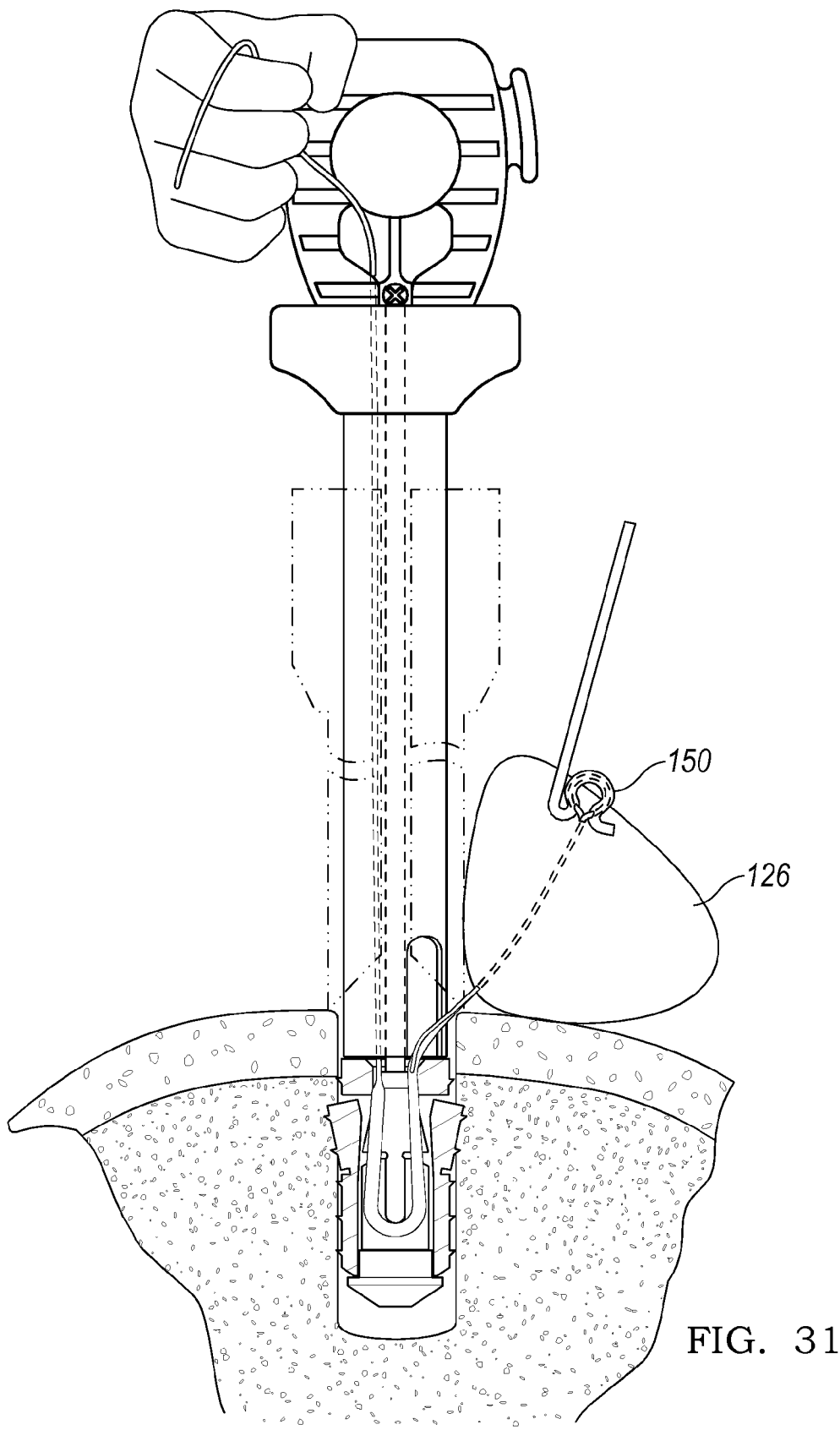
Figure 32:
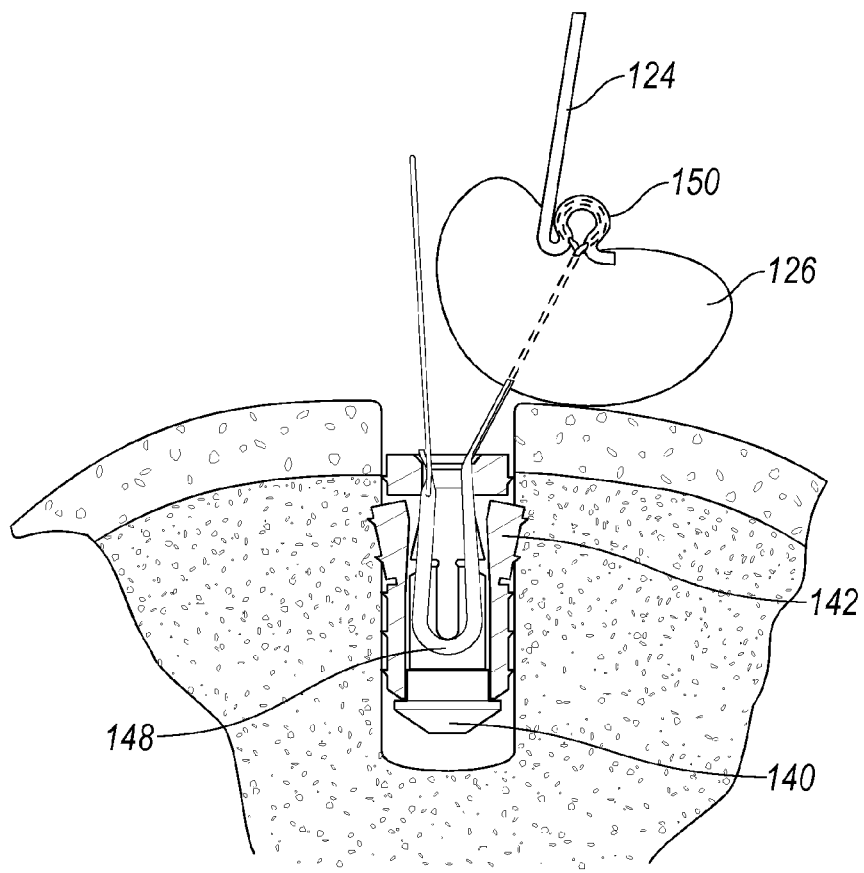
FIGS. 32-38 represent alternate methods for tying a suture anchor to the fastener.
Figure 33A:
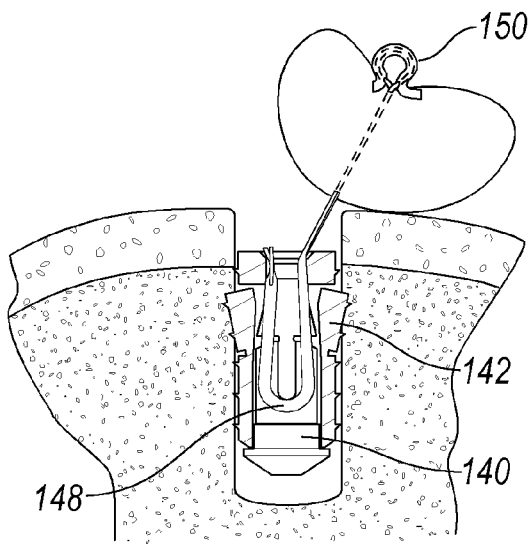
Figure 33B:
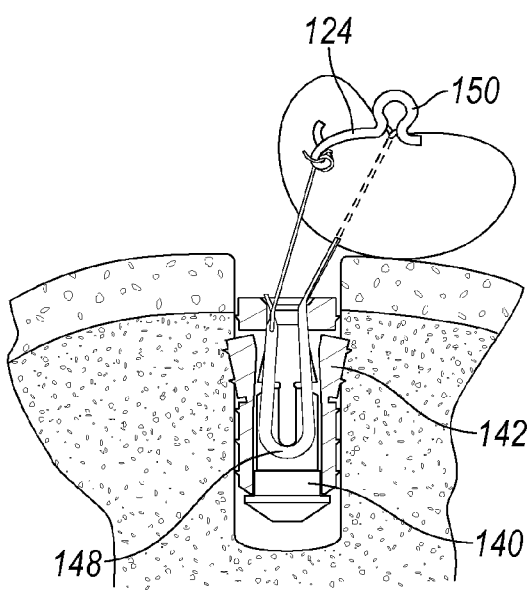

As shown in FIG. 31, when tension is applied to the suture 146 through the tool 100, a collapsible portion 150 of the collapsible tube engages the soft tissue 126. As seen in FIGS. 32-33B, once the collapsible portion 150 of the collapsible tube is set, the tool 100 can be removed from the insertion guide 115. At this point, the end of the longitudinal tube can be removed, or can be tied to the suture 146.

Figure 34:
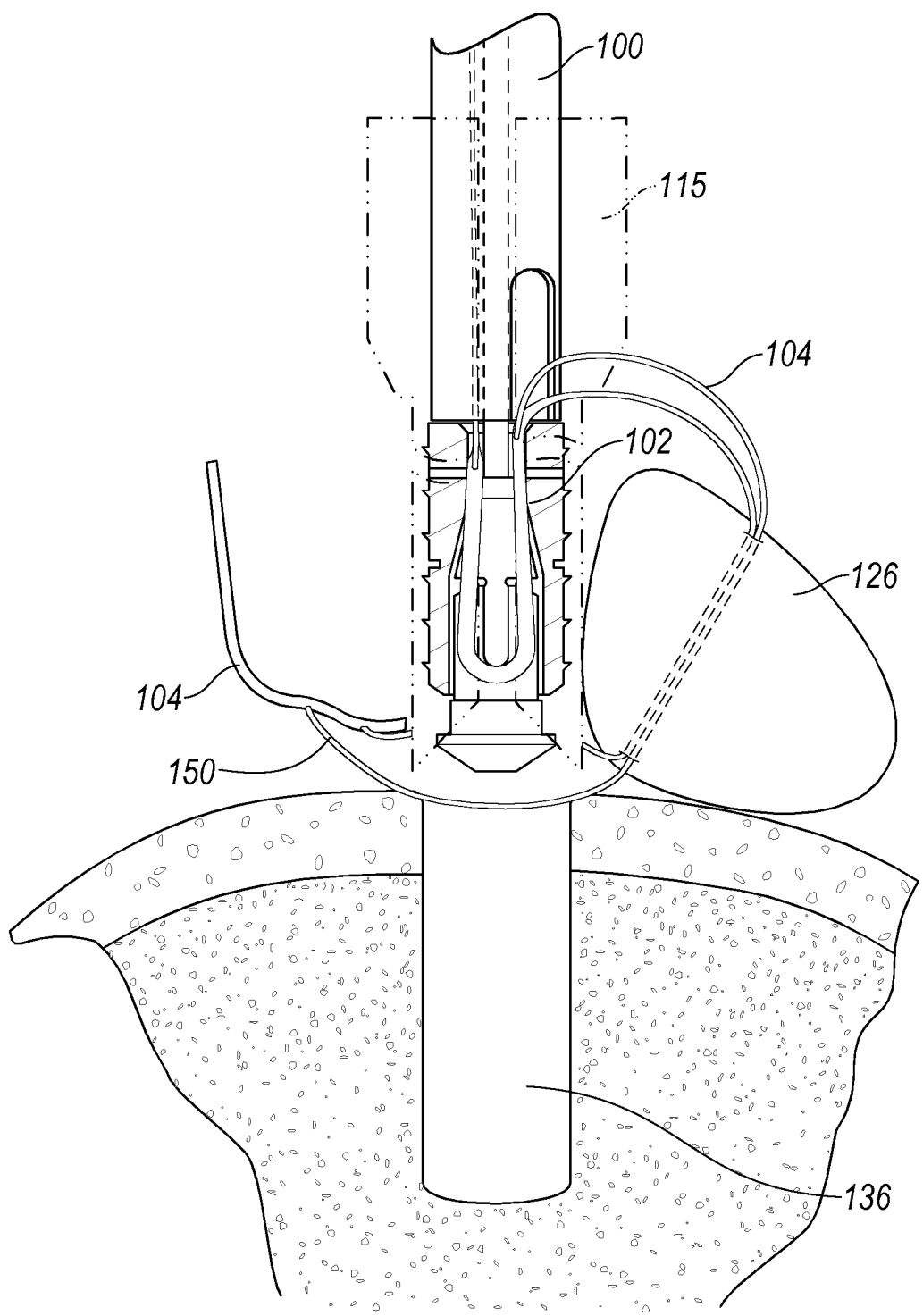
Figure 35:
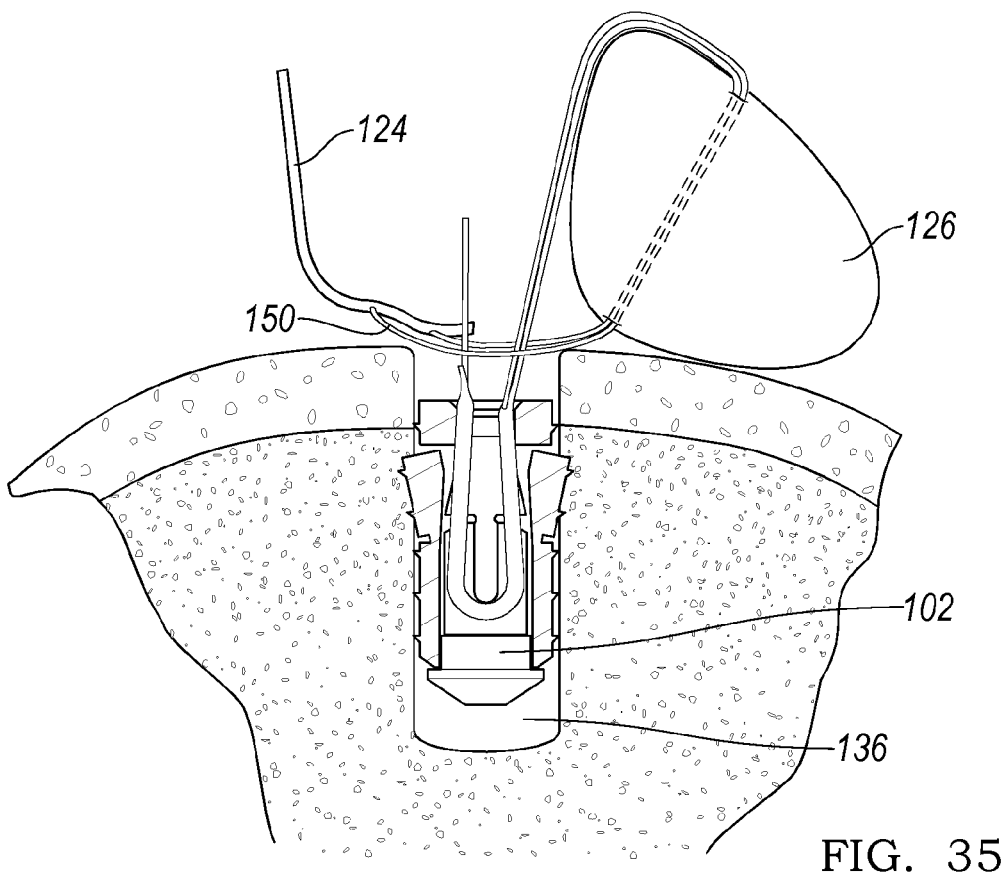
Figure 36:
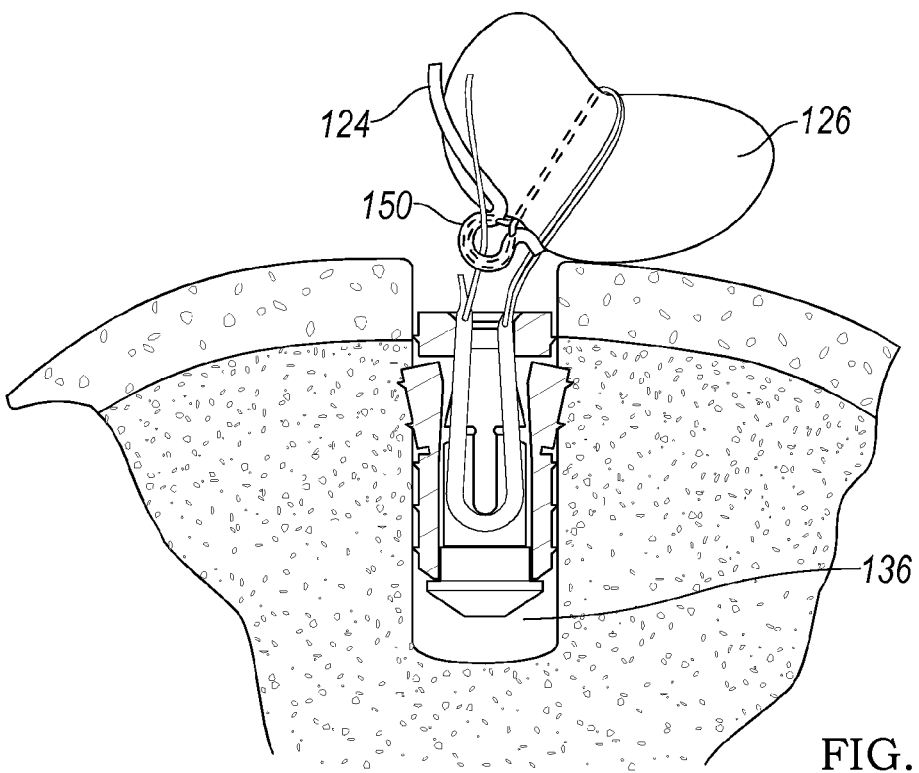

FIGS. 34-36 represent an alternate method for coupling a suture construction 104 to the fastener 102. Shown is a fastener 102 being passed through the loop of the suture. In this regard, the fastener 102 is passed through the loop of the suture prior to insertion of the fastener 102 within the bore 136 in the bone. After removal of the tool 100, tension is applied to the ends of the suture to constrict the collapsible portion 150 of the collapsible tube. This tensioning pulls the soft tissue 146 into a position with respect to the fastener 102.

Figure 37:
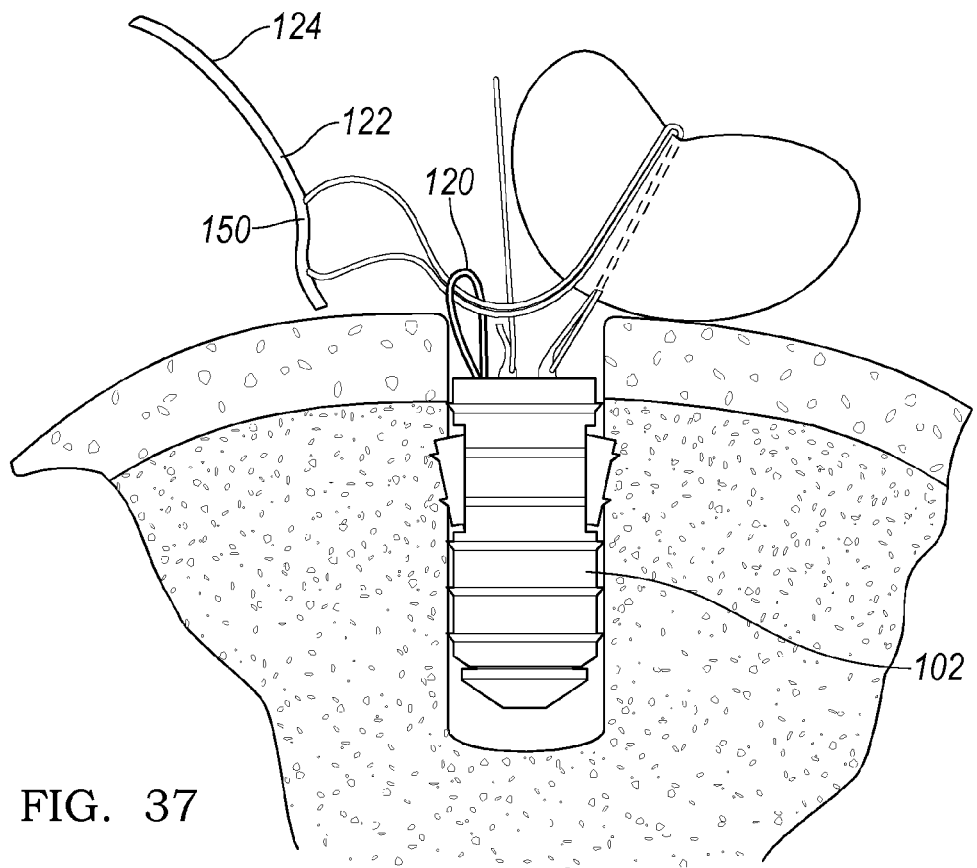
Figure 38:
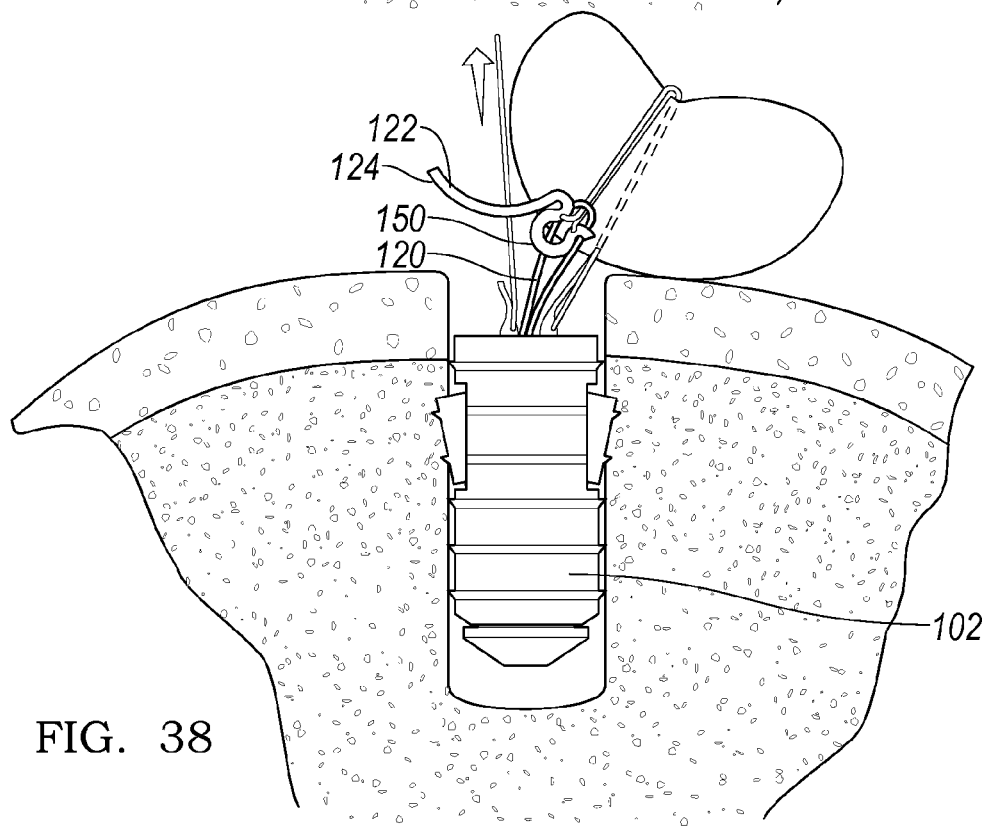

As shown in FIGS. 37 and 38, the fastener 102 can have an associated integral loop 120. The integral loop 120 can be a suture or can be an integral polymer construction. The compressible tube 122 can be threaded through the integral loop 120. Application of tension onto the suture causes the collapsible portion 150 of the collapsible tube to bear against the integral loop 120 and the soft tissue. It is envisioned the integral loop can be elastically deformable or can be fixed with respect to the fastener.

Figure 39:
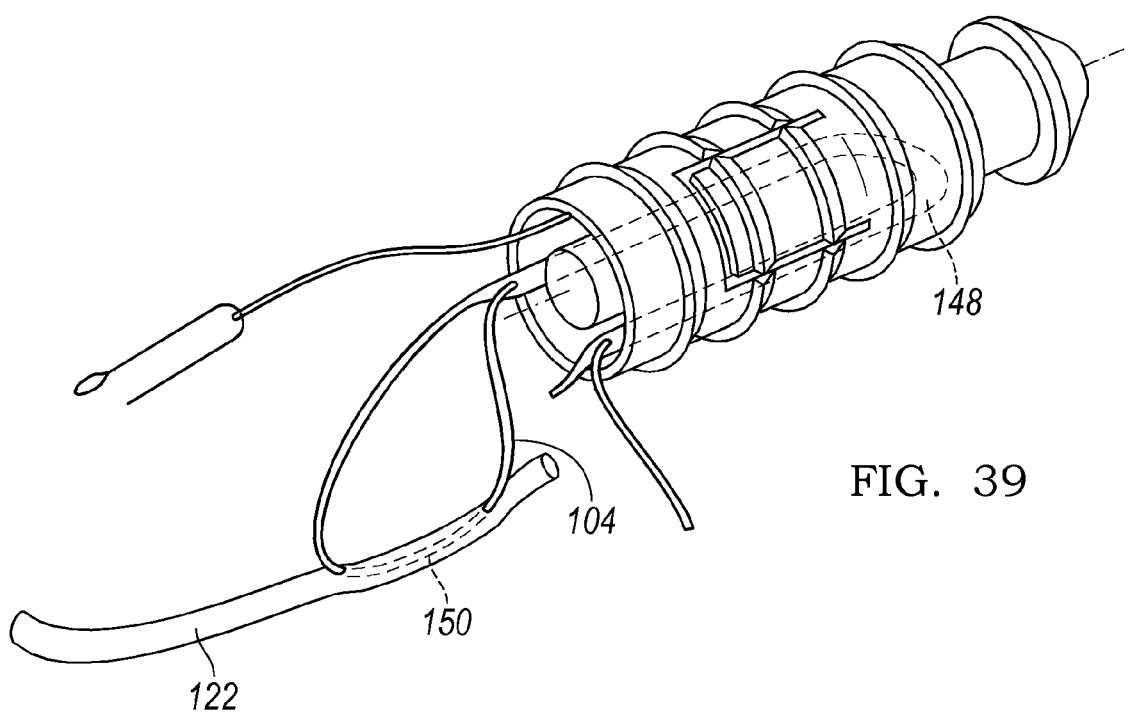
FIG. 39 represents the suture anchor coupled to a two-piece fastener.

FIG. 39 represents a suture construction coupled to a two-piece fastener 102. The suture construction 104 can be threaded through the aperture formed within the first or second portions of the fastener 102. As shown, an integrally formed collapsible tube portion 148 can be disclosed within the aperture of the fastener. Upon application of tension onto the suture, the tension will cause the collapse of this second collapsible tube portion 148, thus locking the suture to the fastener body 102.

FIGS. 40-44 represent an alternative system and method of coupling soft tissue to bone. By way of non-limiting example, a fastener 102 can be coupled to the bone as described above and shown in FIGS. 23-30. Subsequent to this, the collapsible portion 150 of the tube 104 can be passed through the soft tissue 126.

Figure 40:
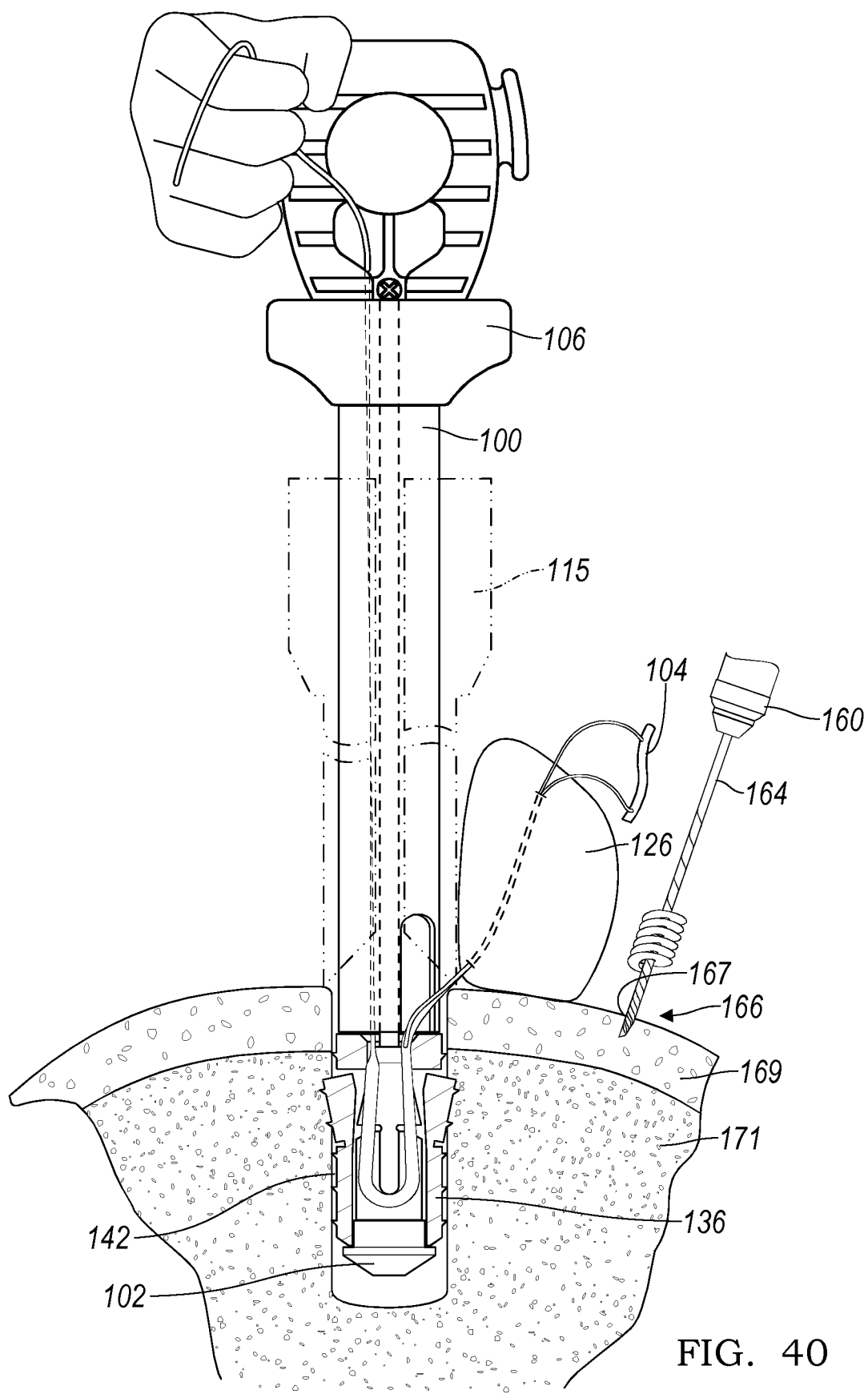
FIGS. 40-44 represent an alternate system and method of coupling soft tissue to the bone.
Figure 41:
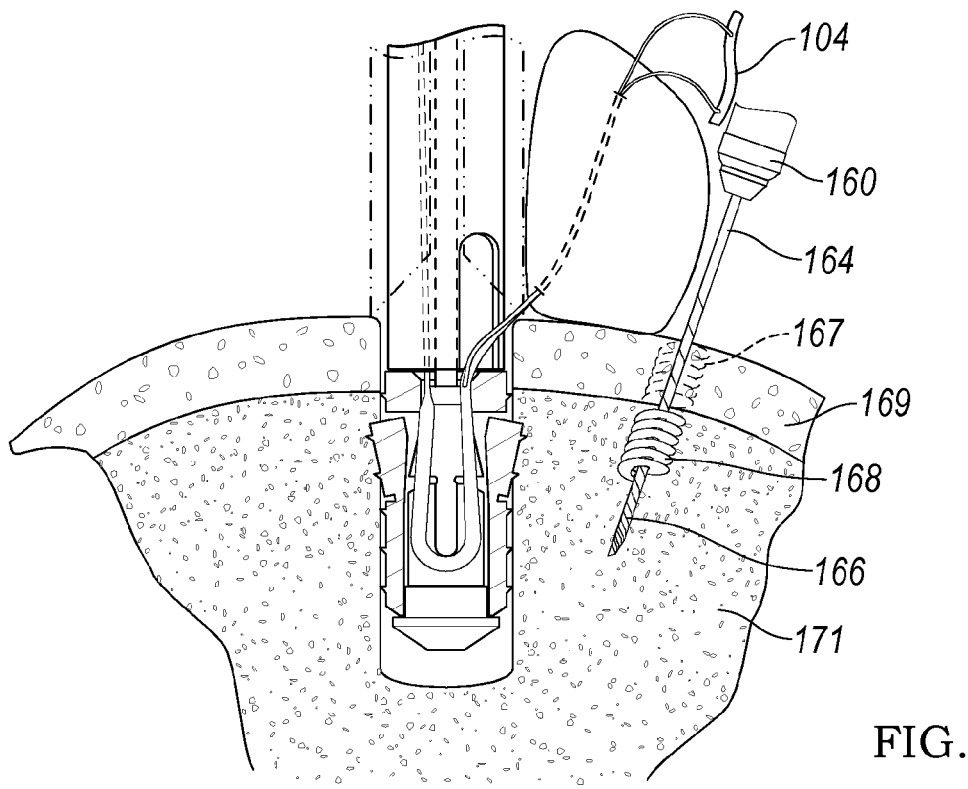
Figure 42:
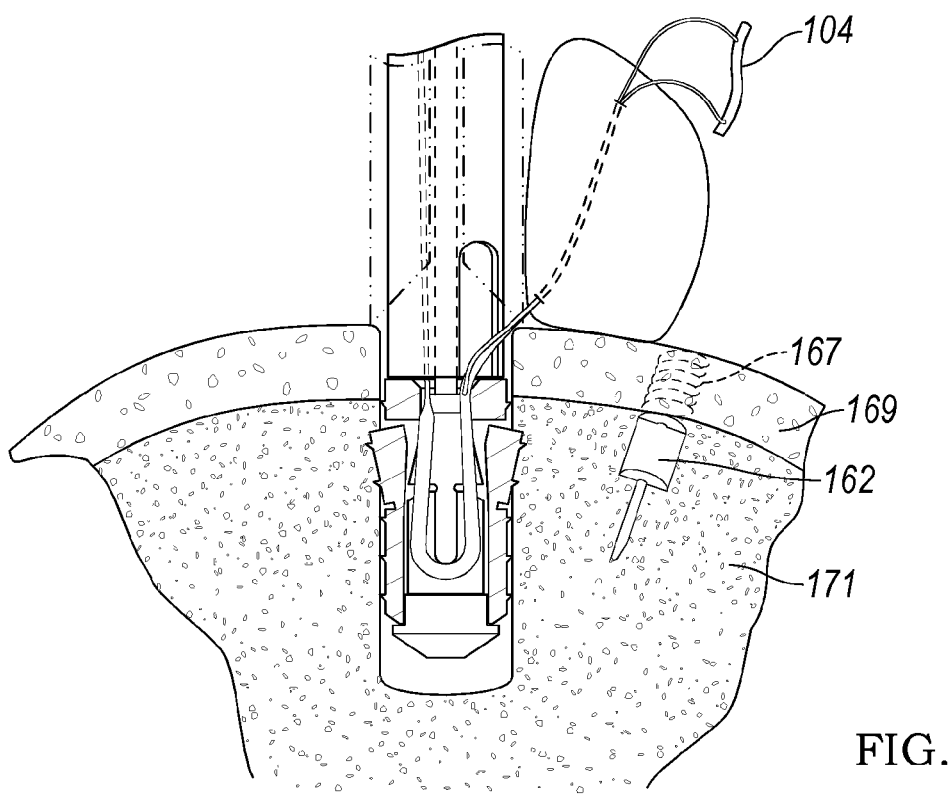

As best seen in FIGS. 40-42, a drive tool 160 is used to form a soft tissue engagement site 162 in a bone structure. The tool 160 has a drive (not shown) which rotates a bone cutting bit 164. The bone cutting bit 164 has a first portion 166 configured to drill a hole 167 through cortical bone and a threaded second portion 168. The threaded second portion 168 is configured to cut threads in the cortical 169 and cancellous 171 structures. This is accomplished by advancing the cutting bit 164 into the bone at a predetermined rate while rotating the bit at a predetermined speed. As shown in FIG. 41, after the second portion 168 has entered the cancellous bone 171, the bit is rotated while keeping the rotating tool 160 in a substantially stationary position. The thread cutting threads of the second portion 168 then displace cancellous bone 171, forming the cavity 162. The bit is removed by rotating the thread cutting threads through the threads formed in the cortical bone 169.

Figure 43:
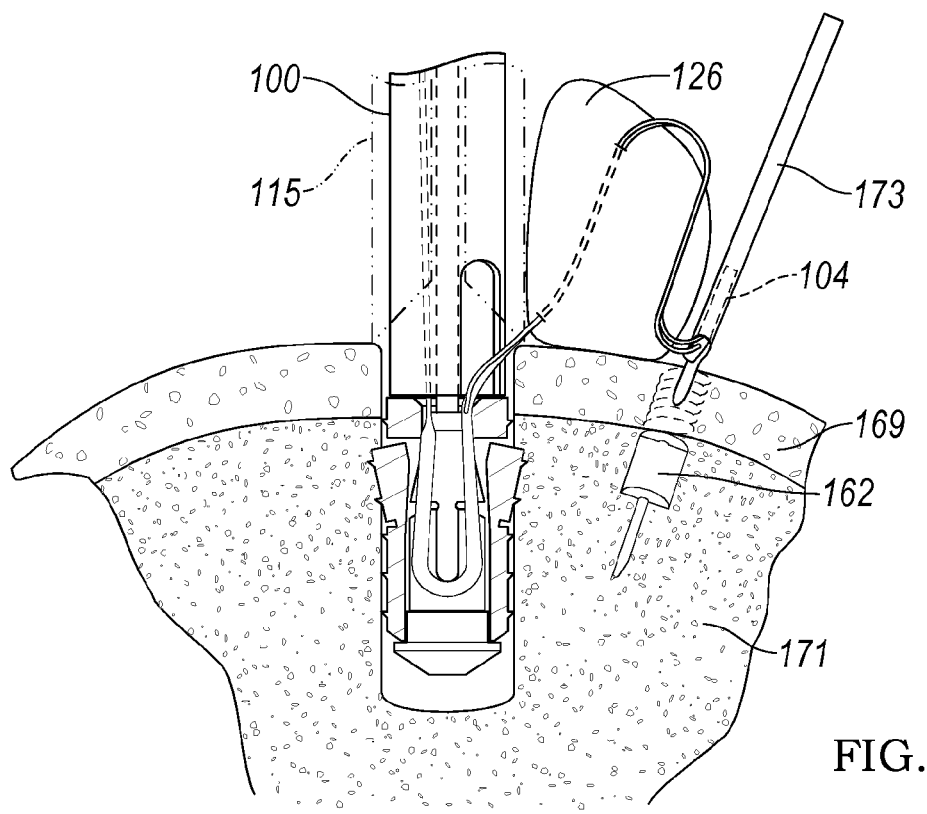
Figure 44:
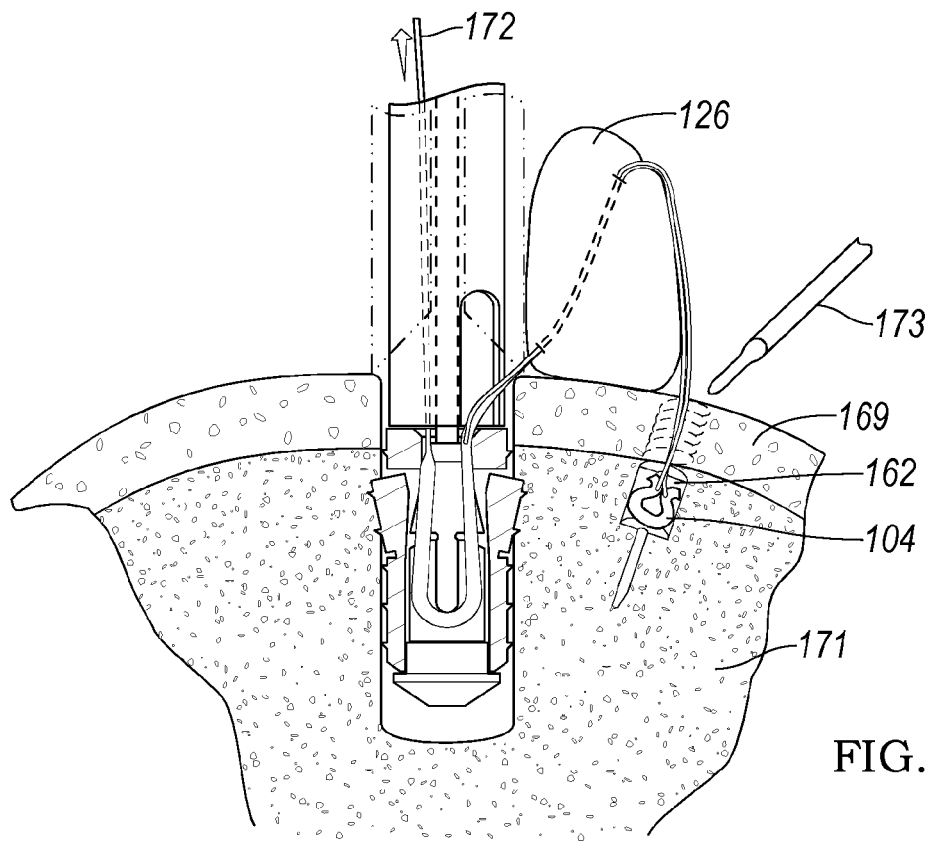

As shown in FIG. 43, the collapsible tube 104 of suture anchor is passed through passage 167 and into the cavity 162. In this regard, an insertion tool 173 can be used to insert the collapsible tube 104 into the cavity 162. As shown in FIG. 44, tension is applied to the end 172 of the suture anchor, thus causing the collapsible portion 104 of the anchor.

The description of the invention is merely exemplary in nature and, thus, variations that do not depart from the gist of the invention are intended to be within the scope of the invention. For example, any of the above mentioned surgical procedures is applicable to repair of other body portions. For example, the procedures can be equally applied to the repair of wrists, elbows, ankles, and meniscal repair. The suture loops can be passed through bores formed in soft or hard tissue. It is equally envisioned that the loops can be passed through or formed around an aperture or apertures formed in prosthetic devices e.g. humeral, femoral or tibial stems. Further, the suture material and collapsible tubes can be formed of resorbable material. Such variations are not to be regarded as a departure from the spirit and scope of the invention.

What is claimed is:

1. A method for coupling soft tissue to bone comprising:
   forming a bore in the bone;
   positioning an anchor in the bone, the anchor having a self-locking suture construct extending therefrom, the construct having a first loop, a second loop, and a pair of ends, wherein the suture construct is formed of a body that defines a longitudinal extending passage therein, the first end extending into and out of a first passage portion to form the first loop and the second and extending into and out of a second passage portion to form the second loop;
   positioning the first loop relative to the soft tissue;
   positioning the second loop relative to the soft tissue;
   coupling the first loop to the second loop about the soft tissue; and
   pulling the pair of ends to tighten the suture construct to fix the soft tissue to the bone.

2. The method of claim 1, wherein positioning the first loop further includes passing the first loop through the soft tissue.

3. The method of claim 2, wherein positioning the second loop further includes positioning the second loop around the soft tissue to couple the first loop to the second loop about the soft tissue.

4. The method of claim 1, wherein coupling a first loop to the second loop includes coupling the first loop to the second loop with a fastening element.

5. The method of claim 4, wherein the fastening element is a suture and the suture couples a first loop to the second loop.

6. The method of claim 5, wherein the suture includes a knot wherein the knotted suture fastener couples the first loop to the second loop.

7. The method of claim 1, wherein the pair of ends extend from the bore in the bone and pulling the pair of ends includes pulling the pair of ends from the bore in the bone.

8. The method of claim 1, wherein positioning the anchor includes positioning a stiff anchor in the bore.

9. The method of claim 1, wherein coupling the first loop and the second loop further includes coupling ends of the first and second loops to the soft tissue opposite the first and second passage portions.

10. The method of claim 9, wherein pulling the pair of ends positions the first and second passage portions adjacent to the anchor upon tightening the suture construct to fix the soft tissue to the bone.

11. A method for coupling soft tissue to bone comprising:
forming a hole in the bone;
positioning an anchor in the hole, the anchor having a self-locking suture construct extending therefrom, the construct having a first loop, a second loop, a first end, and a second end, wherein the suture construct is formed of a body that defines a longitudinal extending passage therein, the first end extending into and out of a first passage portion to form the first loop and the second end extending into and out of a second passage portion to form the second loop;
positioning the first loop relative to the soft tissue;
positioning the second loop relative to the soft tissue;
coupling the first loop to the second loop about the soft tissue with a fastening element; and
tensioning the first end and the second end to tighten the suture construct to secure the soft tissue to the bone.

12. The method of claim 11, wherein coupling the first loop to the second loop with the fastening element further includes coupling the first loop to the second loop with a suture fastening element.

13. The method of claim 11, wherein positioning the first loop and positioning the second loop further includes passing the first loop through the soft tissue and positioning the second loop around the soft tissue and coupling the first and second loops with the fastening element.

14. The method of claim 11, wherein positioning the first loop and the second loop includes positioning ends of the first loop and the second loop relative to the soft tissue and the first and second passage portions adjacent the anchor.

15. The method of claim 11, wherein positioning the anchor in the hole includes positioning a rigid anchor in the hole, wherein the suture construct extends from the rigid anchor and is separate therefrom.

16. A method for coupling soft tissue to bone comprising:
forming a bore in the bone;
positioning an anchor in the bore, the anchor having a suture construct extending therefrom, the suture construct having a first loop, a second loop, a first end, and a second end, wherein the suture construct is formed of a body that defines a longitudinal extending passage therein, the first end extending into and out of a first passage portion to form the first loop and the second end extending into and out of a second passage portion to form the second loop;
passing the first loop through the soft tissue;
positioning the second loop relative to the first loop and the soft tissue;
coupling the first loop to the second loop about the soft tissue with a fastening element; and
pulling at least one of the first end or the second end to tighten the suture construct to secure the soft tissue relative to the bone.

17. The method of claim 16, wherein coupling the first loop to the second loop with the fastening element further includes coupling the first loop to the second loop with a fastening element formed of a separate piece of suture.

18. The method of claim 16, wherein positioning the first and second loops includes positioning ends of the first and second loops relative to the soft tissue and the first and second passage portions adjacent the anchor.

19. The method of claim 16, further comprising pulling the first end and the second end of the suture construct relative to the bore to tighten the suture construct to tighten the soft tissue to the bone.

20. The method of claim 16, wherein coupling the first loop to the second loop with the fastening element further includes coupling the first loop to the second loop with a fastening element formed of a suture having a knot to tie the first loop and the second loop together.

* * * * *

UNITED STATES PATENT AND TRADEMARK OFFICE
CERTIFICATE OF CORRECTION

PATENT NO. : 9,532,777 B2
APPLICATION NO. : 14/107350
DATED : January 3, 2017
INVENTOR(S) : Kaiser et al.

It is certified that error appears in the above-identified patent and that said Letters Patent is hereby corrected as shown below:

On the Title Page

On page 17, in Column 2, item (56) under "Other Publications", Line 72, delete "mailedOct. 2, 2012" and insert --mailed Oct. 2, 2012--, therefor On page 18, in Column 2, item (56) under "Other Publications", Line 18, delete "Apr. 20, 2008," and insert --Apr. 30, 2008,--, therefor On page 20, in Column 2, item (56) under "Other Publications", Line 44, delete "Apr. 16, 2011," and insert --Apr. 16, 2012,--, therefor On page 20, in Column 2, item (56) under "Other Publications", Line 49, delete "Sep. 9," and insert --Sep. 19,--, therefor On page 25, in Column 2, item (56) under "Other Publications", Line 50, delete "Apr. 25, 2016," and insert --May 25, 2016,--, therefor On page 26, in Column 2, item (56) under "Other Publications", Line 59, delete "Reinforcment," and insert --Reinforcement,--, therefor On page 27, in Column 2, item (56) under "Other Publications", Line 13, delete "Rehalibitation" and insert --Rehabilitation--, therefor In the Claims In Column 10, Line 44, in Claim 1, before "extending", delete "and" and insert --end--, therefor Signed and Sealed this
Twelfth Day of June, 2018

Andrei Iancu
*Director of the United States Patent and Trademark Office*